(12) United States Patent
Khan et al.

(10) Patent No.: US 10,696,639 B2
(45) Date of Patent: Jun. 30, 2020

(54) HETEROCYCLIC COMPOUNDS AS HIV PROTEASE INHIBITORS

(71) Applicant: Merck Sharp & Dohme Corp., Rahway, NJ (US)

(72) Inventors: Tanweer Khan, Bridgewater, NJ (US); Elizabeth Smith, Verona, NJ (US); Peter Williams, Harleysville, PA (US); Catherine Wiscount, Allentown, PA (US); Brian McKittrick, New Vernon, NJ (US); John McCauley, Maple Glen, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/466,783

(22) PCT Filed: Dec. 1, 2017

(86) PCT No.: PCT/US2017/064107
§ 371 (c)(1),
(2) Date: Jun. 5, 2019

(87) PCT Pub. No.: WO2018/106519
PCT Pub. Date: Jun. 14, 2018

(65) Prior Publication Data
US 2019/0337902 A1 Nov. 7, 2019

Related U.S. Application Data

(60) Provisional application No. 62/430,644, filed on Dec. 6, 2016.

(51) Int. Cl.
| | | |
|---|---|---|
| *C07D 233/88* | (2006.01) | |
| *A61K 31/4439* | (2006.01) | |
| *A61K 31/4168* | (2006.01) | |
| *C07D 401/12* | (2006.01) | |

(52) U.S. Cl.
CPC ........ *C07D 233/88* (2013.01); *A61K 31/4168* (2013.01); *A61K 31/4439* (2013.01); *C07D 401/12* (2013.01)

(58) Field of Classification Search
CPC ................ C07D 233/88; C07D 401/12; A61K 31/4439; A61K 31/4168
See application file for complete search history.

(56) References Cited

U.S. PATENT DOCUMENTS

2009/0111832 A1 4/2009 Barrow et al.
2014/0296532 A1 10/2014 Chen et al.

FOREIGN PATENT DOCUMENTS

WO 2008103351 A2 8/2008

OTHER PUBLICATIONS

International Search Report and Written Opinion for PCT/US217/064107, dated Feb. 20, 2019, 9 pages.

*Primary Examiner* — Laura L Stockton
(74) *Attorney, Agent, or Firm* — Carol S. Quagliato; John C. Todaro

(57) ABSTRACT

The present invention is directed to compounds of Formula (I), pharmaceutical compositions comprising the same, and their use in the inhibition of HIV protease, the inhibition of HIV replication, the prophylaxis of infection by HIV, the treatment of infection by HIV, and the prophylaxis, treatment, and delay in the onset or progression of AIDS.

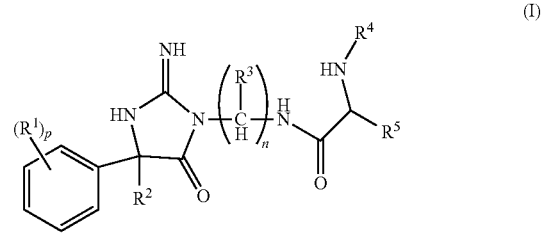

(I)

13 Claims, No Drawings

HETEROCYCLIC COMPOUNDS AS HIV PROTEASE INHIBITORS

RELATED APPLICATIONS

This application is a 35 U.S.C. § 371 filing from International Application No. PCT/PCT/US2017/064107, filed Dec. 1, 2017, which claims priority to U.S. Provisional Application No. 62/430,644, filed Dec. 6, 2016. The aforementioned PCT Application to which this application claims priority is herein incorporated by reference in its entirety.

BACKGROUND OF THE INVENTION

A retrovirus designated human immunodeficiency virus (HIV), particularly the strains known as HIV type-1 (HIV-1) virus and type-2 (HIV-2) virus, is the etiological agent of acquired immunodeficiency syndrome (AIDS), a disease characterized by the destruction of the immune system, particularly of CD4 T-cells, with attendant susceptibility to opportunistic infections, and its precursor AIDS-related complex ("ARC"), a syndrome characterized by symptoms such as persistent generalized lymphadenopathy, fever and weight loss. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl et al., *Proc. Nat'l Acad. Sci.* 1988, 85: 4686, demonstrated that genetic inactivation of the HIV encoded protease resulted in the production of immature, non-infectious virus particles. These results indicated that inhibition of the HIV protease represents a viable method for the treatment of AIDS and the prevention or treatment of infection by HIV.

Nucleotide sequencing of HIV shows the presence of a pol gene in one open reading frame [Ratner et al., *Nature* 1985, 313: 277]. Amino acid sequence homology provides evidence that the pol sequence encodes reverse transcriptase, an endonuclease, HIV protease and gag, which encodes the core proteins of the virion (Toh et al., *EMBO J.* 1985, 4: 1267; Power et al., *Science* 1986, 231: 1567; Pearl et al., *Nature* 1987, 329: 351].

Several HIV protease inhibitors are presently approved for clinical use in the treatment of AIDS and HIV infection, including indinavir (see U.S. Pat. No. 5,413,999), amprenavir (U.S. Pat. No. 5,585,397), saquinavir (U.S. Pat. No. 5,196,438), ritonavir (U.S. Pat. No. 5,484,801) and nelfinavir (U.S. Pat. No. 5,484,926). Each of these protease inhibitors is a peptide-derived peptidomimetic, competitive inhibitor of the viral protease which prevents cleavage of the HIV gag-pol polyprotein precursor. Tipranavir (U.S. Pat. No. 5,852,195) is a non-peptide peptidomimetic protease inhibitors also approved for use in treating HIV infection. The protease inhibitors are administered in combination with at least one and typically at least two other HIV antiviral agents, particularly nucleoside reverse transcriptase inhibitors such as zidovudine (AZT) and lamivudine (3TC) and/or non-nucleoside reverse transcriptase inhibitors such as efavirenz and nevirapine. Indinavir, for example, has been found to be highly effective in reducing HIV viral loads and increasing CD4 cell counts in HIV-infected patients, when used in combination with nucleoside reverse transcriptase inhibitors. See, for example, Hammer et al., *New England J. Med.* 1997, 337: 725-733 and Gulick et al., *New England J. Med.* 1997, 337: 734-739.

There is a continuing need for new compounds which are capable of treating infectious diseases, in particular, for inhibiting HIV protease and suitable for use in the treatment or prophylaxis of infection by HIV and/or for the treatment or prophylaxis or delay in the onset or progression of AIDS.

SUMMARY OF THE INVENTION

The present invention is directed to heterocyclic derivatives, pharmaceutical compositions comprising the same, and their use in the inhibition of HIV protease, the inhibition of HIV replication, the prophylaxis of infection by HIV, the treatment of infection by HIV, and the prophylaxis, treatment, and delay in the onset or progression of AIDS.

DETAILED DESCRIPTION OF THE INVENTION

The invention encompasses compounds of structural formula I

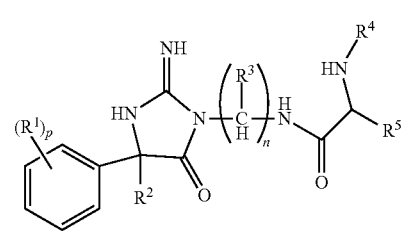

or a pharmaceutically acceptable salt thereof, wherein:

$R^1$ is selected from hydrogen, halogen, $C_{1-3}$alkyl, $C_{1-3}$haloalkyl, —$OC_{1-3}$haloalkyl, CN, —C(O)NHC$_{1-6}$alkyl and —SO$_2$C$_{1-6}$alkyl;

$R^2$ is selected from $C_{6-10}$aryl, $C_{1-6}$alkyl, $(CH_2)_kC_{1-3}$haloalkyl, $(CH_2)_kC_{3-6}$cycloalkyl, $(CH_2)_kC_{6-10}$aryl, $(CH_2)_k C_{5-10}$heterocycloalkyl and $(CH_2)_k C_{5-10}$heteroaryl, wherein $R^2$ is substituted with 0, 1, 2 or 3 $R^6$ selected from halogen, hydroxy, and $C_{1-4}$alkoxy;

$R^3$ is selected from hydrogen, $C_{1-4}$alkyl, $C_{3-8}$cycloalkyl $C_{1-6}$alkyl, $C_{3-8}$cycloalkyl, and $C_{1-4}$haloalkyl, wherein $R^3$ is substituted with 0, 1, 2 or 3 $R^7$ selected from halogen and hydroxy;

$R^4$ is selected from hydrogen, $C_{1-6}$alkyl carbonyl, $C_{1-6}$alkylcarboxy, and $C_{3-8}$alkylcycloalkylcarboxy, wherein $R^4$ is substituted with 0, 1, 2, or 3 $R^8$ selected from $C_{1-6}$alkyl and halogen;

$R^5$ is selected from $C_{3-8}$cycloalkyl $C_{1-6}$alkyl, $C_{3-8}$heterocycloalkyl $C_{1-6}$alkyl, $C_{6-10}$aryl $C_{1-6}$alkyl, and $C_{5-10}$heteroaryl $C_{1-6}$alkyl, $R^5$ is substituted with 0, 1, or 2 $R^9$ selected from $C_{1-5}$alkyl, cyano, $C_{1-6}$alkoxy, and halogen;

n is 1, 2, 3, 4, 5, or 6;

p is 0, 1, 2, or 3; and k is 0, 1, 2, 3, or 4.

Representative compounds of the instant invention include, but are not limited to, the following compounds and their pharmaceutically acceptable salts thereof:

N-{4-[2-imino-4-(2-methylpropyl)-5-oxo-4-phenylimidazolidin-1-yl]-1-methylbutyl}-N-alpha-(methoxycarbonyl)-O-methyl-L-tyrosinamide;

N-[4-(2-imino-5-oxo-4,4-diphenylimidazolidin-1-yl)butyl]-L-phenylalaninamide;

N-alpha-acetyl-N-[4-(2-imino-5-oxo-4,4-diphenylimidazolidin-1-yl)butyl]-L-phenylalaninamide;

N-[4-(2-imino-5-oxo-4,4-diphenylimidazolidin-1-yl)butyl]-N-alpha-(methoxycarbonyl)-L-phenylalaninamide;
2-amino-N-[4-(2-imino-5-oxo-4,4-diphenylimidazolidin-1-yl)butyl]-4-phenylbutanamide;
N-alpha-(ethoxycarbonyl)-N-[4-(2-imino-5-oxo-4,4-diphenylimidazolidin-1-yl)butyl]-L-phenylalaninamide;
N-[4-(2-imino-5-oxo-4,4-diphenylimidazolidin-1-yl)-1-methylbutyl]-N-alpha-(methoxycarbonyl)-L-phenylalaninamide;
methyl [2-{[4-(2-imino-5-oxo-4,4-diphenylimidazolidin-1-yl)butyl]amino}-2-oxo-1-(pyridin-3-ylmethyl)ethyl]carbamate;
N-[4-(2-imino-5-oxo-4,4-diphenylimidazolidin-1-yl)butyl]-3-pyridin-3-yl-L-alaninamide;
N-[4-(2-imino-5-oxo-4,4-diphenylimidazolidin-1-yl)butyl]-3-pyridin-4-yl-L-alaninamide;
N-{4-[4,4-bis(4-fluorophenyl)-2-imino-5-oxoimidazolidin-1-yl]-1-methylbututyl}-N-alpha-(methoxycarbonyl)-L-phenylalaninamide;
methyl [2-{[4-(2-imino-5-oxo-4,4-diphenylimidazolidin-1-yl)butyl]amino}-2-oxo-1-(pyridin-2-ylmethyl)ethyl]carbamate;
methyl [2-{[4-(2-imino-5-oxo-4,4-diphenylimidazolidin-1-yl)butyl]amino}-2-oxo-1-(pyridin-4-ylmethyl)ethyl]carbamate;
N-[5-(2-imino-5-oxo-4,4-diphenylimidazolidin-1-yl)pentyl]-L-phenylalaninamide;
N-[5-(2-imino-5-oxo-4,4-diphenylimidazolidin-1-yl)pentyl]-N-alpha-(methoxycarbonyl)-L-phenylalaninamide;
N-{4-[2-imino-4-(2-methylpropyl)-5-oxo-4-phenylimidazolidin-1-yl]butyl}-L-phenylalaninamide;
N-{4-[2-imino-4-(2-methylpropyl)-5-oxo-4-phenylimidazolidin-1-yl]butyl}-N-alpha-(methoxycarbonyl)-L-phenylalaninamide;
N-{4-[2-imino-4-(3-methylbutyl)-5-oxo-4-phenylimidazolidin-1-yl]butyl}-L-phenylalaninamide;
N-{4-[2-imino-4-(3-methylbutyl)-5-oxo-4-phenylimidazolidin-1-yl]butyl}-N-alpha-(methoxycarbonyl)-L-phenylalaninamide;
methyl [2-{[5-(2-imino-5-oxo-4,4-diphenylimidazolidin-1-yl)pentyl]amino}-2-oxo-1-(pyridin-4-ylmethyl)ethyl]carbamate;
methyl [2-({4-[2-imino-4-(2-methylpropyl)-5-oxo-4-phenylimidazolidin-1-yl]butyl}amino)-2-oxo-1-(pyridin-4-ylmethyl)ethyl]carbamate;
methyl [2-({4-[2-imino-4-(3-methylbutyl)-5-oxo-4-phenylimidazolidin-1-yl]butyl}amino)-2-oxo-1-(pyridin-4-ylmethyl)ethyl]carbamate;
N-[4-(2-imino-5-oxo-4,4-diphenylimidazolidin-1-yl)butyl]-N-alpha-{[(1-methylcyclopropyl)oxy]carbonyl}-L-phenylalaninamide;
3-cyano-N-[4-(2-imino-5-oxo-4,4-diphenylimidazolidin-1-yl)butyl]-L-phenylalaninamide;
4-fluoro-N-[4-(2-imino-5-oxo-4,4-diphenylimidazolidin-1-yl)butyl]-N-alpha-(methoxycarbonyl)-L-phenylalaninamide;
N-[4-(2-imino-5-oxo-4,4-diphenylimidazolidin-1-yl)butyl]-N-alpha-[(1-methylethoxy)carbonyl]-L-phenylalaninamide;
4-fluoro-N-{4-[2-imino-4-(2-methylpropyl)-5-oxo-4-phenylimidazolidin-1-yl]-1-methylbutyl}-N-alpha-(methoxycarbonyl)-L-phenylalaninamide;
N-{4-[2-imino-4-(2-methylpropyl)-5-oxo-4-phenylimidazolidin-1-yl]-1-methylbutyl}-N-alpha-(methoxycarbonyl)-L-phenylalaninamide;
N-{1-(cyclopropylmethyl)-4-[2-imino-4-(2-methylpropyl)-5-oxo-4-phenylimidazolidin-1-yl]butyl}-N-alpha-(methoxycarbonyl)-L-phenylalaninamide;
3-chloro-N-{1-(cyclopropylmethyl)-4-[2-imino-4-(2-methylpropyl)-5-oxo-4-phenylimidazolidin-1-yl]butyl}-N-alpha-(methoxycarbonyl)-L-phenylalaninamide;
2-chloro-N-{1-(cyclopropylmethyl)-4-[2-imino-4-(2-methylpropyl)-5-oxo-4-phenylimidazolidin-1-yl]butyl}-N-alpha-(methoxycarbonyl)-L-phenylalaninamide;
3-chloro-N-{1-cyclopropyl-4-[2-imino-4-(2-methylpropyl)-5-oxo-4-phenylimidazolidin-1-yl]butyl}-N-alpha-(methoxycarbonyl)-L-phenylalaninamide;
2-chloro-N-{1-cyclopropyl-4-[2-imino-4-(2-methylpropyl)-5-oxo-4-phenylimidazolidin-1-yl]butyl}-N-alpha-(methoxycarbonyl)-L-phenylalaninamide;
2-chloro-N-{4-[2-imino-4-(2-methylpropyl)-5-oxo-4-phenylimidazolidin-1-yl]-1-methylbutyl}-N-alpha-(methoxycarbonyl)-L-phenylalaninamide;
3-chloro-N-{4-[2-imino-4-(2-methylpropyl)-5-oxo-4-phenylimidazolidin-1-yl]-1-methylbutyl}-N-alpha-(methoxycarbonyl)-L-phenylalaninamide;
N-{1-cyclopropyl-4-[2-imino-4-(2-methylpropyl)-5-oxo-4-phenylimidazolidin-1-yl]butyl}-N-alpha-(methoxycarbonyl)-L-phenylalaninamide;
4-chloro-N-{4-[2-imino-4-(2-methylpropyl)-5-oxo-4-phenylimidazolidin-1-yl]-1-methylbutyl}-N-alpha-(methoxycarbonyl)-L-phenylalaninamide;
methyl [2-({4-[2-imino-4-(2-methylpropyl)-5-oxo-4-phenylimidazolidin-1-yl]-1-methylbutyl}amino)-1-(naphthalen-1-ylmethyl)-2-oxoethyl]carbamate;
N-{4-[2-imino-4-(2-methylpropyl)-5-oxo-4-phenylimidazolidin-1-yl]-1-methylbutyl}-2-methoxy-N-alpha-(methoxycarbonyl)-L-phenylalaninamide;
N-{4-[2-imino-4-(2-methylpropyl)-5-oxo-4-phenylimidazolidin-1-yl]-1-methylbutyl}-3-methoxy-N-alpha-(methoxycarbonyl)-L-phenylalaninamide;
methyl [1-(cyclohexylmethyl)-2-({4-[2-imino-4-(2-methylpropyl)-5-oxo-4-phenylimidazolidin-1-yl]-1-methylbutyl}amino)-2-oxoethyl]carbamate;
methyl (1-((5-(2-imino-4-isobutyl-5-oxo-4-phenylimidazolidin-1-yl)pentan-2-yl)amino)-3-(naphthalen-2-yl)-1-oxopropan-2-yl)carbamate;
3-chloro-N-[4-[2-imino-4-(2-methylpropyl)-5-oxo-4-phenylimidazolidin-1-yl]-1-(1-methylethyl)butyl]-N-alpha-(methoxycarbonyl)-L-phenylalaninamide;
2-chloro-N-[4-[2-imino-4-(2-methylpropyl)-5-oxo-4-phenylimidazolidin-1-yl]-1-(1-methylethyl)butyl]-N-alpha-(methoxycarbonyl)-L-phenylalaninamide;
N-[4-[2-imino-4-(2-methylpropyl)-5-oxo-4-phenylimidazolidin-1-yl]-1-(1-methylethyl)butyl]-N-alpha-(methoxycarbonyl)-L-phenylalaninamide;
N-[4-[2-imino-4-(2-methylpropyl)-5-oxo-4-phenylimidazolidin-1-yl]-1-(trifluoromethyl)butyl]-N-alpha-(methoxycarbonyl)-L-phenylalaninamide;
N-{1-ethyl-4-[2-imino-4-(2-methylpropyl)-5-oxo-4-phenylimidazolidin-1-yl]butyl}-N-alpha-(methoxycarbonyl)-L-phenylalaninamide;
4-chloro-N-{1-ethyl-4-[2-imino-4-(2-methylpropyl)-5-oxo-4-phenylimidazolidin-1-yl]butyl}-N-alpha-(methoxycarbonyl)-L-phenylalaninamide;
3-chloro-N-{1-ethyl-4-[2-imino-4-(2-methylpropyl)-5-oxo-4-phenylimidazolidin-1-yl]butyl}-N-alpha-(methoxycarbonyl)-L-phenylalaninamide;
2-chloro-N-{1-ethyl-4-[2-imino-4-(2-methylpropyl)-5-oxo-4-phenylimidazolidin-1-yl]butyl}-N-alpha-(methoxycarbonyl)-L-phenylalaninamide;

N-{4-cyclopropyl-4-[2-imino-4-(2-methylpropyl)-5-oxo-4-phenylimidazolidin-1-yl]butyl}-N-alpha-(methoxycarbonyl)-L-phenylalaninamide;

N-{5-cyclopropyl-4-[2-imino-4-(2-methylpropyl)-5-oxo-4-phenylimidazolidin-1-yl]pentyl}-N-alpha-(methoxycarbonyl)-L-phenylalaninamide;

N-{4-[2-imino-4-(2-methylpropyl)-5-oxo-4-phenylimidazolidin-1-yl]pentyl}-N-alpha-(methoxycarbonyl)-L-phenylalaninamide;

N-{4-[2-imino-4-(2-methylpropyl)-5-oxo-4-phenylimidazolidin-1-yl]hexyl}-N-alpha-(methoxycarbonyl)-L-phenylalaninamide; and N-{6-cyclopropyl-4-[2-imino-4-(2-methylpropyl)-5-oxo-4-phenylimidazolidin-1-yl]hexyl}-N-alpha-(methoxycarbonyl)-L-phenylalaninamide.

One embodiment of the invention includes the following compounds and their pharmaceutically acceptable salts thereof:

N-{(1S)-4-[(4R)-2-imino-4-(2-methylpropyl)-5-oxo-4-phenylimidazolidin-1-yl]-1-methylbutyl}-N-alpha-(methoxycarbonyl)-O-methyl-L-tyrosinamide;

N-[4-(2-imino-5-oxo-4,4-diphenylimidazolidin-1-yl)butyl]-L-phenylalaninamide;

N-alpha-acetyl-N-[4-(2-imino-5-oxo-4,4-diphenylimidazolidin-1-yl)butyl]-L-phenylalaninamide;

N-[4-(2-imino-5-oxo-4,4-diphenylimidazolidin-1-yl)butyl]-N-alpha-(methoxycarbonyl)-L-phenylalaninamide;

(2S)-2-amino-N-[4-(2-imino-5-oxo-4,4-diphenylimidazolidin-1-yl)butyl]-4-phenylbutanamide;

N-alpha-(ethoxycarbonyl)-N-[4-(2-imino-5-oxo-4,4-diphenylimidazolidin-1-yl)butyl]-L-phenylalaninamide;

N-[(1S)-4-(2-imino-5-oxo-4,4-diphenylimidazolidin-1-yl)-1-methylbutyl]-N-alpha-(methoxycarbonyl)-L-phenylalaninamide;

methyl [(1S)-2-{[4-(2-imino-5-oxo-4,4-diphenylimidazolidin-1-yl)butyl]amino}-2-oxo-1-(pyridin-3-ylmethyl)ethyl]carbamate;

N-[4-(2-imino-5-oxo-4,4-diphenylimidazolidin-1-yl)butyl]-3-pyridin-3-yl-L-alaninamide;

N-[4-(2-imino-5-oxo-4,4-diphenylimidazolidin-1-yl)butyl]-3-pyridin-4-yl-L-alaninamide;

N-{(1S)-4-[4,4-bis(4-fluorophenyl)-2-imino-5-oxoimidazolidin-1-yl]-1-methylbutyl}-N-alpha-(methoxycarbonyl)-L-phenylalaninamide;

methyl [(1S)-2-{[4-(2-imino-5-oxo-4,4-diphenylimidazolidin-1-yl)butyl]amino}-2-oxo-1-(pyridin-2-ylmethyl)ethyl]carbamate;

methyl [(1S)-2-{[4-(2-imino-5-oxo-4,4-diphenylimidazolidin-1-yl)butyl]amino}-2-oxo-1-(pyridin-4-ylmethyl)ethyl]carbamate;

N-[5-(2-imino-5-oxo-4,4-diphenylimidazolidin-1-yl)pentyl]-L-phenylalaninamide;

N-[5-(2-imino-5-oxo-4,4-diphenylimidazolidin-1-yl)pentyl]-N-alpha-(methoxycarbonyl)-L-phenylalaninamide;

N-{4-[2-imino-4-(2-methylpropyl)-5-oxo-4-phenylimidazolidin-1-yl]butyl}-L-phenylalaninamide;

N-{4-[2-imino-4-(2-methylpropyl)-5-oxo-4-phenylimidazolidin-1-yl]butyl}-N-alpha-(methoxycarbonyl)-L-phenylalaninamide;

N-{4-[2-imino-4-(3-methylbutyl)-5-oxo-4-phenylimidazolidin-1-yl]butyl}-L-phenylalaninamide;

N-{4-[2-imino-4-(3-methylbutyl)-5-oxo-4-phenylimidazolidin-1-yl]butyl}-N-alpha-(methoxycarbonyl)-L-phenylalaninamide;

methyl [(1S)-2-{[5-(2-imino-5-oxo-4,4-diphenylimidazolidin-1-yl)pentyl]amino}-2-oxo-1-(pyridin-4-ylmethyl)ethyl]carbamate;

methyl [(1S)-2-({4-[2-imino-4-(2-methylpropyl)-5-oxo-4-phenylimidazolidin-1-yl]butyl}amino)-2-oxo-1-(pyridin-4-ylmethyl)ethyl]carbamate;

methyl [(1S)-2-({4-[2-imino-4-(3-methylbutyl)-5-oxo-4-phenylimidazolidin-1-yl]butyl}amino)-2-oxo-1-(pyridin-4-ylmethyl)ethyl]carbamate;

N-[4-(2-imino-5-oxo-4,4-diphenylimidazolidin-1-yl)butyl]-N-alpha-{[(1-methylcyclopropyl)oxy]carbonyl}-L-phenylalaninamide;

3-cyano-N-[4-(2-imino-5-oxo-4,4-diphenylimidazolidin-1-yl)butyl]-L-phenylalaninamide;

4-fluoro-N-[4-(2-imino-5-oxo-4,4-diphenylimidazolidin-1-yl)butyl]-N-alpha-(methoxycarbonyl)-L-phenylalaninamide;

N-[4-(2-imino-5-oxo-4,4-diphenylimidazolidin-1-yl)butyl]-N-alpha-[(1-methylethoxy)carbonyl]-L-phenylalaninamide;

4-fluoro-N-{(1S)-4-[(4R)-2-imino-4-(2-methylpropyl)-5-oxo-4-phenylimidazolidin-1-yl]-1-methylbutyl}-N-alpha-(methoxycarbonyl)-L-phenylalaninamide;

N-{(1S)-4-[(4R)-2-imino-4-(2-methylpropyl)-5-oxo-4-phenylimidazolidin-1-yl]-1-methylbutyl}-N-alpha-(methoxycarbonyl)-L-phenylalaninamide;

N-{1-(cyclopropylmethyl)-4-[(4R)-2-imino-4-(2-methylpropyl)-5-oxo-4-phenylimidazolidin-1-yl]butyl}-N-alpha-(methoxycarbonyl)-L-phenylalaninamide;

3-chloro-N-{1-(cyclopropylmethyl)-4-[(4R)-2-imino-4-(2-methylpropyl)-5-oxo-4-phenylimidazolidin-1-yl]butyl}-N-alpha-(methoxycarbonyl)-L-phenylalaninamide;

2-chloro-N-{1-(cyclopropylmethyl)-4-[(4R)-2-imino-4-(2-methylpropyl)-5-oxo-4-phenylimidazolidin-1-yl]butyl}-N-alpha-(methoxycarbonyl)-L-phenylalaninamide;

3-chloro-N-{(1R)-1-cyclopropyl-4-[(4R)-2-imino-4-(2-methylpropyl)-5-oxo-4-phenylimidazolidin-1-yl]butyl}-N-alpha-(methoxycarbonyl)-L-phenylalaninamide;

2-chloro-N-{(1R)-1-cyclopropyl-4-[(4R)-2-imino-4-(2-methylpropyl)-5-oxo-4-phenylimidazolidin-1-yl]butyl}-N-alpha-(methoxycarbonyl)-L-phenylalaninamide;

2-chloro-N-{(1S)-4-[(4R)-2-imino-4-(2-methylpropyl)-5-oxo-4-phenylimidazolidin-1-yl]-1-methylbutyl}-N-alpha-(methoxycarbonyl)-L-phenylalaninamide;

3-chloro-N-{(1S)-4-[(4R)-2-imino-4-(2-methylpropyl)-5-oxo-4-phenylimidazolidin-1-yl]-1-methylbutyl}-N-alpha-(methoxycarbonyl)-L-phenylalaninamide;

N-{(1R)-1-cyclopropyl-4-[(4R)-2-imino-4-(2-methylpropyl)-5-oxo-4-phenylimidazolidin-1-yl]butyl}-N-alpha-(methoxycarbonyl)-L-phenylalaninamide;

4-chloro-N-{(1S)-4-[(4R)-2-imino-4-(2-methylpropyl)-5-oxo-4-phenylimidazolidin-1-yl]-1-methylbutyl}-N-alpha-(methoxycarbonyl)-L-phenylalaninamide;

methyl [(1S)-2-({(1S)-4-[(4R)-2-imino-4-(2-methylpropyl)-5-oxo-4-phenylimidazolidin-1-yl]-1-methylbutyl}amino)-1-(naphthalen-1-ylmethyl)-2-oxoethyl]carbamate;

N-{(1S)-4-[(4R)-2-imino-4-(2-methylpropyl)-5-oxo-4-phenylimidazolidin-1-yl]-1-methylbutyl}-2-methoxy-N-alpha-(methoxycarbonyl)-L-phenylalaninamide;

N-{(1S)-4-[(4R)-2-imino-4-(2-methylpropyl)-5-oxo-4-phenylimidazolidin-1-yl]-1-methylbutyl}-3-methoxy-N-alpha-(methoxycarbonyl)-L-phenylalaninamide;

methyl [(1S)-1-(cyclohexylmethyl)-2-({(1S)-4-[(4R)-2-imino-4-(2-methylpropyl)-5-oxo-4-phenylimidazolidin-1-yl]-1-methylbutyl}amino)-2-oxoethyl]carbamate;

methyl ((S)-1-(((S)-5-((R)-2-imino-4-isobutyl-5-oxo-4-phenylimidazolidin-1-yl)pentan-2-yl)amino)-3-(naphthalen-2-yl)-1-oxopropan-2-yl)carbamate;

3-chloro-N-[(1R)-4-[(4R)-2-imino-4-(2-methylpropyl)-5-oxo-4-phenylimidazolidin-1-yl]-1-(1-methylethyl)butyl]-N-alpha-(methoxycarbonyl)-L-phenylalaninamide;
2-chloro-N-[(1R)-4-[(4R)-2-imino-4-(2-methylpropyl)-5-oxo-4-phenylimidazolidin-1-yl]-1-(1-methylethyl)butyl]-N-alpha-(methoxycarbonyl)-L-phenylalaninamide;
N-[(1R)-4-[(4R)-2-imino-4-(2-methylpropyl)-5-oxo-4-phenylimidazolidin-1-yl]-1-(1-methylethyl)butyl]-N-alpha-(methoxycarbonyl)-L-phenylalaninamide;
N-[(1R)-4-[(4R)-2-imino-4-(2-methylpropyl)-5-oxo-4-phenylimidazolidin-1-yl]-1-(trifluoromethyl)butyl]-N-alpha-(methoxycarbonyl)-L-phenylalaninamide;
N-{(1S)-1-ethyl-4-[(4R)-2-imino-4-(2-methylpropyl)-5-oxo-4-phenylimidazolidin-1-yl]butyl}-N-alpha-(methoxycarbonyl)-L-phenylalaninamide;
4-chloro-N-{(1S)-1-ethyl-4-[(4R)-2-imino-4-(2-methylpropyl)-5-oxo-4-phenylimidazolidin-1-yl]butyl}-N-alpha-(methoxycarbonyl)-L-phenylalaninamide;
3-chloro-N-{(1S)-1-ethyl-4-[(4R)-2-imino-4-(2-methylpropyl)-5-oxo-4-phenylimidazolidin-1-yl]butyl}-N-alpha-(methoxycarbonyl)-L-phenylalaninamide;
2-chloro-N-{(1S)-1-ethyl-4-[(4R)-2-imino-4-(2-methylpropyl)-5-oxo-4-phenylimidazolidin-1-yl]butyl}-N-alpha-(methoxycarbonyl)-L-phenylalaninamide;
N-{(4R)-4-cyclopropyl-4-[(4R)-2-imino-4-(2-methylpropyl)-5-oxo-4-phenylimidazolidin-1-yl]butyl}-N-alpha-(methoxycarbonyl)-L-phenylalaninamide;
N-{(4S)-4-cyclopropyl-4-[(4R)-2-imino-4-(2-methylpropyl)-5-oxo-4-phenylimidazolidin-1-yl]butyl}-N-alpha-(methoxycarbonyl)-L-phenylalaninamide;
N-{(4S)-5-cyclopropyl-4-[(4R)-2-imino-4-(2-methylpropyl)-5-oxo-4-phenylimidazolidin-1-yl]pentyl}-N-alpha-(methoxycarbonyl)-L-phenylalaninamide;
N-{(4R)-4-[(4R)-2-imino-4-(2-methylpropyl)-5-oxo-4-phenylimidazolidin-1-yl]pentyl}-N-alpha-(methoxycarbonyl)-L-phenylalaninamide;
N-{(4R)-4-[(4R)-2-imino-4-(2-methylpropyl)-5-oxo-4-phenylimidazolidin-1-yl]hexyl}-N-alpha-(methoxycarbonyl)-L-phenylalaninamide; and
N-{(4R)-6-cyclopropyl-4-[(4R)-2-imino-4-(2-methylpropyl)-5-oxo-4-phenylimidazolidin-1-yl]hexyl}-N-alpha-(methoxycarbonyl)-L-phenylalaninamide.

The invention is described using the following definitions unless otherwise indicated.

When any variable (e.g. aryl, heteroaryl, $R^1$, $R^5$, etc.) occurs more than one time in any substituent, its definition on each occurrence is independent at every other occurrence. Also, combinations of substituents/or variables are permissible only if such combinations result in stable compounds.

The wavy line ~~~, as used herein, indicates a point of attachment to the rest of the compound.

The term "$C_{1-6}$" includes alkyls containing 6, 5, 4, 3, 2, or 1 carbon atoms.

Lines drawn into the ring systems, such as, for example:

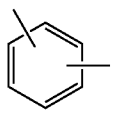

indicate that the indicated line (bond) may be attached to any of the substitutable ring atoms.

The term "alkyl," as used herein, refers to an aliphatic hydrocarbon group having one of its hydrogen atoms replaced with a bond. An alkyl group may be straight or branched and contain from about 1 to about 10 carbon atoms. In different embodiments, an alkyl group contains from 1 to 6 carbon atoms ($C_{1-6}$ alkyl) or from about 1 to about 3 carbon atoms ($C_{1-3}$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "alkoxy" represents a linear or branched alkyl group of indicated number of carbon atoms attached through an oxygen bridge (alkyl-O—). $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

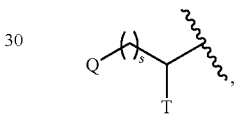

wherein s is an integer equal to zero, 1 or 2, the structure is

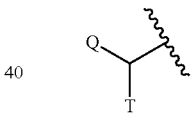

when s is zero.

The term "halogen" (or "halo") refers to fluorine, chlorine, bromine and iodine (alternatively referred to as fluoro (F), chloro (Cl), bromo (Br), and iodo (I)).

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl. In one embodiment, an aryl group contains from about 6 to about 10 carbon atoms. In one embodiment, an aryl group can be optionally fused to a cycloalkyl or cycloalkanoyl. Non-limiting examples of aryl groups include phenyl and naphthyl. In one embodiment, an aryl group is phenyl. Unless otherwise indicated, an aryl group is unsubstituted.

"Carboxy" refers to the functional group —C(O)OR, for example: ethylcarboxy is

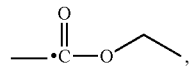

phenylcarboxy is

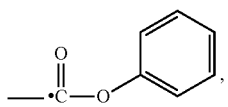

and cyclopropycarboxy is

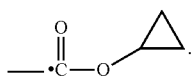

"Celite®" (Fluka) diatomite is diatomaceous earth, and can be referred to as "celite".

"Cycloalkyl" or "$C_{3-12}$ cycloalkyl" means any univalent radical derived from a monocyclic or bicyclic ring system having 3 to 12 ring carbons atoms; said ring system may be (a) a $C_3$ to a $C_8$ monocyclic, saturated ring, or a partially unsaturated ring, or (b) a bicyclic saturated ring. Here, the point of attachment for a "cycloalkyl" to the rest of the molecule is on the saturated ring. For a bicyclic system, the rings are fused across two adjacent ring carbon atoms (e.g., decalin), or are bridged groups (e.g., norbornane). Additional examples within the above meaning include, but are not limited to univalent radicals of cyclopropane, cyclobutane, cyclopentane, cyclohexane, decalin, and bicyclo[2.2.2]octane.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

"Heterocycloalkyl" or "$C_{3-12}$ heterocycloalkyl" refers to a "cycloalkyl" wherein one or more of the carbon atoms are replaced by at least one heteroatom, such as, for example, 1 to 4 heteroatoms selected from nitrogen, oxygen and sulfur. Additional examples within the above meaning include, but are not limited to, univalent radicals of 4,5,6,7-tetrahydropyrazolo[1,5-a]pyrazine, tetrahydro-2H-pyranyl, 2-oxa-5-azabicyclo[2.2.1]heptane, and thietane.

The term "heteroaryl", as used herein except where noted, represents a stable 5- to 7-membered monocyclic- or stable 9- to 11-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$ haloalkyl, for example, includes —$CF_3$, —$CF_2CF_3$, —$CHFCH_3$, and the like.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "═O". The term "carbonyl" means "C═O."

Structural representations of compounds having substituents terminating with a methyl group may display the terminal methyl group either using the characters "$CH_3$", e.g. "—$CH_3$" or using a straight line representing the presence of the methyl group, e.g. "——", i.e., "⅏—— $CH_3$" and "⅏—— " have equivalent meanings.

Under standard nomenclature used throughout this disclosure, the terminal portion of the designated side chain is described first, followed by the adjacent functionality toward the point of attachment. For example, a C1-5 alkylcarbonylamino C1-6 alkyl substituent is equivalent to

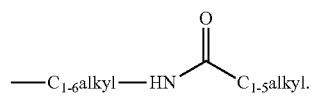

For variable definitions containing terms having repeated terms, e.g., $(CR_iR_j)_r$, where r is the integer 2, $R_i$ is a defined variable, and $R_j$ is a defined variable, the value of $R_i$ may differ in each instance in which it occurs, and the value of $R_j$ may differ in each instance in which it occurs. For example, if $R_i$ and $R_j$ are independently selected from the group consisting of methyl, ethyl, propyl and butyl, then $(CR_iR_j)_2$ can be

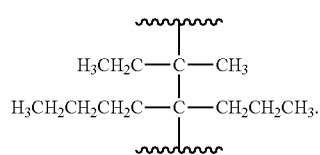

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 3 heteroatoms" means the ring can contain 1, 2 or 3 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, or 4 heteroatoms. As another example, a moeity described as optionally substituted with "from 1 to 3 substituents" is intended to include as aspects thereof, such moeity substituted with 1 to 3 substituents, 2 or 3 substituents, 3 substituents, 1 or 2 substituents, 2 substituents, or 1 substituent.

Unless expressly stated to the contrary, substitution by a named substituent is permitted on any atom in a chain or ring provided such substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

To the extent substituents and substituent patterns provide for the existence of tautomers (e.g., keto-enol tautomers) in the compounds of the invention, all tautomeric forms of these compounds, whether present individually or in mixtures, are within the scope of the present invention. Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present.

"Patient" for the purposes of the present invention includes humans and other animals, particularly mammals and other organisms. Thus the methods are applicable to both human therapy and veterinary applications.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

In one embodiment of the invention, $R^1$ is selected from hydrogen, halogen, $C_{1-3}$alkyl, $C_{1-3}$haloalkyl, —$OC_{1-3}$haloalkyl, CN, —C(O)NH $C_{1-6}$alkyl and —$SO_2C_{1-6}$alkyl. In one embodiment of the invention, $R^1$ is selected from hydrogen, halogen, $C_{1-3}$alkyl, $C_{1-3}$haloalkyl, —$OC_{1-3}$haloalkyl, CN, —C(O)NH $C_{1-3}$alkyl and —$SO_2C_{1-3}$alkyl. In a variant of this embodiment, $R^1$ is selected from hydrogen, fluoro, bromo, chloro, methyl, ethyl, trifluoroethyl, trifluoromethyl, $C_{1-3}$haloalkyl, —$OC_{1-3}$haloalkyl, CN, —C(O)NHCH$_3$, —$SO_2CH_3$, and —$SO_2$ethyl.

In yet another embodiment of this invention, $R^1$ is selected from hydrogen, fluoro, bromo, chloro, methyl, ethyl, trifluoroethyl, trifluoromethyl, —O(trifluoromethyl), CN, —O(trifluoroethyl), —C(O)NHCH$_3$, —$SO_2CH_3$, and —$SO_2$ethyl.

In one embodiment of the invention, $R^1$ is hydrogen. In another embodiment of the invention, $R^1$ is a halogen selected from fluoro and chloro. In a variant of this embodiment, $R^1$ is fluoro.

In one embodiment of the invention, p is 0, 1, or 2. In a variant of this embodiment, p is 0 or 1.

In one embodiment of the invention, k is 0, 1, 2 or 3. In a variant of this embodiment, k is 0, 1 or 2. In a variant of this embodiment, k is 0 or 1.

An embodiment of the invention of formula I is realized when $R^2$ is selected from isobutyl, isopentyl, $(CH_2)_nCF_3$, $(CH_2)_n$cyclopropyl, phenyl, pyridyl, pyranyl, $(CH_2)_n$tetrahydropyranyl, and $(CH_2)_n$tetrahydrofuranyl, and wherein $R^2$ is substituted with 0, 1, 2 or 3 $R^6$ selected from halogen, hydroxy, and $C_{1-4}$alkoxy.

A variant of this embodiment of this aspect of the invention is realized when $R^2$ is selected from isobutyl, isopentyl, $(CH_2)_nCF_3$, $(CH_2)_n$cyclopropyl, and phenyl, said isobutyl, isopentyl and phenyl, and wherein $R^2$ is substituted with 0, 1, 2 or 3 $R^6$ selected from halogen, hydroxy, and $C_{1-4}$alkoxy.

An embodiment of the invention of formula I is realized when $R^2$ is $C_{6-10}$aryl, substituted with 0, 1, 2 or 3 $R^6$ selected from halogen, hydroxy, and $C_{1-4}$alkoxy. An embodiment of the invention of formula I is realized when $R^2$ is $C_{1-6}$alkyl substituted with 0, 1, 2 or 3 $R^6$ selected from halogen, hydroxy, and $C_{1-4}$alkoxy.

In another embodiment of the invention, $R^2$ is selected from phenyl, isopentyl, and isobutyl, and $C_{1-6}$alkyl and $R^2$ is substituted with 0, 1, 2 or 3 $R^6$ selected from halogen, hydroxy, and $C_{1-4}$alkoxy. In a variant of this embodiment, $R^2$ is selected from phenyl, isopentyl, and isobutyl, and $C_{1-6}$alkyl and $R^2$ is substituted with 0, 1, 2 or 3 $R^6$ selected from fluoro, hydroxy, and methoxy. In yet another variant of this embodiment, $R^2$ is selected from phenyl, isopentyl, and isobutyl, and $C_{1-6}$alkyl and $R^2$ is substituted with 0, 1, 2 or 3 fluoro groups.

An embodiment of the invention of formula I is realized when $R^3$ is selected from hydrogen, methyl, ethyl, methylethyl (isopropyl), cylcopropylmethyl, cyclopropyl, and cyclopropylethyl, wherein $R^3$ is substituted with 0, 1, 2 or 3 $R^7$ selected from halogen and hydroxy. In a variant of this embodiment, $R^3$ is selected from hydrogen, methyl, ethyl, methylethyl (isopropyl), cylcopropylmethyl, cyclopropyl, and cyclopropylethyl, wherein $R^3$ is substituted with 0, 1, 2 or 3 fluoro.

An embodiment of the invention of formula I is realized when $R^4$ is selected from hydrogen, methylcarbonyl, methylcarboxy, ethylcarboxy, cyclopropyl carboxy, and isopropylcarboxy, wherein $R^4$ is substituted with 0, 1, 2, or 3 $R^8$ selected from $C_{1-6}$alkyl and halogen. In a variant of this embodiment, $R^4$ is selected from hydrogen, methylcarbonyl, methylcarboxy, ethylcarboxy, cyclopropyl carboxy, and isopropylcarboxy, wherein $R^4$ is substituted with 0, 1, 2, or 3 methyl groups.

An embodiment of the invention of formula I is realized when $R^5$ is selected from benzyl, phenyethyl, pyridinylmethyl, naphthalenylmethyl, and cyclohexylmethyl, wherein $R^5$ is substituted with 0, 1, or 2 $R^9$ selected from $C_{1-5}$alkyl, cyano, $C_{1-6}$alkoxy, and halogen. In a variant of this embodiment, $R^5$ is selected from benzyl, phenyethyl, pyridinylmethyl, naphthalenylmethyl, and cyclohexylmethyl, wherein $R^5$ is substituted with 0, 1, or 2 $R^9$ selected from cyano, methoxy, fluoro and chloro.

In one embodiment of the invention, n is 3, 4, 5, or 6. In a variant of this embodiment, n is 3, 4 or 5. In another variant, n is 4 or 5.

In another embodiment of the invention, n is 1, 2 or 3.

Another embodiment of the invention is a compound of formula I, or the pharmaceutically acceptable salts thereof:

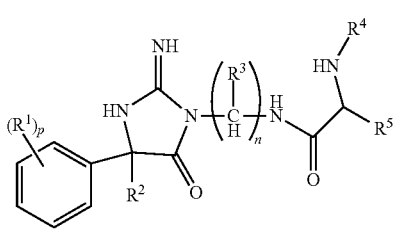

I $R^1$ is hydrogen or fluoro;
$R^2$ is selected from phenyl and $C_{1-6}$alkyl and $R^2$ is substituted with 0, 1, 2 or 3 $R^6$ selected from halogen, hydroxy, and $C_{1-4}$alkoxy;
$R^3$ is selected from hydrogen, methyl, ethyl, methylethyl (isopropyl), cylcopropylmethyl, cyclopropyl, and cyclopropylethyl, wherein $R^3$ is substituted with 0, 1, 2 or 3 fluoro;
$R^4$ is selected from hydrogen, methylcarbonyl, methylcarboxy, ethylcarboxy, cyclopropyl carboxy, and isopropylcarboxy, wherein $R^4$ is substituted with 0, 1, 2, or 3 methyl groups;
$R^5$ is selected from benzyl, phenyethyl, pyridinylmethyl, naphthalenylmethyl, and cyclohexylmethyl, wherein $R^5$ is substituted with 0, 1, or 2 $R^9$ selected from cyano, methoxy, fluoro and chloro;
p is 0, 1, or 2; and
n is 4 or 5.

In one embodiment of the invention, $R^2$ is selected from phenyl, isopentyl, and isobutyl.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (which includes hydrates) and solvated salts of such racemates, enantiomers, diastereomers and tautomers and mixtures thereof.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof).

When the compounds of Formula I contain one or more acidic or basic groups the invention also includes the corresponding pharmaceutically acceptable salts. Thus, the compounds of Formula I which contain acidic groups can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Another embodiment of the present invention is a compound of Formula I, or a pharmaceutically acceptable salt thereof, as originally defined or as defined in any of the foregoing embodiments, aspects, classes, or subclasses, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The compounds of the invention have two or more asymmetric centers and can occur as mixtures of stereoisomers. It is understood that a substantially pure compound can be either a substantially pure mixture of stereoisomers or a substantially pure individual diastereomer or enantiomer. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

Furthermore, compounds of the present invention may exist in amorphous form and/or one or more crystalline forms, and as such all amorphous and crystalline forms of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_5$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as 3-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and $Y^5$ is mono-N— or di-N,N—$(C_1$-$C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The invention also encompasses methods for the treatment or prophylaxis of infection by HIV or for the treatment, prophylaxis, or delay in the onset of AIDS in a subject in need thereof, which comprises administering to the subject an effective amount of a compound of the invention or a pharmaceutically acceptable salt thereof.

The invention also encompasses a compound of the invention, or a pharmaceutically acceptable salt thereof, for use in the preparation of a medicament for the inhibition of HIV protease, for the treatment or prophylaxis of infection by HIV, or for the treatment, prophylaxis, or delay in the onset of AIDS in a subject in need thereof.

The invention also encompasses a pharmaceutical composition comprising an effective amount of a compound of the invention, or a pharmaceutically acceptable salt thereof, and a pharmaceutically acceptable carrier and further comprising an effective amount of an anti-HIV agent selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

Compounds of formula II and III each form a subset of the compounds included in formula I. Any description which follows that refers to a compound of Formula I also applies to a compound of formula II and III and all embodiments thereof.

Other embodiments of the present invention include the following:

(a) A pharmaceutical composition comprising an effective amount of a compound of formula I as defined above, or a pharmaceutically acceptable salt thereof, and a pharmaceutically acceptable carrier.

(b) A pharmaceutical composition which comprises the product prepared by combining (e.g., mixing) an effective amount of a compound of formula I as defined above, or a pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(e) The pharmaceutical composition of (d), wherein the antiviral is selected from the group consisting of HIV reverse transcriptase inhibitors and HIV integrase inhibitors.

(f) A combination which is (i) a compound of Formula I as defined above, or a pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV protease, for treatment or prophylaxis of infection by HIV, or for treatment, prophylaxis of, or delay in the onset or progression of AIDS.

(g) The combination of (f), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(h) The combination of (g), wherein the antiviral is selected from the group consisting of HIV reverse transcriptase inhibitors and HIV integrase inhibitors.

(i) A method for the inhibition of HIV protease in a subject in need thereof which comprises administering to the subject an effective amount of a compound of Formula I or a pharmaceutically acceptable salt thereof.

(j) A method for the prophylaxis or treatment of infection by HIV (e.g., HIV-1) in a subject in need thereof which comprises administering to the subject an effective amount of a compound of Formula I or a pharmaceutically acceptable salt thereof.

(k) The method of (j), wherein the compound of Formula I is administered in combination with an effective amount of at least one other HIV antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(l) The method of (k), wherein the at least one other HIV antiviral is selected from the group consisting of HIV reverse transcriptase inhibitors and HIV integrase inhibitors.

(m) A method for the prophylaxis, treatment or delay in the onset or progression of AIDS in a subject in need thereof which comprises administering to the subject an effective amount of a compound of Formula I or a pharmaceutically acceptable salt thereof.

(n) The method of (m), wherein the compound is administered in combination with an effective amount of at least one other HIV antiviral, selected from the group consisting of HIV protease inhibitors, HIV reverse transcriptase inhibitors, HIV integrase inhibitors, HIV fusion inhibitors, HIV entry inhibitors, and HIV maturation inhibitors.

(o) The method of (n), wherein the at least one other HIV antiviral is selected from the group consisting of HIV reverse transcriptase inhibitors and HIV integrase inhibitors.

(p) A method for the inhibition of HIV protease in a subject in need thereof which comprises administering to the subject the pharmaceutical composition of (a), (b), (c) or (d) or the combination of (e) or (f).

(q) A method for the prophylaxis or treatment of infection by HIV (e.g., HIV-1) in a subject in need thereof which comprises administering to the subject the pharmaceutical composition of (a), (b), (c), (d) or (e).

(r) A method for the prophylaxis, treatment, or delay in the onset or progression of AIDS in a subject in need thereof which comprises administering to the subject the pharmaceutical composition of (a), (b), (c), (d) or (e).

The present invention also includes a compound of formula I, or a pharmaceutically acceptable salt thereof, (i) for use in, (ii) for use as a medicament for, or (iii) for use in the manufacture/preparation of a medicament for: (a) therapy (e.g., of the human body), (b) medicine, (c) inhibition of HIV protease, (d) treatment or prophylaxis of infection by HIV, or (e) treatment, prophylaxis of, or delay in the onset or progression of AIDS. In these uses, the compounds of the present invention can optionally be employed in combination with one or more other anti-HIV agents selected from HIV antiviral agents, anti-infective agents, and immunomodulators.

Additional embodiments of the invention include the pharmaceutical compositions, combinations and methods set forth in (a)-(r) above and the uses (i)(a)-(e) through (iii)(a)-(e) set forth in the preceding paragraph, wherein the compound of the present invention employed therein is a compound of one of the embodiments, aspects, classes or subclasses described above. In all of these embodiments etc., the compound can optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of formula I or a pharmaceutically acceptable carrier and optionally one or more excipients, it is understood that the term "substantially pure" is in reference to a compound of formula I or its salt per se.

The methods of the present invention involve the use of compounds of the present invention in the inhibition of HIV protease (e.g., wild type HIV-1 and/or mutant strains thereof), the prophylaxis or treatment of infection by human immunodeficiency virus (HIV) and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery.

In general, compounds that are HIV protease inhibitors can be identified as those compounds which, when tested in the "Cell-based HIV Infection Assay using a Reporter" assay described below, have an inflection point (IP) of 10 µM, particularly 5 µM or less, preferably 1 µM or less, and more preferably 0.25 µM or less.

The term "administration" and variants thereof (e.g., "administering" a compound) in reference to a compound of formula I mean providing the compound to the individual in need of treatment or prophylaxis and includes both self-administration and administration to the patient by another person. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" which is an amount effective for inhibiting HIV protease (wild type and/or mutant strains thereof), inhibiting HIV replication (either of the foregoing which may also be referred to herein as an "inhibition effective amount"), treating HIV infection, treating AIDS, delaying the onset of AIDS and/or slowing progression of AIDS. In another embodiment, the effective amount is a "prophylactically effective amount" which is an amount effective for prophylaxis of HIV infection or prophylaxis of AIDS. It is understood that an effective amount can simultaneously be both a therapeutically effective amount, e.g., for treatment HIV infection, and a prophylactically effective amount, e.g., for prevention or reduction of risk of developing AIDS. When the active compound (i.e., active ingredient) is administered as the salt, references to the amount of active ingredient are to the free form (i.e., the non-salt form) of the compound.

In the methods of the present invention (e.g., inhibiting HIV protease, treating or prophylaxis of HIV infection, inhibiting HIV replication, treating or prophylaxis of AIDS, delaying the onset of AIDS, or delaying or slowing progression of AIDS), the compounds of formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following routes: orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990 and in *Remington—The Science and Practice of Pharmacy*, 21st edition, Lippincott Williams & Wilkins, 2005.

The compounds of formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In some cases, depending on the potency of the compound or the individual response, it may be necessary to deviate upwards or downwards from the given daily dose. Furthermore, the compound may be formulated for immediate or modified release such as extended or controlled release.

As noted above, the present invention is also directed to use of a compound of formula I with one or more additional anti-HIV agents. An "anti-HIV agent" is any agent which is directly or indirectly effective in the inhibition of HIV reverse transcriptase, protease, or another enzyme required for HIV replication or infection, the inhibition of HIV replication, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

Antiviral Agents for Treating HIV infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | InI |
| doravirine, MK-1439 | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-eoxyadenosine) | nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| Rilpivirine | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tipranavir, Aptivus ® | PI |
| vicriviroc | EI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, delavirdine mesylate, indinavir sulfate, atazanavir sulfate, nelfinavir mesylate, saquinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57th edition (2003), the 58th edition (2004), or the 59th edition (2005) and the current Physicians' Desk Reference (68th ed.). (2014), Montvale, N.J.: PDR Network. The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be used for these purposes.

METHODS OF SYNTHESIS AND SCHEMES AND EXAMPLES

The abbreviations used herein have the following tabulated meanings. Abbreviations not tabulated below have their meanings as commonly used unless specifically stated otherwise.

| | |
|---|---|
| BAS | Bovine serum albumin |
| Benzil; Bibenzoyl; Dibenzoyl | Diphenylethanedione; Diphenylglyoxal; 1,2-Diphenylethane-1,2-dione; 1,2-Diphenylethanedione |
| BOC | tert-butoxycarbamate |
| Cbz | carboxybenzyl |
| CH$_3$CN; MeCN | acetonitrile |
| Chiral SFC | chiral super critical fluid chromatography |
| DCM | dichloromethane |
| DEA | diethanolamine |
| DIAD | diisopropylazodicarboxylate |
| DMAP | dimethylaminopyridine |
| DMF | N,N-dimethylformamide |
| DMSO | dimethyl sulfoxide |
| EDC | 1-ethyl-3-(3-dimethylaminopropyl) carbodiimide |
| EtOAc | ethyl acetate |
| EtOH | ethonol |
| Fmoc | fluorenylmethyloxycarbonyl chloride |
| FBS | fetal bovine serum |
| h, hr. | hour |
| GFP | green fluorescent protein |
| HCl | hydrogen chloride |
| HOAt | 1-hydroxy-7-azabenzotriazole |
| HOBt | hydroxybenzotriazole |
| HPLC | high pressure liquid chromatography |
| HRMS | High Resolution Mass Spectrometry |
| Hunig's base; DIPEA; DIEA | N,N-Diisopropylethylamine |
| IPA | 2-propanol |
| LiHMDS | lithium bis(trimethylsilyl)amide. |
| LRMS | low resolution mass spectrometry |
| MeOH | methanol |
| MgSO$_4$ | magnesium sulfate |
| MPLC | medium pressure liquid chromatography |
| NaOH | sodium hydroxide |
| NMO | 4-methylmorpholine N-oxide |
| Pd(OH)$_2$/C | Palladium hydroxide on carbon |
| PPh$_3$ | Triphenylphosphine |
| rt, r.t. or RT | Room temperature |
| tBuOH | tert-butyl alcohol |
| TEA | triethylamine |
| TFA | trifluoroacetic acid |

-continued

| | |
|---|---|
| THF | tetrahydrofuran |
| TsOH | p-toluenesulfonic acid |
| NMO | 4-methylmorpholine N-oxide |
| NMR | nuclear magnetic resonance |
| TLC | thin layer chromatography |

Alkyl Group Abbreviations

| | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-Pen | cyclopentyl |
| c-Hex | cyclohexyl |

Methods of Synthesis

The compounds of the present invention can be prepared according to the following general schemes using readily available starting materials, reagents and conventional synthesis procedures, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. Unless otherwise indicated, all variables are as defined above. In the examples that follow, when a nitrogen atom is depicted without the necessary hydrogen atoms to complete the valence, it is assumed those hydrogen atoms are present unless specifically stated to the contrary. The invention will now be illustrated in the following non-limiting Examples in which, unless otherwise stated:

All reactions were stirred (mechanically, stir bar/stir plate, or shaken) and conducted under an inert atmosphere of nitrogen or argon unless specifically stated otherwise.

All temperatures are degrees Celsius (° C.) unless otherwise noted.

Ambient temperature is 15-25° C.

Most compounds were purified by reverse-phase preparative HPLC, MPLC on silica gel, recrystallization and/or swish (suspension in a solvent followed by filtration of the solid).

The course of the reactions was followed by thin layer chromatography (TLC) and/or LCMS and/or NMR and reaction times are given for illustration only.

All end products were analyzed by NMR and LCMS.

Intermediates were analyzed by NMR and/or TLC and/or LCMS.

General Synthetic Schemes

The compounds of Formula I can be prepared using the general synthetic reaction schemes shown in Methods A and B.

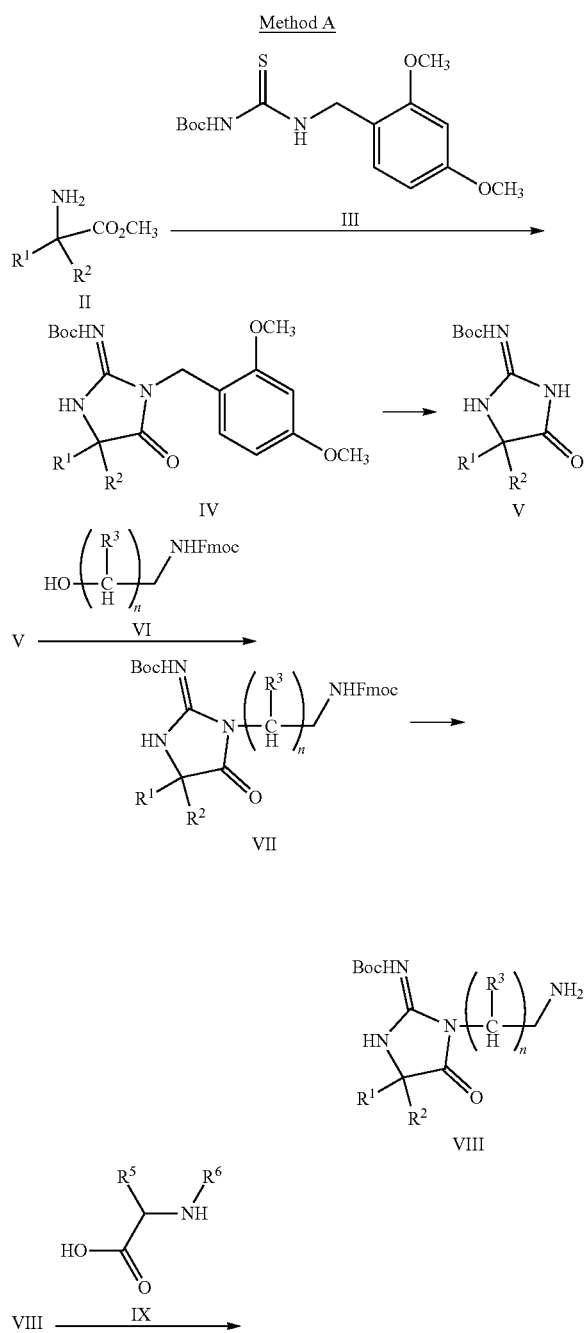

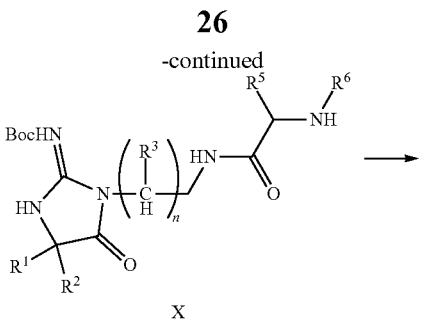

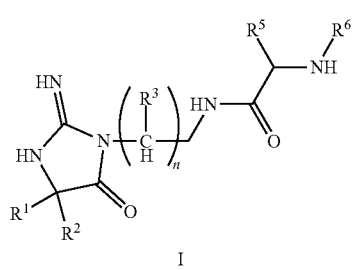

Method A provides a route to Formula I by first condensing the disubstituted amino acid ester (II) with thioureas (III) which have orthogonal protecting groups. For example, using a BOC protecting group on one nitrogen and a dimethoxybenzyl group on the other nitrogen (which can be prepared as described in the literature—for example see McKittrick et al. Bioorganic & Medicinal Chemistry Letters (2015), 25(7), 1592-1596 and references therein) and using a coupling agent such as a carbodiimide under standard peptide coupling conditions to provide the iminohydatoin compounds (IV). The resultant compounds (IV) are then treated with palladium under an atmosphere of hydrogen to provide intermediates (V). Reaction of compounds (V) with suitable alcohols (VI) under Mitsunobu conditions provides compounds VII (For Mitsunobu reactions, see Mitsunobu, O. et al., "Preparation of Esters of Carboxylic and Phosphoric Acid via Quaternary Phosphonium Salts", Bull. Chem. Society of Japan, (1967) 40(10): 2380-2384). Deprotection of compounds (VII) with a secondary amine, such as diethylamine, provides amines (VIII). Compounds (VIII) are then converted to the desired amides using peptide coupling chemistry such as a carbodiimide with HOAt, DMAP and a base such as DIEA with a carboxylic acid IX to afford the resultant amides (X). The resultant amides (X) are then treated with an acid such as TFA or HCl to remove the BOC protecting group to provide compounds of Formula I.

Method B

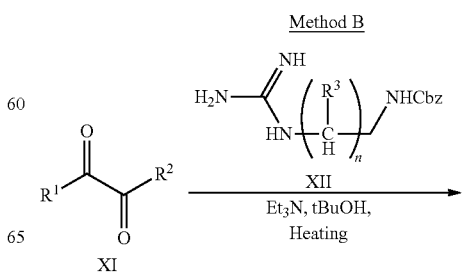

Intermediate I-1

(S)-2-((Methoxycarbonyl)amino)-3-(4-methoxyphenyl)propanoic acid (I-1)

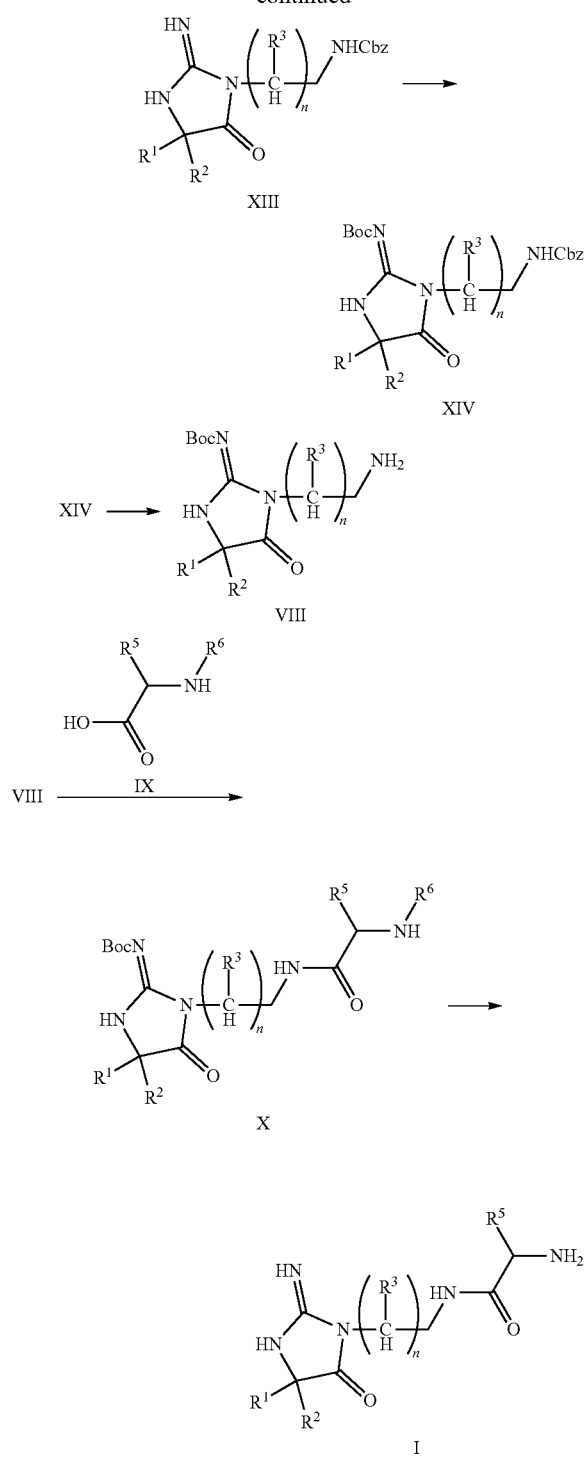

Step 1: (Isothiocyanatomethyl)-2,4-dimethoxybenzene

To a solution of 2,4-dimethoxybenzylamine (Sigma-Aldrich) (6.6 mL, 43.5 mmol) in DCM (85 mL) was added saturated aqueous sodium bicarbonate solution (85 mL) and the mixture was stirred vigorously at RT for 15 min. Stirring was stopped; then thiophosgene (6.6 mL, 87 mmol) was added via syringe to the bottom layer. The mixture was stirred at RT for 90 min then the aqueous layer was separated and the organic layer was washed with brine, dried over $Na_2SO_4$ and concentrated in vacuo twice from DCM to give 1-(isothiocyanatomethyl)-2,4-dimethoxybenzene.

Step 2: Compound I-1

Alternatively, the amines (VIII) can be prepared through another route. First, substituted guanidines (XII) are condensed with alpha diketones (XI). Then compounds (XIII) are treated with di-tert-butyl dicarbonate and DIEA to provide the orthogonally protected compounds (XIV). Compounds (XIV) are then treated with palladium under an atmosphere of hydrogen to provide intermediates (VIII). The compounds (VIII) are then converted to compounds of Formula I according to Method A.

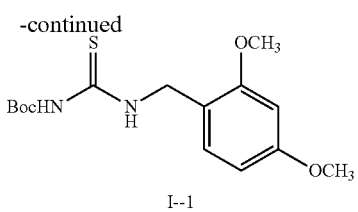

To a suspension of 60% sodium hydride in hexanes (3.4 g, 85 mmol) in anhydrous THF (100 mL) at 0° C. was added tert-butylcarbamate (Sigma-Aldrich) (7.4 g, 63 mmol), and the mixture was stirred for 15 min. A solution of 1-(isothiocyanatomethyl)-2,4-dimethoxybenzene (9.1 g, 43.5 mmol) in anhydrous THF (50 mL) was then added over 15 min, and the reaction was allowed to warm up to RT and stirred overnight. The final mixture was quenched with water and 10% aqueous phosphoric acid until neutral pH, extracted with EtOAc, dried over Na$_2$SO$_4$ and concentrated in vacuo. The residue was purified by chromatography over silica gel (eluting with hexanes/EtOAc 100:0 to 80:20) to afford compound I-1.

Intermediate I-2

(9H-Fluoren-9-yl)methyl (S)-(5-hydroxypentan-2-yl)carbamate (I-2)

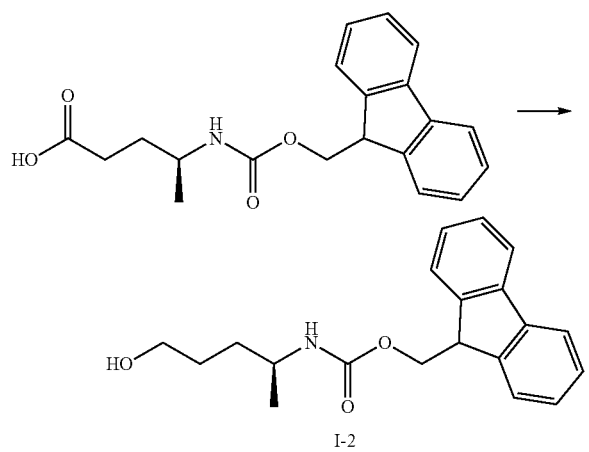

Methylchloroformate (1.5 g, 16 mmol) was added dopwise to a solution of (S)-4-((((9H-fluoren-9-yl)methoxy)carbonyl)amino)pentanoic acid (Fluorochem) (5.0 g, 15 mmol) and NMO (1.8 g, 18 mmol) in THF (50 ml) at 0° C. The mixture was stirred for 1 h, then transferred to a vigorously stirred mixture of NaBH$_4$ (4.5 g, 120 mmol) in water (10 mL) and THF (50 ml) which had been pre-cooled in an ice-water bath. The mixture was stirred in an ice-water bath for 1 h then at RT for 1 h. The mixture was diluted with water and extracted with EtOAc (3×). The combined EtOAc layers were washed with brine, dried (MgSO$_4$), and filtered. The solvents were removed in vacuo and the solid was suspended in 3:1 hexane:EtOAc and stirred vigorously for 24 h. The solid was collected by filtration and dried to give compound I-2.

Intermediate I-3

(S)-2-((Methoxycarbonyl)amino)-3-(4-methoxyphenyl)propanoic acid (I-3)

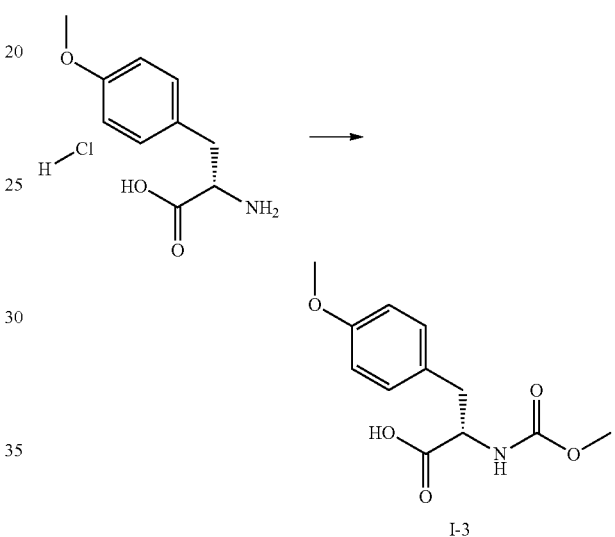

(S)-2-Amino-3-(4-methoxyphenyl)propanoic acid hydrochloride (Fluorochem) (1.0 g, 4.3 mmol) was dissolved in 1M NaOH (8.6 ml). Na$_2$CO$_3$ (0.23 g, 2.2 mmol) was added and the reaction mixture was cooled in an ice bath. Methyl chloroformate (0.32 ml, 4.1 mmol) was added dropwise and the reaction stirred at 0° C. for 30 min, then warmed to RT and stirred for 1 hour. The reaction was acidified with 3N HCl and extract with DCM. The combined organic extracts were washed combined organics with brine, dry over Na$_2$SO$_4$ and the solvent removed in vacuo to afford compound I-3.

Example 1

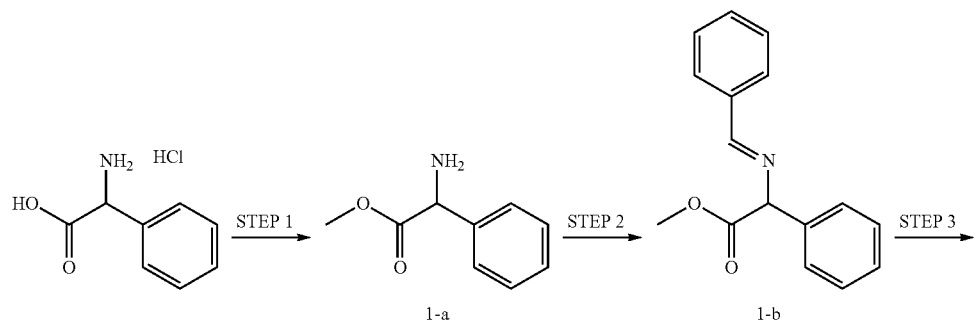

-continued
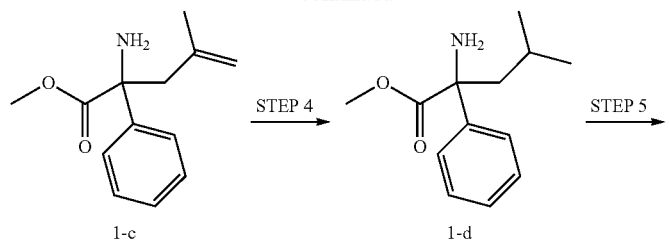
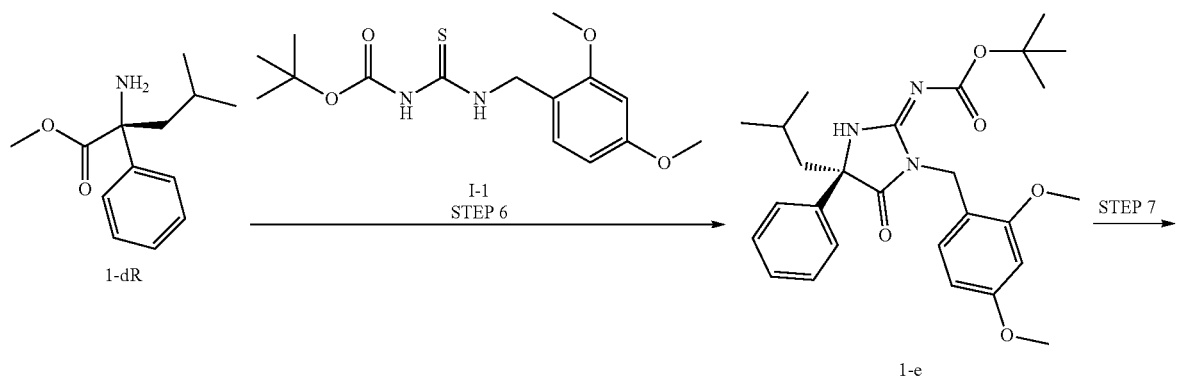
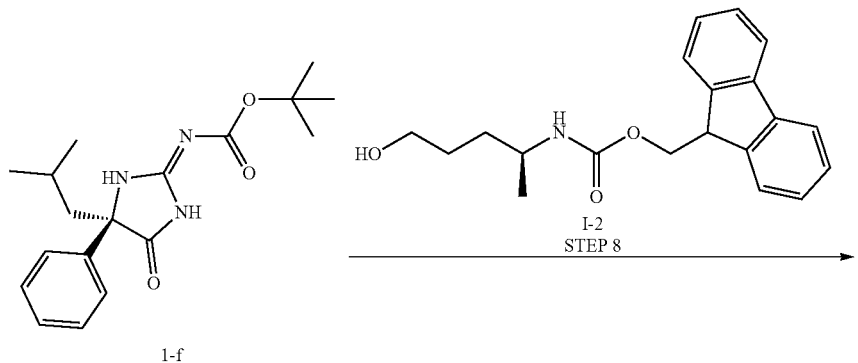
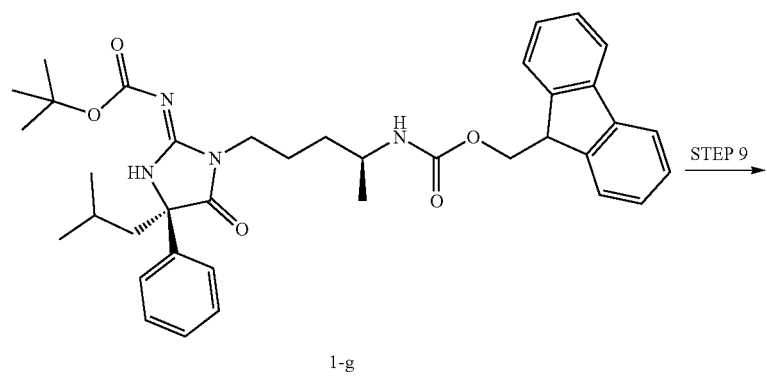

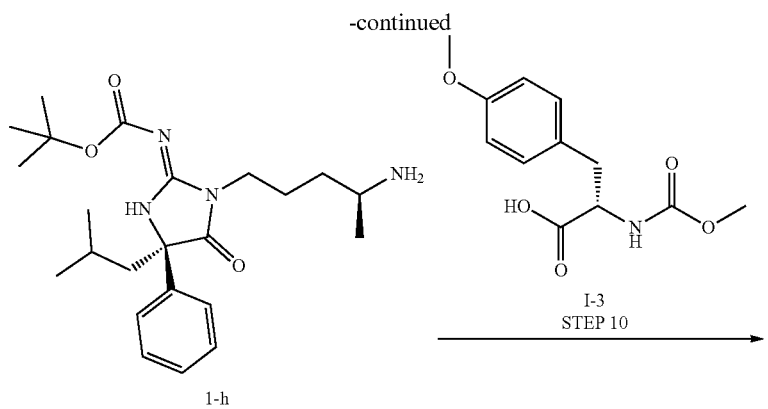

I-3
STEP 10

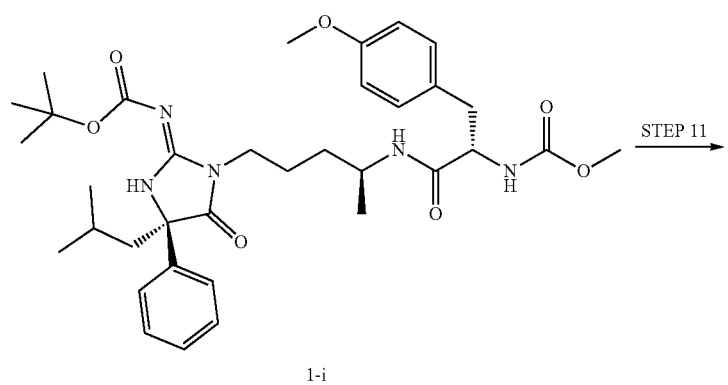

STEP 11

1-i

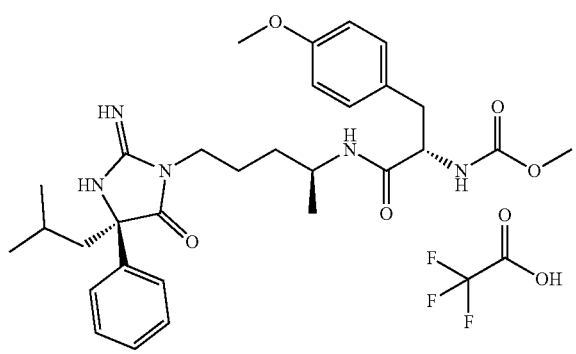

1

Step 1: Methyl 2-(benzylideneamino)-2-phenylacetate (1-a)

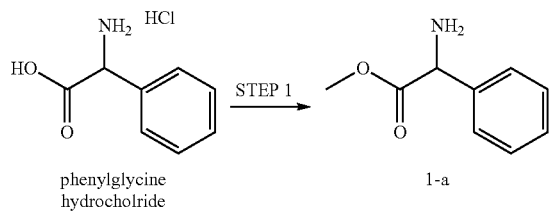

To a cooled solution of phenylglycine hydrochloride (Sigma-Aldrich) (40.3 g, 266.3 mmol) in MeOH (250 ml), was added thionyl chloride (29.0 mL, 399.5 mmol) dropwise. The solution was stirred for 12 h until a colorless solution was obtained. The solvents were evaporated to give a pale yellow solid, more methanol was added to dissolve the solid, and the solution was evaporated to dryness. The solid was placed on a high vacuum pump for 24 h to give 1-a. (53.0 g, 99%). $^1$H NMR (300 MHz, CD$_3$OD) δ 7.51 (d, J=1.2 Hz, 5H), 5.22 (s, 1H), 3.8 (s, 3H).

Step 2: Methyl 2-(benzylideneamino)-2-phenylacetate (1-b)

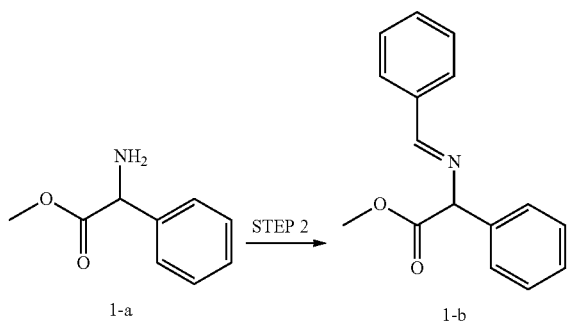 [SMILES: COC(=O)C(N)c1ccccc1 ; COC(=O)C(/N=C/c1ccccc1)c1ccccc1]

To a suspension of methyl 2-amino-2-phenylacetate (1-a) (53.0 g, 263 mmol) in dichloromethane (250 mL) was added Et$_3$N (44.7 mL, 315 mmol) dropwise and stirred for 1 h. Benzaldehyde (27 mL, 263 mmol) was added, and the reaction was stirred for 12 h. Water (50 mL) was added to the reaction mixture which then was transferred to a separatory funnel. The organic layer was washed with brine and dried over Na$_2$SO$_4$, filtered, and concentrated to give an oil which eventually solidified on the high vacuum pump to afford methyl 2-(benzylideneamino)-2-phenylacetate 1-b. $^1$H NMR (300 MHz, CDCl$_3$) δ 10.02 (s, 1H), 7.84-7.79 (m, 2H) 7.53 (d, J=1.5 Hz) 7.5-7.28 (m, 8H), 5.20 (s, 1H), 3.74 (s, 3H).

Step 3: Methyl 2-amino-4-methyl-2-phenylpent-4-enoate (1-c)

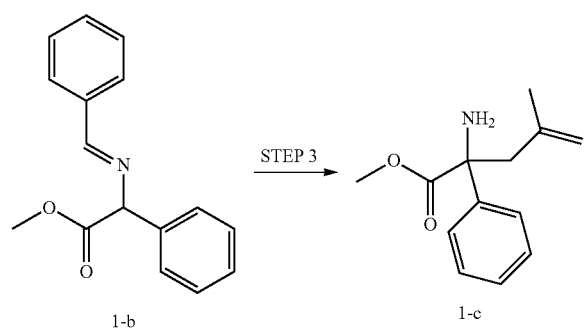 [SMILES: COC(=O)C(/N=C/c1ccccc1)c1ccccc1 ; C=C(C)CC(N)(C(=O)OC)c1ccccc1]

To an oven dried round bottom flask was added methyl 2-(benzylideneamino)-2-phenylacetate 1-b (5.0 g, 19.7 mmol), THF (75 mL), and 3-bromo-2-methylpropene (Sigma-Aldrich) (3.2 g, 23.9 mmol). The mixture was cooled to −78° C. LiHMDS (45 mL, 1M THF solution, 45 mmol) was added dropwise and stirred for 12 h as the reaction mixture warmed to room temperature. The mixture was cooled in an ice bath as 2N HCl (2×30 mL) was added. The mixture was then transferred to a separatory funnel. The aqueous layer was separated and basified to pH 8-10 with 2N NaOH. The mixture was transferred back to the separatory funnel and extracted with EtOAc (3×30 mL). Then the organic portion was dried over Na$_2$SO$_4$, filtered, and concentrated to give an oil. The oil was purified by silica gel chromatography (0-30% EtOAc/Hexanes) to give methyl 2-amino-4-methyl-2-phenylpent-4-enoate 1-c. $^1$H NMR (300 MHz, CDCl$_3$) δ 7.60-7.51 (m, 2H), 7.37-7.27 (m, 3H), 4.93 (t, J=1.6 Hz, 1H), 4.80 (d, J=0.7 Hz, 1H), 3.71 (s, 3H), 3.11 (d, J=13.7 Hz, 1H), 2.69 (d, J=13.3 Hz, 1H), 2.04 (bs, 2H), 1.28 (s, 3H).

Step 4: Methyl 2-amino-4-methyl-2-phenylpentanoate (1-d)

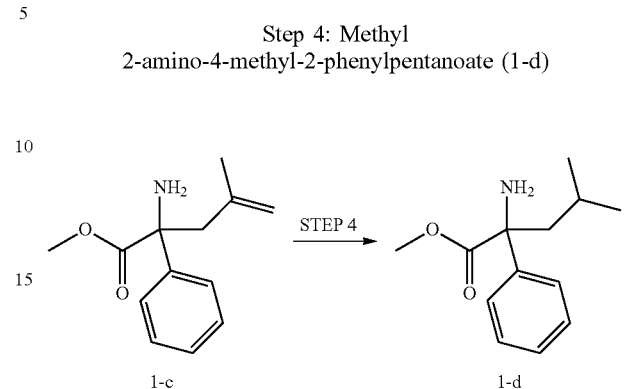

A stirred solution of compound I-c (5.0 g, 19.74 mmol) and 3-bromo-2-methylpropene (Sigma-Aldrich)(1-c)(2.39 mL, 23.69 mmol) in anhydrous THF was cooled to −78° C. To this cooled solution was dropwise added LHMDS. Stir the mixture 24 h allowing the mixture to gradually warm up to room temperature. The mixture was then cooled to 0° C. and acidified with 2N HCl$_{(aq)}$ (2×30 mL). The aqueous portion was then basicified to pH ~8 with 2N NaOH (aq) and further extracted with EtOAc (3×30 mL). The organic portion was dried over MgSO$_4$, filtered, and concentrated in vacuo to afford an oil. This oil was further purified by silica gel chromatography eluting with 0 to 30% EtOAc in Hexanes to produce compound I-d. MS (ESI): m/z=220.3 (M+H).

Step 5: Methyl (R)-2-amino-4-methyl-2-phenylpentanoate (1-dR) and Methyl (S)-2-amino-4-methyl-2-phenylpentanoate (1-dS)

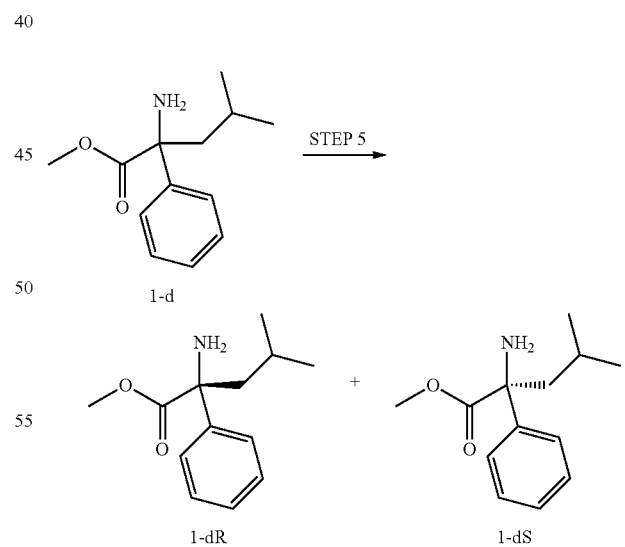

Racemic methyl-2-amino-4-methyl-2-phenylpentanoate (4.2 g) was resolved on a CHIRALPACK® IC column (Daicel Corporation, Chiral Technologies, West Chester, Pa. USA) (10μ, 30×250 mm) eluting with 15% MeOH in CO$_2$ with DEA as the modifier to afford the (R)-isomer as the first eluting peak and the (S)-isomer as the second eluting peak.

Step 6: tert-Butyl (R)-(1-(2,4-dimethoxybenzyl)-4-isobutyl-5-oxo-4-phenylimidazolidin-2-ylidene)carbamate (1-e)

Step 7: tert-Butyl (R)-(4-isobutyl-5-oxo-4-phenylimidazolidin-2-ylidene) carbamate (1-f)

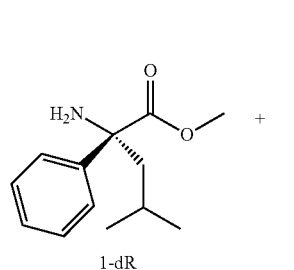

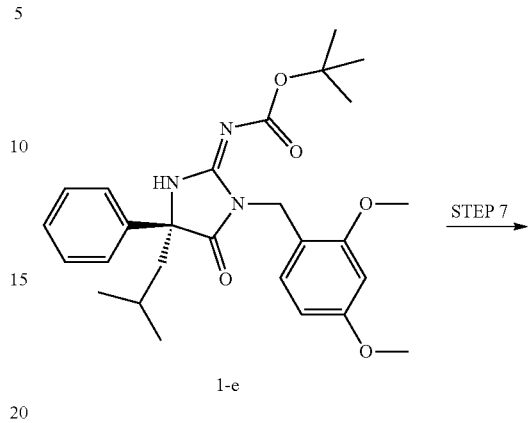

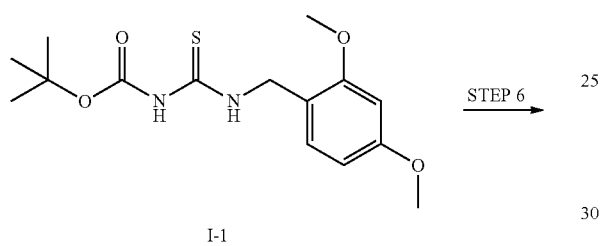

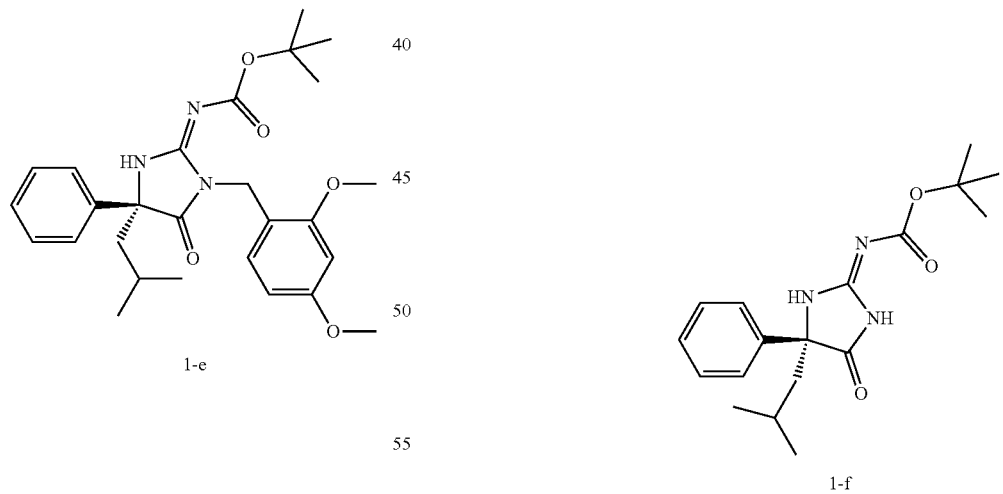

A solution of methyl (R)-2-amino-4-methyl-2-phenylpentanoate (1-dR) (3.3 g, 15 mmol), protected thiourea (I-1)(5.4 g, 16 mmol), EDC (3.3 g, 17 mmol) Hunig's base (3.9 ml, 22 mmol) in DMF (50 ml) were heated at 65° C. overnight. The reaction was cooled to room temperature, diluted with EtOAc, washed with water, brine, dried over $MgSO_4$ and the solvent removed in vacuo. The residue was purified on silica gel eluting with a gradient of 0-20% EtOAc in hexanes to afford compound I-e. MS (ESI): m/z=483.4 (M+H).

tert-Butyl-(R)-(1-(2,4-dimethoxybenzyl)-4-isobutyl-5-oxo-4-phenylimidazolidin-2-ylidene)carbamate (1-e) (4.4 g, 9.2 mmol) and 20% $Pd(OH)_2/C$ (1 g) in MeOH (40 ml) were stirred under a balloon of hydrogen for 2 days. The reaction was purged with nitrogen and filtered. The solvent was removed in vacuo to afford crude compound I-f. MS (ESI): m/z=332.5 (M+H).

Step 8: (9H-Fluoren-9-yl)methyl ((S)-5-((R)-2-((tert-butoxycarbonyl)imino)-4-isobutyl-5-oxo-4-phenylimidazolidin-1-yl)pentan-2-yl)carbamate (1-g)

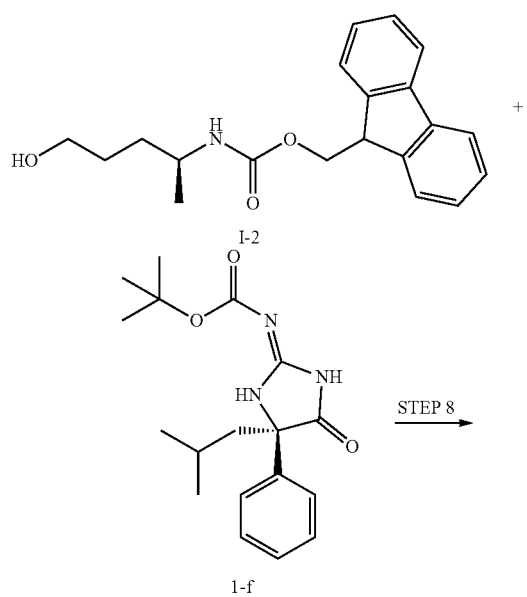

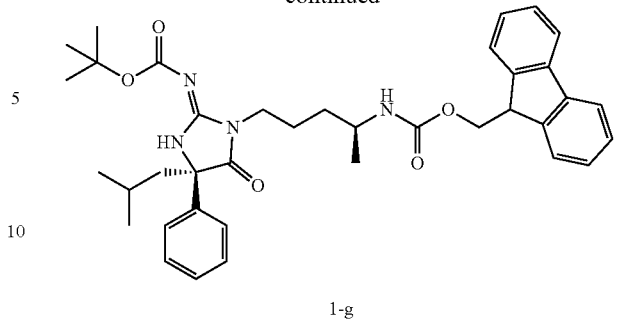

DIAD (0.67 g, 3.1 mmol) was added to a solution of (9H-fluoren-9-yl)methyl (S)-(5-hydroxypentan-2-yl)carbamate (I-2) (0.98 g, 3.0 mmol), tert-butyl (R)-(4-isobutyl-5-oxo-4-phenylimidazolidin-2-ylidene)carbamate (1-f) (1.0 g, 3.0 mmol) and PPh₃ (0.79 g, 3.0 mmol) in CHCl₃ at 50° C. and the reaction stirred at this temperature for 1 h. The solvent was removed in vacuo and the residue was purified on silica gel eluting with a gradient of 0-70% EtOAc in hexanes to afford compound I-g.

Step 9: tert-Butyl ((R)-1-((S)-4-aminopentyl)-4-isobutyl-5-oxo-4-phenylimidazolidin-2-ylidene)carbamate (1-h)

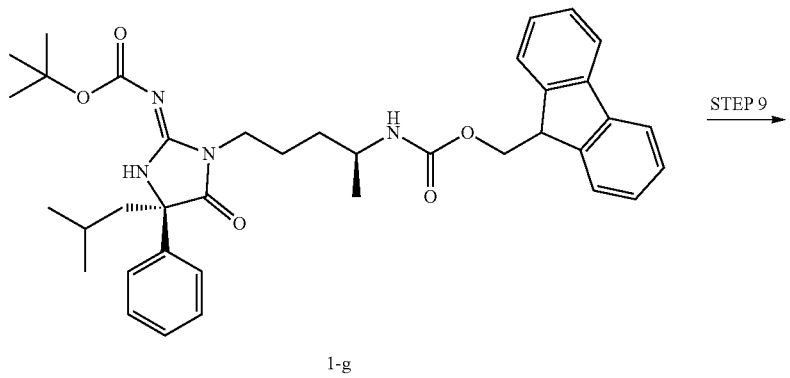

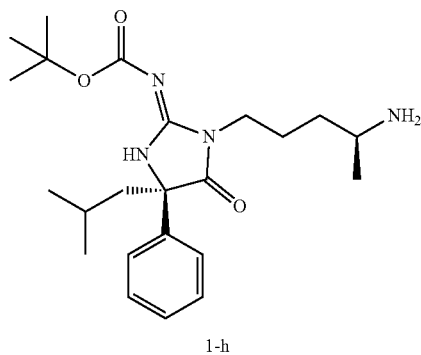

A solution of (9H-fluoren-9-yl)methyl ((S)-5-((R)-2-((tert-butoxycarbonyl)imino)-4-isobutyl-5-oxo-4-phenylimidazolidin-1-yl)pentan-2-yl)carbamate (1-g) (0.79 g, 1.2 mmol) and diethylamine (5 ml) in CH₃CN (15 ml) was stirred at room temperature for 1.5 h. The solvent was removed in vacuo and the material, 1-h, taken on crude to the next reaction.

Step 10: tert-Butyl ((R)-4-isobutyl-1-((S)-4-((S)-2-((methoxycarbonyl)amino)-3-(4-methoxyphenyl) propanamido)pentyl)-5-oxo-4-phenylimidazolidin-2-ylidene)carbamate (1-i)

0.18 mmol) and (S)-2-((methoxycarbonyl)amino)-3-(4-methoxyphenyl)propanoic acid (1-3) (30 mg, 0.12 mmol) in DMF (1 ml) and the resulting reaction stirred at room temperature for 3 hours. The reaction was diluted with EtOAc, washed with water and brine, dried over MgSO₄ and the solvent removed in vacuo. The residue was purified on silica gel eluting with a gradient of 0-70% EtOAc in hexanes to afford compound I-i. MS (ESI): m/z=653.6 (M+H).

Step 11: Methyl ((S)-1-(((S)-5-((R)-2-imino-4-isobutyl-5-oxo-4-phenylimidazolidin-1-yl)pentan-2-yl)amino)-3-(4-methoxyphenyl)-1-oxopropan-2-yl) carbamate 2,2,2-trifluoroacetate, (Compound 1)

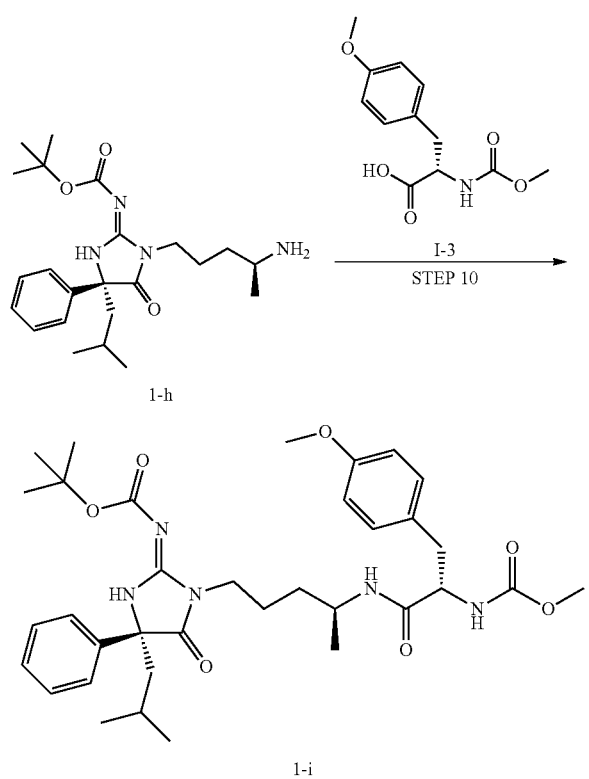

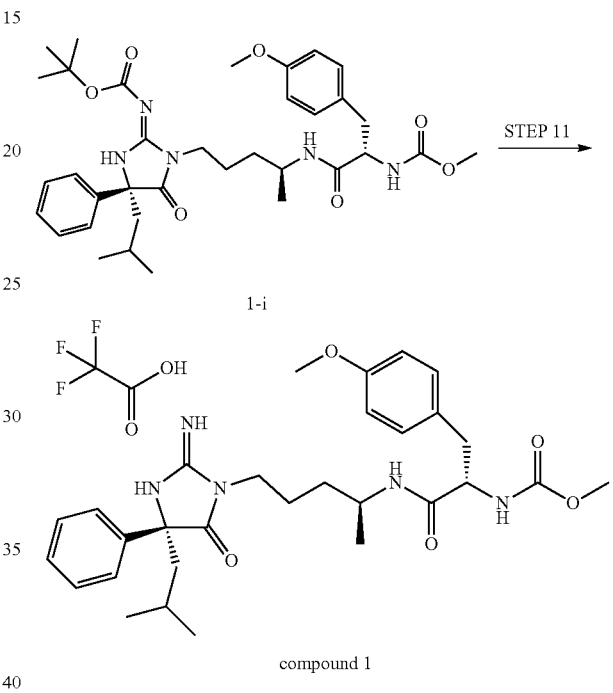

compound 1

TEA (34 mL, 0.24 mmol) was added to a solution of tert-butyl ((R)-4-isobutyl-1-((S)-4-((S)-2-((methoxycarbonyl)amino)-3-(4-methoxyphenyl)propanamido)pentyl)-5-oxo-4-phenylimidazolidin-2-ylidene)carbamate (1-h) (50 mg, 0.12 mmol), EDC (35 mg, 0.18 mmol), HOAt (25 mg, TFA (1 ml) was added to a solution of methyl ((S)-1-(((S)-5-((R)-2-((tert-butoxycarbonyl)imino)-4-isobutyl-5-oxo-4-phenylimidazolidin-1-yl)pentan-2-yl)amino)-3-(4-methoxyphenyl)-1-oxopropan-2-yl)carbamate (1-i) (33 mg, 0.051 mmol) in DCM (1 ml) and the reaction stirred at room temperature for 30 min. The solvent was removed in vacuo to afford compound 1. HRMS calcd for (M+1)+m/z 552.3180, found m/z 552.3177.

Example 2

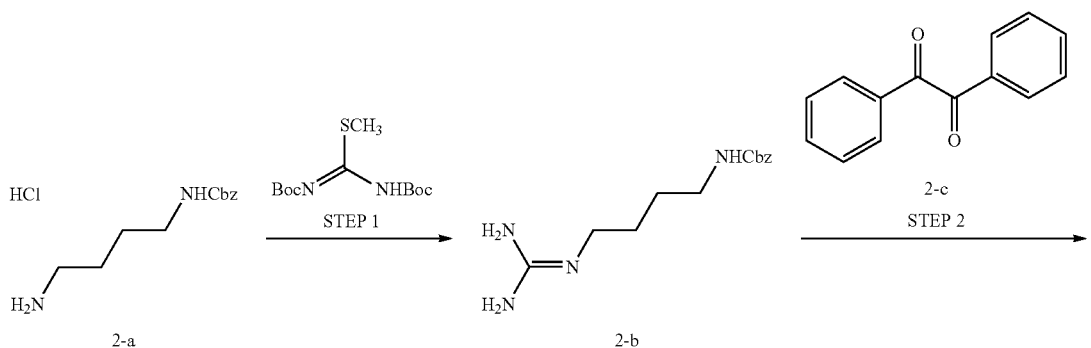

-continued
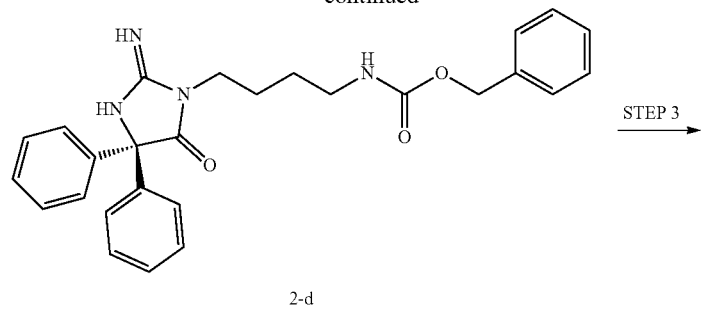
2-d
STEP 3
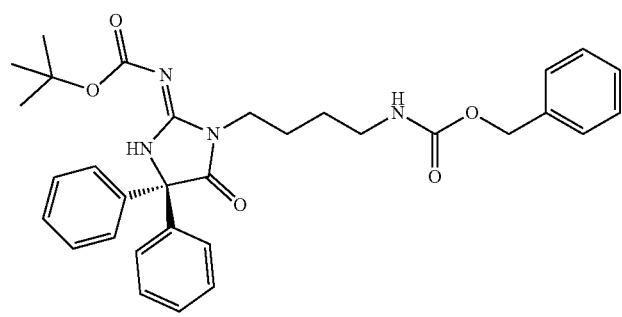
2-e
2-e → STEP 4 →
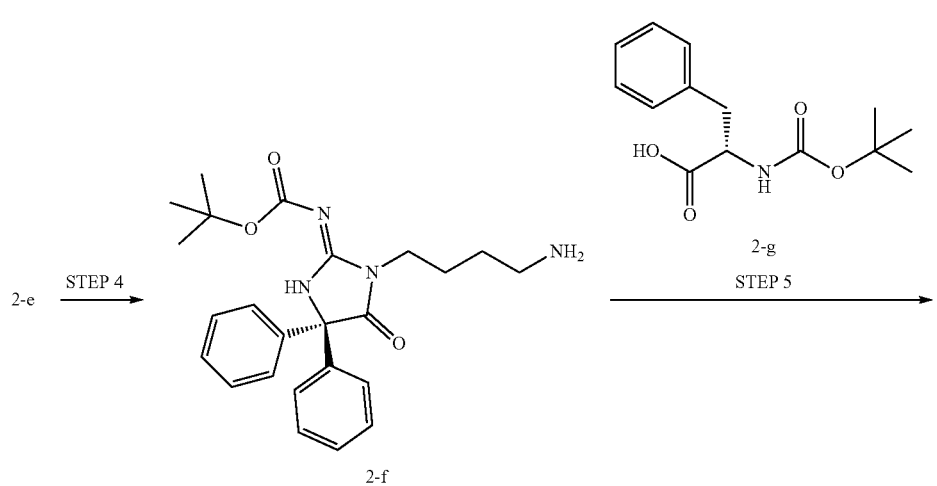
2-f
2-g
STEP 5
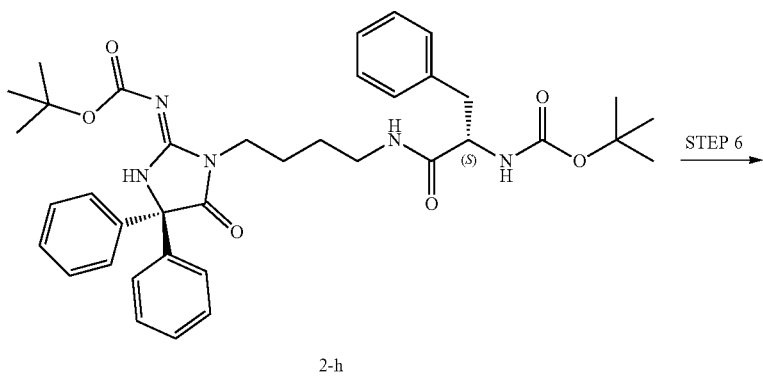
2-h
STEP 6

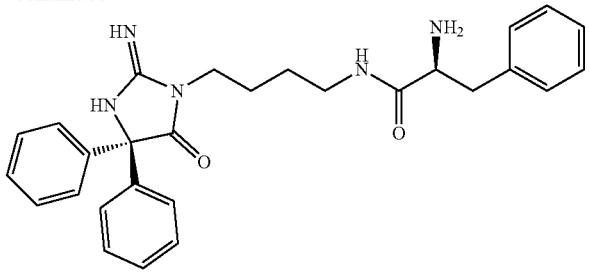

compound 2

Step 1: Benzyl (4-((diaminomethylene)amino)butyl)carbamate (2-b)

Step 2: Benzyl (4-(2-imino-5-oxo-4,4-diphenylimidazolidin-1-yl)butyl)carbamate (2-d)

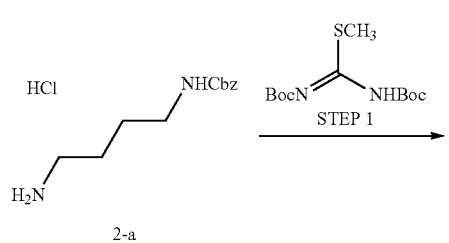

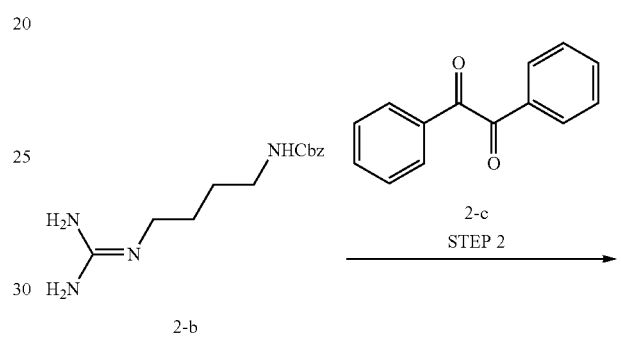

A solution and N-carbobenzoxy-1,4-diaminobutane hydrochloride (2-a) (TCI-US) (2.58 g, 9.99 mmol) in DMF (25 mL) was treated with TEA (2.8 mL) and N,N'-bis(tert-butoxycarbonyl)-S-methylisothiourea (Fluorochem) (2.9 g, 9.99 mmol) was stirred at room temperature for 2 h. The solvent was removed in vacuo and the resultant residue further purified by silca gel chromatography eluting with 20% EtOAc in hexanes to provide N',N''-bis(tert-butoxycarbonyl)-N-carbobenzoxy-1,4-diaminobutane. A solution of the intermediate N',N''-bis(tert-butoxycarbonyl)-N-carbobenzoxy-1,4-diaminobutane (1.55 g, 3.34 mmol) in DCM (10 mL) was treated with TFA (10 mL) and stirred at room temperature for 2 h. The solvents were removed under reduced pressure to afford 2-b. MS (ESI): m/z=265 (M+H).

A solution of benzil (Sigma-Aldrich) (2-c) (0.8 g, 3.8 mmol), benzyl (4-((diaminomethylene)amino)butyl)carbamate (2-b) (1.68 g, 6.4 mmol) and triethylamine (2 ml, 15.9 mmol) in ethanol (25 mL) was heated to 80° C. for 20 h. The solvent was removed in vacuo to afford a residue which was partitioned between DCM and 1N HCl. The organic portion was collected, dried over MgSO₄, and the solvent removed in vacuo. The residue was purified on silica gel eluting with 5% MeOH in DCM to afford compound 2-d. MS (ESI): m/z=457 (M+H).

Step 3: Benzyl(4-(2-((tert-butoxycarbonyl)imino)-5-oxo-4,4-diphenylimidazolidin-1-yl)butyl)carbamate (2-e)

Step 4: tert-Butyl (1-(4-aminobutyl)-5-oxo-4,4-diphenylimidazolidin-2-ylidene)carbamate (2-f)

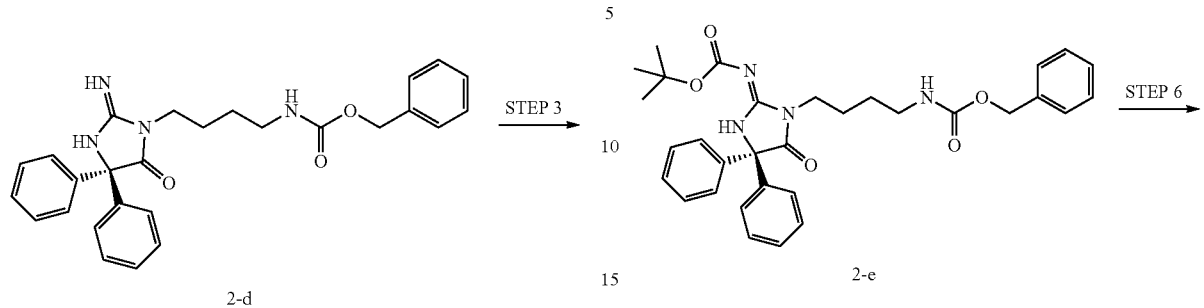

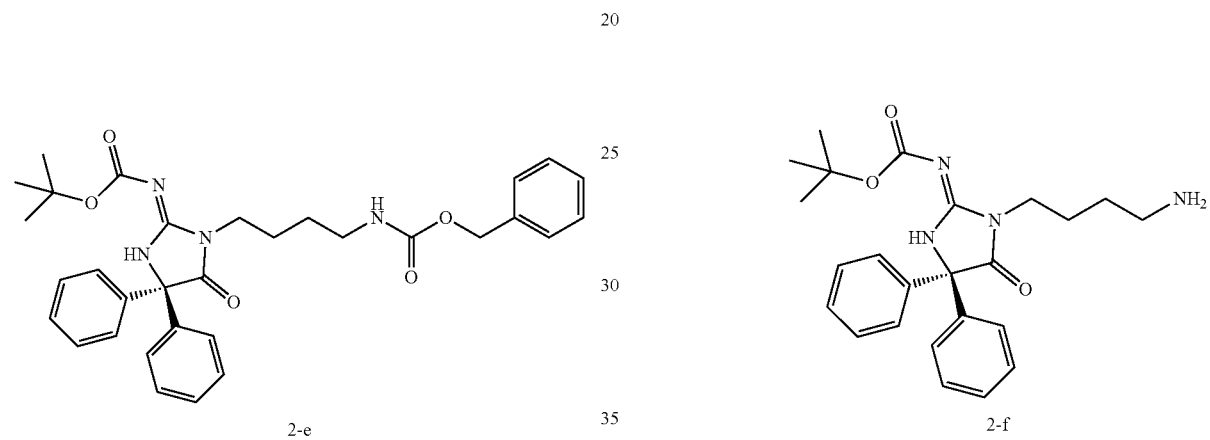

A solution of benzyl (4-(2-imino-5-oxo-4,4-diphenylimidazolidin-1-yl)butyl)carbamate (2-d) (1.35 g, 3.0 mmol), di-tert-butyl dicarbonate (0.71 g, 3.25 mmol), DIEA (0.57 mL, 3.27 mmol) in DCM (20 mL) was stirred at room temperature for 24 h. The reaction was diluted with DCM, washed with 1N HCl aq., dried over MgSO$_4$ and the solvent removed in vacuo. The residue was purified on silica gel eluting 2% MeOH in DCM to afford compound 2-e. MS (ESI): m/z=557 (M+H).

A solution of benzyl(4-(2-((tert-butoxycarbonyl)imino)-5-oxo-4,4-diphenylimidazolidin-1-yl)butyl)carbamate (2-e) (1.09 g, 2.4 mmol), and 20% Pd(OH)$_2$/C (0.6 g, 0.85 mmol) in EtOH (40 mL) was placed under atmospheric hydrogen and stirred at room temperature for 4 h. The reaction was filtered and the solvent removed in vacuo to afford compound 2-f. MS (ESI): m/z=423 (M+H).

Step 5: tert-butyl (S)-(1-(4-(2-((tert-butoxycarbonyl)amino)-3-phenylpropanamido)butyl)-5-oxo-4,4-diphenylimidazolidin-2-ylidene)carbamate (2-h)

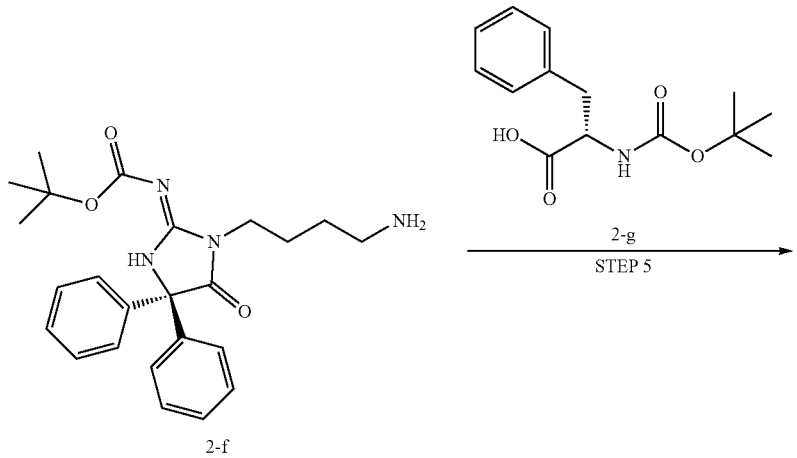

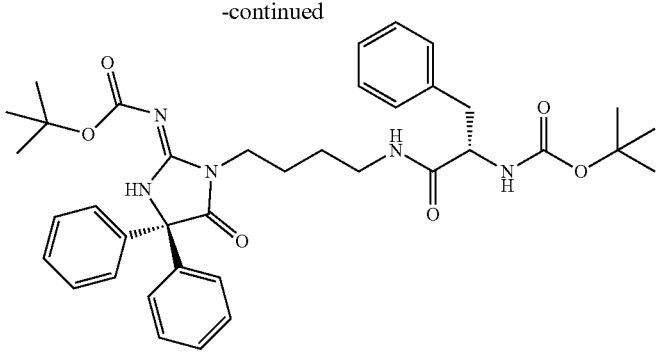

2-h

A solution of tert-butyl (1-(4-aminobutyl)-5-oxo-4,4-diphenylimidazolidin-2-ylidene)carbamate (2-h) (69 mg, 0.16 mmol), HOBt (39 mg, 0.29 mmol), (tert-butoxycarbonyl)-L-phenylalanine (Sigma-Aldrich) (2-g) (68 mg, 0.26 mmol), resin-bound EDC (500 mg, loading density 1.19 mmol/g, 0.60 mmol), and resin-bound DIEA (400 mg, loading density 3.51 mmol/g, 1.40 mmol) in acetonitrile (8 mL) and THF (4 mL) was stirred at room temperature for 66 h. To this mixture was added acetonitrile (5 mL), resin-bound isocyanate (220 mg, loading density 1.46 mmol/g, 0.32 mmol), and resin-bound trisamine (320 mg, loading density 4.46 mmol/g, 1.43 mmol), and the reaction was agitated an additional 24 h. The reaction mixture was filtered, washed with acetonitrile, and the solvent removed in vacuo. The residue was purified on silica gel eluting 5% MeOH in DCM to afford compound 2-h. MS (ESI): m/z=670 (M+H).

Step 6: (S)-2-amino-N-(4-(2-imino-5-oxo-4,4-diphenylimidazolidin-1-yl)butyl)-3-phenylpropanamide (Compound 2)

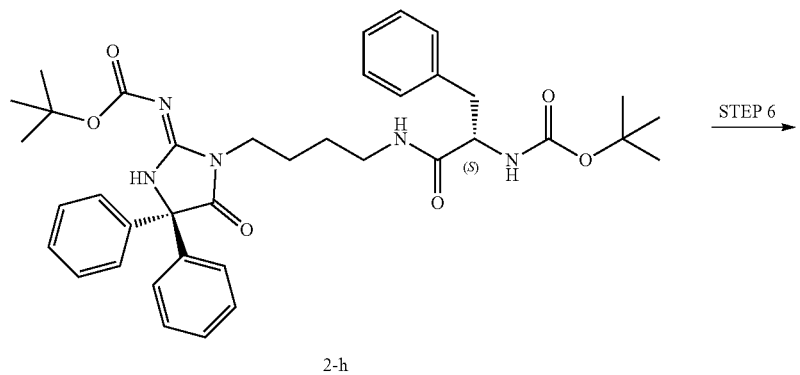

2-h

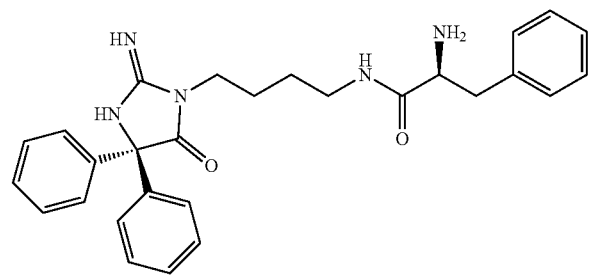

compound 2

Trifluoroacetic acid (1.2 ml, 87 mmol) was added to a solution of tert-butyl (S)-(1-(4-(2-((tert-butoxycarbonyl)amino)-3-phenylpropanamido)butyl)-5-oxo-4,4-diphenylimidazolidin-2-ylidene)carbamate (2-h) (60 mg, 0.090 mmol) in DCM (1.2 ml) and the reaction was stirred at room temperature for 1 h. The mixture was diluted with MeOH (5 mL) and DCM (5 mL). To this solution was added resin-bound TsOH (0.90 g, loading density 4.13 mmol/g, 3.72 mmol), and the mixture was stirred at room temperature for 3 h. The reaction mixture was filtered, and the resin washed with DCM/MeOH, then MeOH, then eluted with 7N ammonia in MeOH solution. The ammonia-methanol solution was removed in vacuo to afford compound 2. MS (ESI): m/z=470 (M+H).

Table 1 provides structures for compounds 1 through 56 which were synthesized directly by the methods described above or by analogous methods to those described above.

TABLE 1

| Compound | Structure | Compound Name | Exact Mass [M + H]+ |
|---|---|---|---|
| 1 | 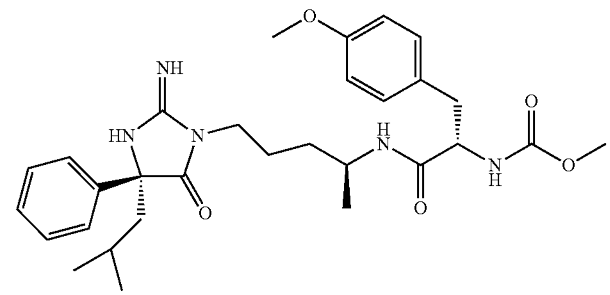 [SMILES: COC(=O)N[C@@H](Cc1ccc(OC)cc1)C(=O)N[C@@H](C)CCCN1C(=N)N[C@](CC(C)C)(c2ccccc2)C1=O] | N-{(1S)-4-[(4R)-2-imino-4-(2-methylpropyl)-5-oxo-4-phenylimidazolidin-1-yl]-1-methylbutyl}-N-alpha-(methoxycarbonyl)-O-methyl-L-tyrosinamide | 552.3 |
| 2 | 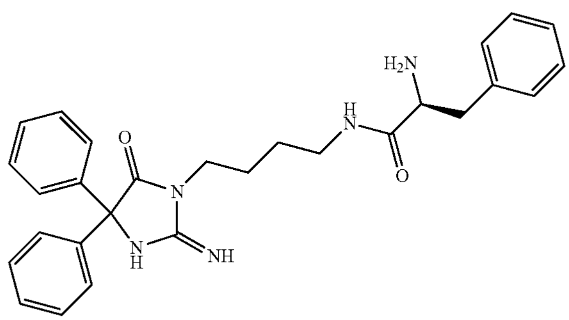 | N-[4-(2-imino-5-oxo-4,4-diphenylimidazolidin-1-yl)butyl]-L-phenylalaninamide | 470.3 |
| 3 | 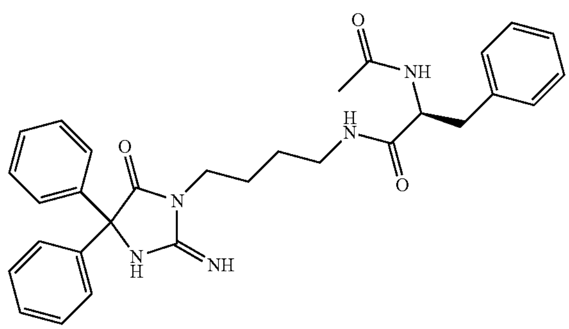 [SMILES: CC(=O)N[C@@H](Cc1ccccc1)C(=O)NCCCCN1C(=N)NC(c2ccccc2)(c2ccccc2)C1=O] | N-alpha-acetyl-N-[4-(2-imino-5-oxo-4,4-diphenylimidazolidin-1-yl)butyl]-L-phenylalaninamide | 512.3 |
| 4 | 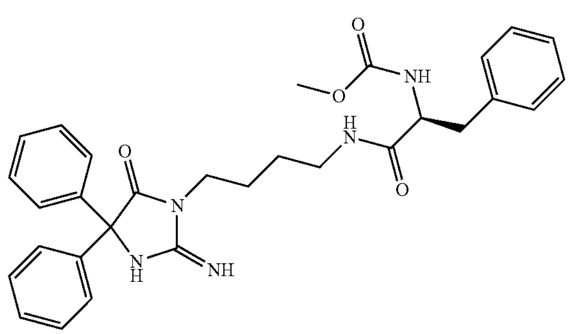 [SMILES: COC(=O)N[C@@H](Cc1ccccc1)C(=O)NCCCCN1C(=N)NC(c2ccccc2)(c2ccccc2)C1=O] | N-[4-(2-imino-5-oxo-4,4-diphenylimidazolidin-1-yl)butyl]-N-alpha-(methoxycarbonyl)-L-phenylalaninamide | 528.3 |

TABLE 1-continued

| Compound | Structure | Compound Name | Exact Mass [M + H]+ |
|---|---|---|---|
| 5 | 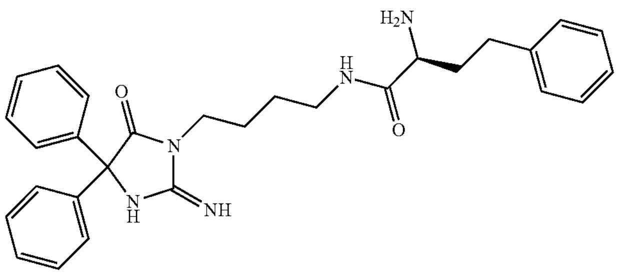 [SMILES: N=C1NC(c2ccccc2)(c2ccccc2)C(=O)N1CCCCNC(=O)[C@@H](N)CCc1ccccc1] | (2S)-2-amino-N-[4-(2-imino-5-oxo-4,4-diphenylimidazolidin-1-yl)butyl]-4-phenylbutanamide | 484.3 |
| 6 | 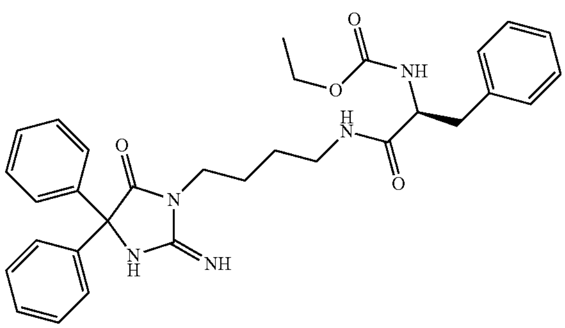 [SMILES: CCOC(=O)N[C@@H](Cc1ccccc1)C(=O)NCCCCN1C(=N)NC(c2ccccc2)(c2ccccc2)C1=O] | N-alpha-(ethoxycarbonyl)-N-[4-(2-imino-5-oxo-4,4-diphenylimidazolidin-1-yl)butyl]-L-phenylalaninamide | 542.3 |
| 7 | 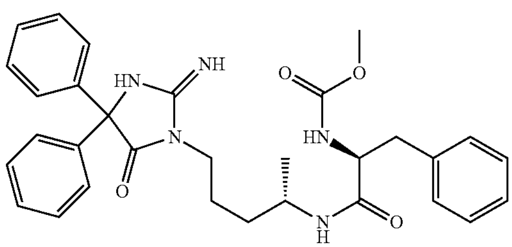 [SMILES: COC(=O)N[C@@H](Cc1ccccc1)C(=O)N[C@@H](C)CCCN1C(=N)NC(c2ccccc2)(c2ccccc2)C1=O] | N-[(1S)-4-(2-imino-5-oxo-4,4-diphenylimidazolidin-1-yl)-1-methylbutyl]-N-alpha-(methoxycarbonyl)-L-phenylalaninamide | 542.3 |
| 8 | 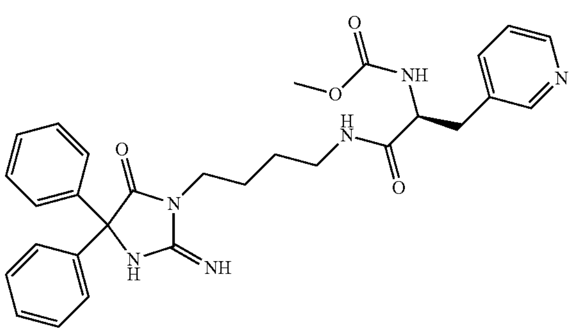 [SMILES: COC(=O)N[C@@H](Cc1cccnc1)C(=O)NCCCCN1C(=N)NC(c2ccccc2)(c2ccccc2)C1=O] | methyl [(1S)-2-{[4-(2-imino-5-oxo-4,4-diphenylimidazolidin-1-yl)butyl]amino}-2-oxo-1-(pyridin-3-ylmethyl)ethyl]carbamate | 529.3 |
| 9 | 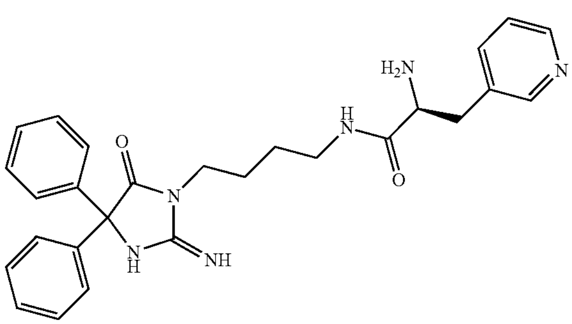 [SMILES: N=C1NC(c2ccccc2)(c2ccccc2)C(=O)N1CCCCNC(=O)[C@@H](N)Cc1cccnc1] | N-[4-(2-imino-5-oxo-4,4-diphenylimidazolidin-1-yl)butyl]-3-pyridin-3-yl-L-alaninamide | 471.3 |

TABLE 1-continued

| Compound | Structure | Compound Name | Exact Mass [M + H]+ |
|---|---|---|---|
| 10 | 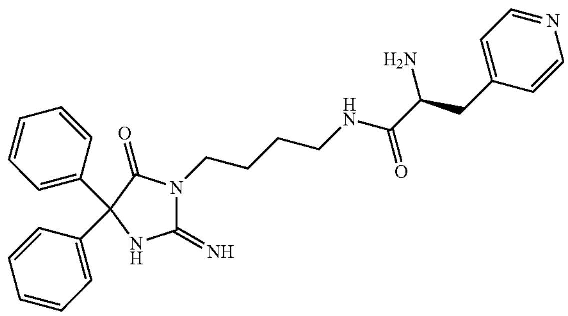 [SMILES: N=C1NC(c2ccccc2)(c2ccccc2)C(=O)N1CCCCNC(=O)[C@@H](N)Cc1ccncc1] | N-[4-(2-imino-5-oxo-4,4-diphenylimidazolidin-1-yl)butyl]-3-pyridin-4-yl-L-alaninamide | 471.3 |
| 11 | 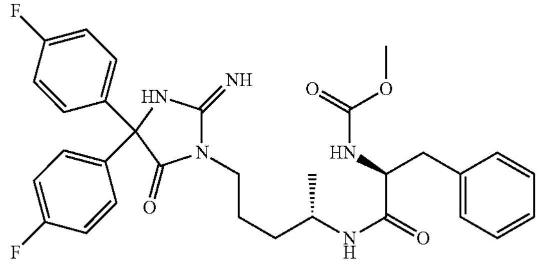 [SMILES: COC(=O)N[C@@H](Cc1ccccc1)C(=O)N[C@@H](C)CCCN1C(=N)NC(c2ccc(F)cc2)(c2ccc(F)cc2)C1=O] | N-{(1S)-4-[4,4-bis(4-fluorophenyl)-2-imino-5-oxoimidazolidin-1-yl]-1-methylbutyl}-N-alpha-(methoxycarbonyl)-L-phenylalaninamide | 578.3 |
| 12 | 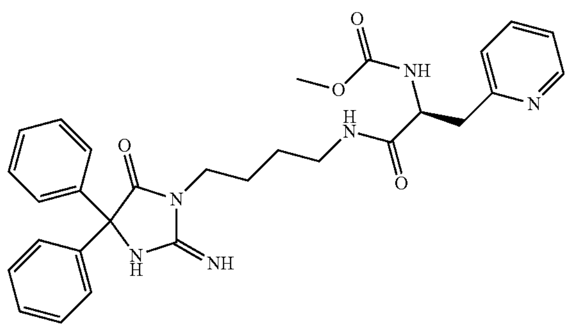 [SMILES: COC(=O)N[C@@H](Cc1ccccn1)C(=O)NCCCCN1C(=N)NC(c2ccccc2)(c2ccccc2)C1=O] | methyl [(1S)-2-{[4-(2-imino-5-oxo-4,4-diphenylimidazolidin-1-yl)butyl]amino}-2-oxo-1-(pyridin-2-ylmethyl)ethyl]carbamate | 529.3 |
| 13 | 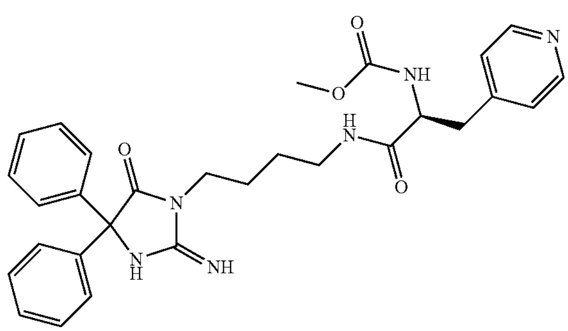 [SMILES: COC(=O)N[C@@H](Cc1ccncc1)C(=O)NCCCCN1C(=N)NC(c2ccccc2)(c2ccccc2)C1=O] | methyl [(1S)-2-{[4-(2-imino-5-oxo-4,4-diphenylimidazolidin-1-yl)butyl]amino}-2-oxo-1-(pyridin-4-ylmethyl)ethyl]carbamate | 529.3 |
| 14 | 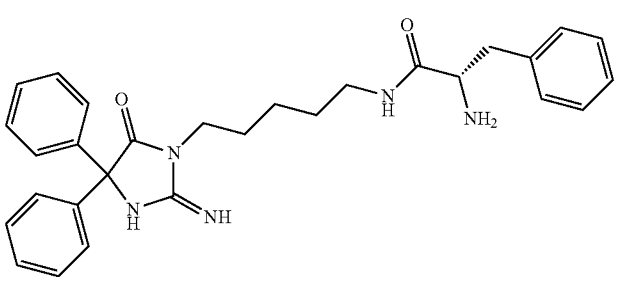 [SMILES: N=C1NC(c2ccccc2)(c2ccccc2)C(=O)N1CCCCCNC(=O)[C@@H](N)Cc1ccccc1] | N-[5-(2-imino-5-oxo-4,4-diphenylimidazolidin-1-yl)pentyl]-L-phenylalaninamide | 484.3 |

TABLE 1-continued

| Compound | Structure | Compound Name | Exact Mass [M + H]+ |
|---|---|---|---|
| 15 | 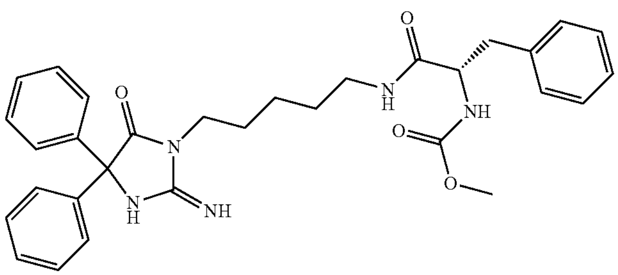 [SMILES: COC(=O)N[C@@H](Cc1ccccc1)C(=O)NCCCCCN1C(=N)NC(c2ccccc2)(c2ccccc2)C1=O] | N-[5-(2-imino-5-oxo-4,4-diphenylimidazolidin-1-yl)pentyl]-N-alpha-(methoxycarbonyl)-L-phenylalaninamide | 542.3 |
| 16 | 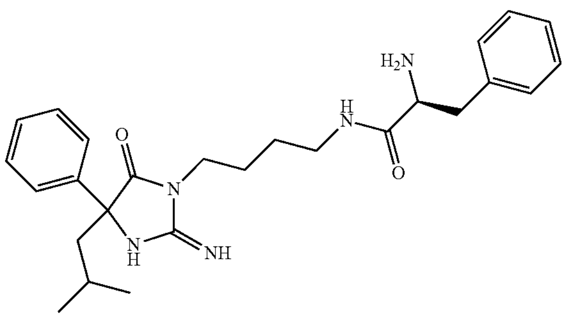 [SMILES: CC(C)CC1(c2ccccc2)NC(=N)N(CCCCNC(=O)[C@@H](N)Cc2ccccc2)C1=O] | N-{4-[2-imino-4-(2-methylpropyl)-5-oxo-4-phenylimidazolidin-1-yl]butyl}-L-phenylalaninamide | 450.3 |
| 17 | 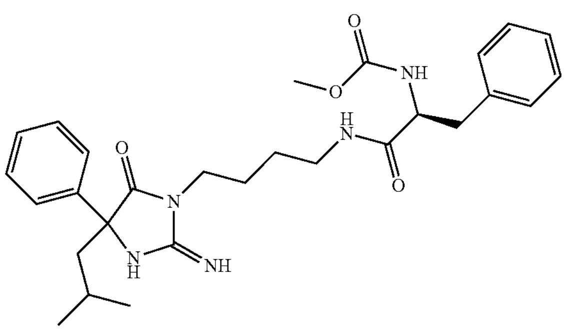 [SMILES: COC(=O)N[C@@H](Cc1ccccc1)C(=O)NCCCCN1C(=N)NC(CC(C)C)(c2ccccc2)C1=O] | N-{4-[2-imino-4-(2-methylpropyl)-5-oxo-4-phenylimidazolidin-1-yl]butyl}-N-alpha-(methoxycarbonyl)-L-phenylalaninamide | 508.3 |
| 18 | 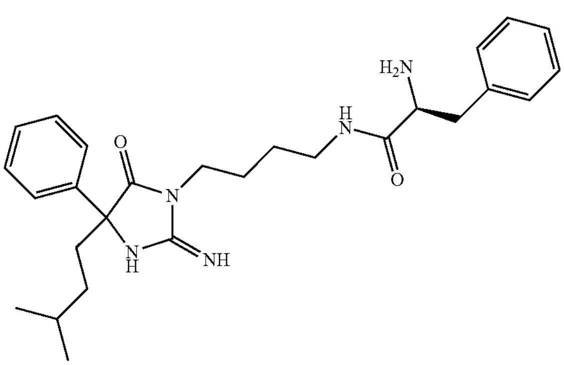 [SMILES: CC(C)CCC1(c2ccccc2)NC(=N)N(CCCCNC(=O)[C@@H](N)Cc2ccccc2)C1=O] | N-{4-[2-imino-4-(3-methylbutyl)-5-oxo-4-phenylimidazolidin-1-yl]butyl}-L-phenylalaninamide | 464.3 |

TABLE 1-continued

| Compound | Structure | Compound Name | Exact Mass [M + H]+ |
|---|---|---|---|
| 19 | 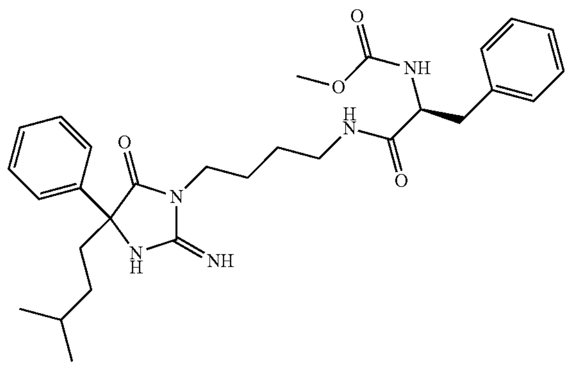 [SMILES: COC(=O)N[C@@H](Cc1ccccc1)C(=O)NCCCCN1C(=N)NC(CCC(C)C)(c2ccccc2)C1=O] | N-{4-[2-imino-4-(3-methylbutyl)-5-oxo-4-phenylimidazolidin-1-yl]butyl}-N-alpha-(methoxycarbonyl)-L-phenylalaninamide | 522.3 |
| 20 | 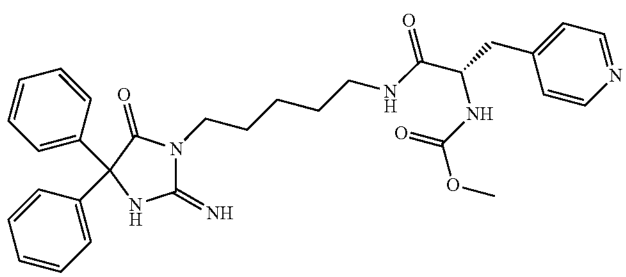 [SMILES: COC(=O)N[C@@H](Cc1ccncc1)C(=O)NCCCCCN1C(=N)NC(c2ccccc2)(c2ccccc2)C1=O] | methyl [(1S)-2-{[5-(2-imino-5-oxo-4,4-diphenylimidazolidin-1-yl)pentyl]amino}-2-oxo-1-(pyridin-4-ylmethyl)ethyl]carbamate | 543.3 |
| 21 | 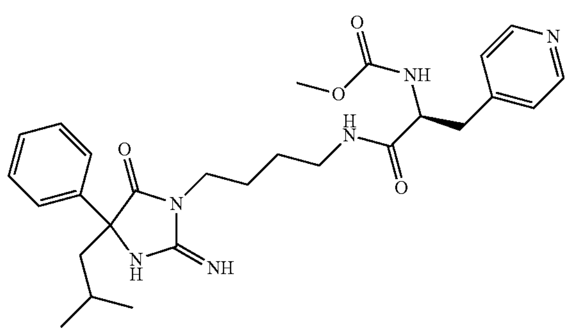 [SMILES: COC(=O)N[C@@H](Cc1ccncc1)C(=O)NCCCCN1C(=N)NC(CC(C)C)(c2ccccc2)C1=O] | methyl [(1S)-2-({4-[2-imino-4-(2-methylpropyl)-5-oxo-4-phenylimidazolidin-1-yl]butyl}amino)-2-oxo-1-(pyridin-4-ylmethyl)ethyl]carbamate | 509.3 |
| 22 | 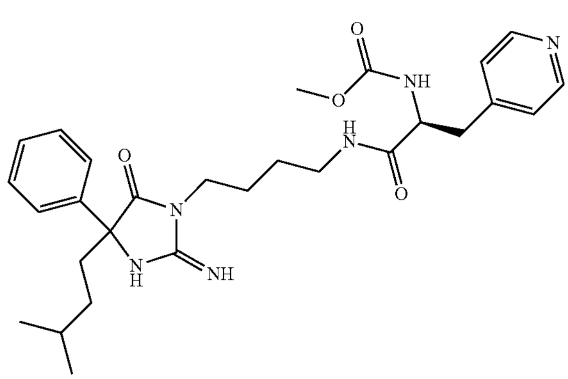 | methyl [(1S)-2-({4-[2-imino-4-(3-methylbutyl)-5-oxo-4-phenylimidazolidin-1-yl]butyl}amino)-2-oxo-1-(pyridin-4-ylmethyl)ethyl]carbamate | 523.3 |

TABLE 1-continued

| Compound | Structure | Compound Name | Exact Mass [M + H]+ |
|---|---|---|---|
| 23 | 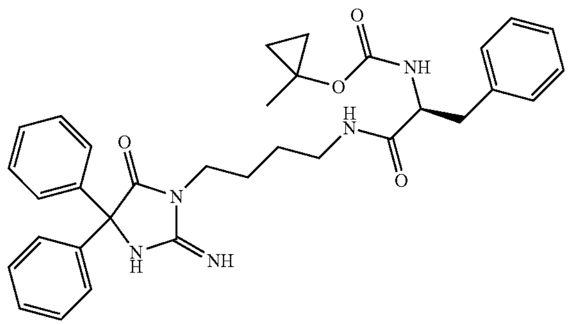 [SMILES: CC1(OC(=O)N[C@@H](Cc2ccccc2)C(=O)NCCCCN2C(=N)NC(c3ccccc3)(c3ccccc3)C2=O)CC1] | N-[4-(2-imino-5-oxo-4,4-diphenylimidazolidin-1-yl)butyl]-N-alpha-{[(1-methylcyclopropyl)oxy]carbonyl}-L-phenylalaninamide | 568.3 |
| 24 | 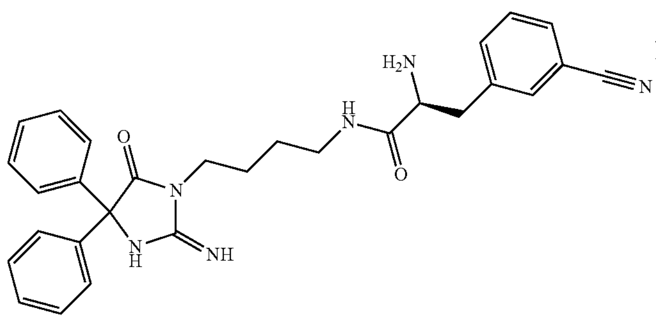 [SMILES: N#Cc1cccc(C[C@H](N)C(=O)NCCCCN2C(=N)NC(c3ccccc3)(c3ccccc3)C2=O)c1] | 3-cyano-N-[4-(2-imino-5-oxo-4,4-diphenylimidazolidin-1-yl)butyl]-L-phenylalaninamide | 495.3 |
| 25 | 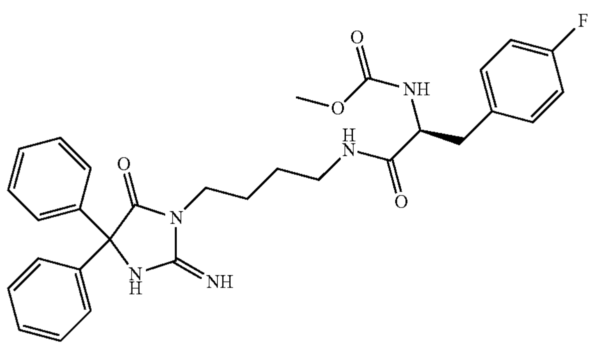 [SMILES: COC(=O)N[C@@H](Cc1ccc(F)cc1)C(=O)NCCCCN1C(=N)NC(c2ccccc2)(c2ccccc2)C1=O] | 4-fluoro-N-[4-(2-imino-5-oxo-4,4-diphenylimidazolidin-1-yl)butyl]-N-alpha-(methoxycarbonyl)-L-phenylalaninamide | 546.3 |
| 26 | 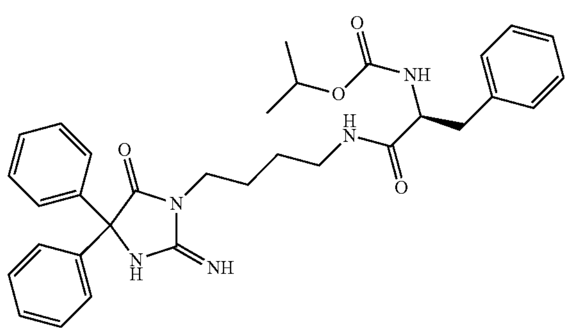 [SMILES: CC(C)OC(=O)N[C@@H](Cc1ccccc1)C(=O)NCCCCN1C(=N)NC(c2ccccc2)(c2ccccc2)C1=O] | N-[4-(2-imino-5-oxo-4,4-diphenylimidazolidin-1-yl)butyl]-N-alpha-[(1-methylethoxy)carbonyl]-L-phenylalaninamide | 556.3 |
| 27 | 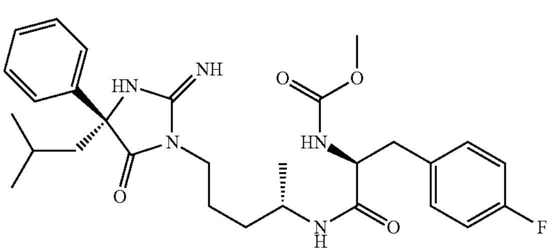 [SMILES: COC(=O)N[C@@H](Cc1ccc(F)cc1)C(=O)N[C@@H](C)CCCN1C(=N)N[C@](CC(C)C)(c2ccccc2)C1=O] | 4-fluoro-N-{(1S)-4-[(4R)-2-imino-4-(2-methylpropyl)-5-oxo-4-phenylimidazolidin-1-yl]-1-methylbutyl}-N-alpha-(methoxycarbonyl)-L-phenylalaninamide | 540.3 |

TABLE 1-continued

| Compound | Structure | Compound Name | Exact Mass [M + H]+ |
|---|---|---|---|
| 28 | 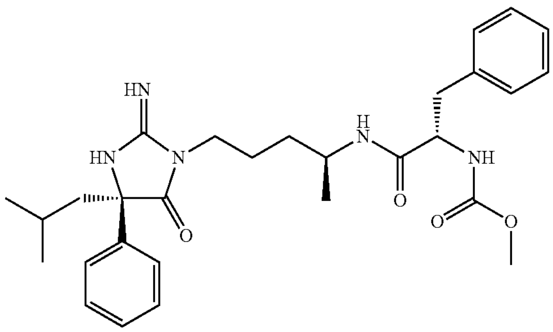 [SMILES: COC(=O)N[C@@H](Cc1ccccc1)C(=O)N[C@@H](C)CCCN1C(=N)N[C@](CC(C)C)(c2ccccc2)C1=O] | N-{(1S)-4-[(4R)-2-imino-4-(2-methylpropyl)-5-oxo-4-phenylimidazolidin-1-yl]-1-methylbutyl}-N-alpha-(methoxycarbonyl)-L-phenylalaninamide | 522.3 |
| 29 | 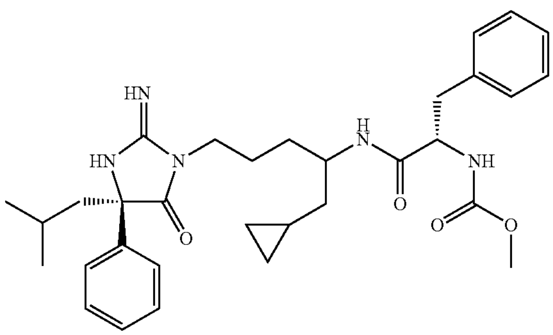 [SMILES: COC(=O)N[C@@H](Cc1ccccc1)C(=O)NC(CCCN1C(=N)N[C@](CC(C)C)(c2ccccc2)C1=O)CC1CC1] | N-{1-(cyclopropylmethyl)-4-[(4R)-2-imino-4-(2-methylpropyl)-5-oxo-4-phenylimidazolidin-1-yl]butyl}-N-alpha-(methoxycarbonyl)-L-phenylalaninamide | 562.3 |
| 30 | 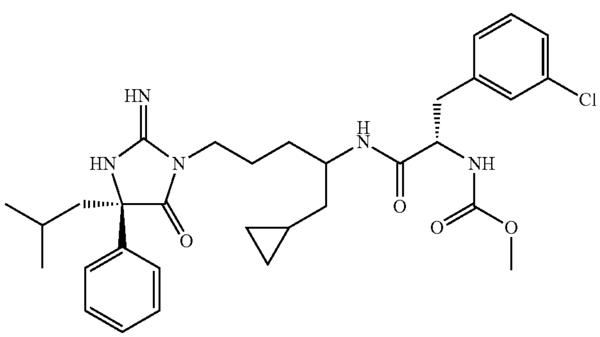 [SMILES: COC(=O)N[C@@H](Cc1cccc(Cl)c1)C(=O)NC(CCCN1C(=N)N[C@](CC(C)C)(c2ccccc2)C1=O)CC1CC1] | 3-chloro-N-{1-(cyclopropylmethyl)-4-[(4R)-2-imino-4-(2-methylpropyl)-5-oxo-4-phenylimidazolidin-1-yl]butyl}-N-alpha-(methoxycarbonyl)-L-phenylalaninamide | 596.3 |
| 31 | 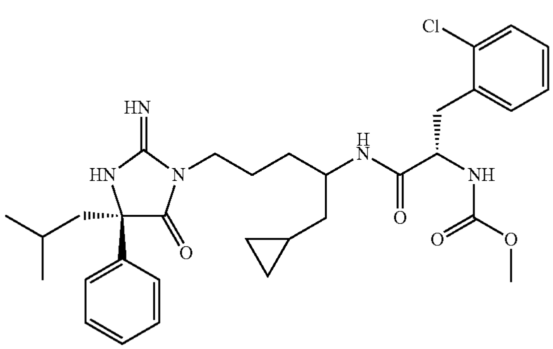 [SMILES: COC(=O)N[C@@H](Cc1ccccc1Cl)C(=O)NC(CCCN1C(=N)N[C@](CC(C)C)(c2ccccc2)C1=O)CC1CC1] | 2-chloro-N-{1-(cyclopropylmethyl)-4-[(4R)-2-imino-4-(2-methylpropyl)-5-oxo-4-phenylimidazolidin-1-yl]butyl}-N-alpha-(methoxycarbonyl)-L-phenylalaninamide_ | 596.3 |

TABLE 1-continued

| Compound | Structure | Compound Name | Exact Mass [M + H]+ |
|---|---|---|---|
| 32 | 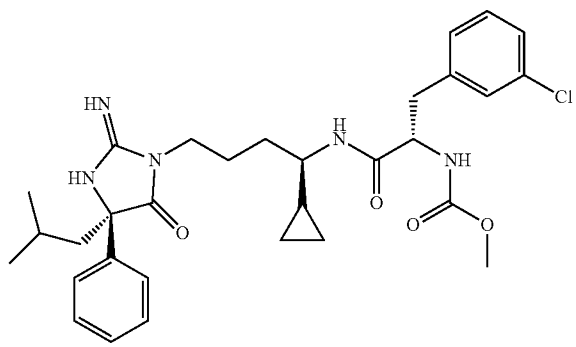 [SMILES: COC(=O)N[C@@H](Cc1cccc(Cl)c1)C(=O)N[C@H](CCCN1C(=N)N[C@](CC(C)C)(c2ccccc2)C1=O)C1CC1] | 3-chloro-N-{(1R)-1-cyclopropyl-4-[(4R)-2-imino-4-(2-methylpropyl)-5-oxo-4-phenylimidazolidin-1-yl]butyl}-N-alpha-(methoxycarbonyl)-L-phenylalaninamide | 582.3 |
| 33 | 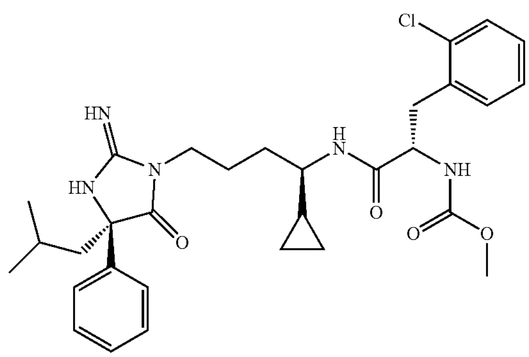 [SMILES: COC(=O)N[C@@H](Cc1ccccc1Cl)C(=O)N[C@H](CCCN1C(=N)N[C@](CC(C)C)(c2ccccc2)C1=O)C1CC1] | 2-chloro-N-{(1R)-1-cyclopropyl-4-[(4R)-2-imino-4-(2-methylpropyl)-5-oxo-4-phenylimidazolidin-1-yl]butyl}-N-alpha-(methoxycarbonyl)-L-phenylalaninamide | 582.3 |
| 34 | 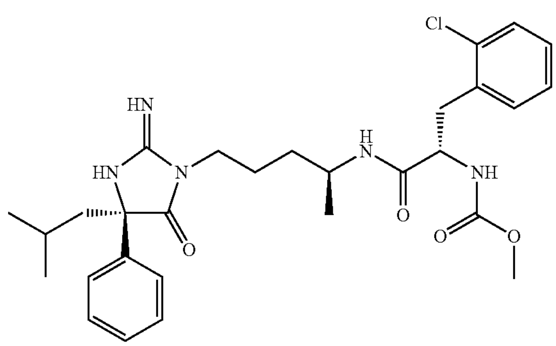 [SMILES: COC(=O)N[C@@H](Cc1ccccc1Cl)C(=O)N[C@@H](C)CCCN1C(=N)N[C@](CC(C)C)(c2ccccc2)C1=O] | 2-chloro-N-{(1S)-4-[(4R)-2-imino-4-(2-methylpropyl)-5-oxo-4-phenylimidazolidin-1-yl]-1-methylbutyl}-N-alpha-(methoxycarbonyl)-L-phenylalaninamide | 556.3 |
| 35 | 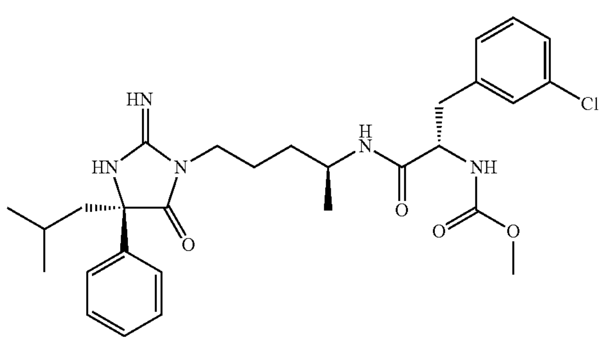 [SMILES: COC(=O)N[C@@H](Cc1cccc(Cl)c1)C(=O)N[C@@H](C)CCCN1C(=N)N[C@](CC(C)C)(c2ccccc2)C1=O] | 3-chloro-N-{(1S)-4-[(4R)-2-imino-4-(2-methylpropyl)-5-oxo-4-phenylimidazolidin-1-yl]-1-methylbutyl}-N-alpha-(methoxycarbonyl)-L-phenylalaninamide | 556.3 |

TABLE 1-continued

| Compound | Structure | Compound Name | Exact Mass [M + H]+ |
|---|---|---|---|
| 36 | 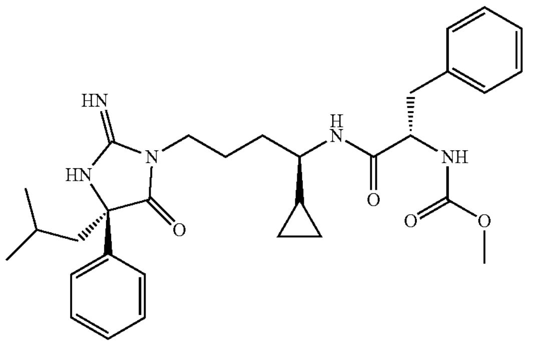 [SMILES: COC(=O)N[C@@H](Cc1ccccc1)C(=O)N[C@H](CCCN1C(=N)N[C@](CC(C)C)(c2ccccc2)C1=O)C1CC1] | N-{(1R)-1-cyclopropyl-4-[(4R)-2-imino-4-(2-methylpropyl)-5-oxo-4-phenylimidazolidin-1-yl]butyl}-N-alpha-(methoxycarbonyl)-L-phenylalaninamide | 548.3 |
| 37 | 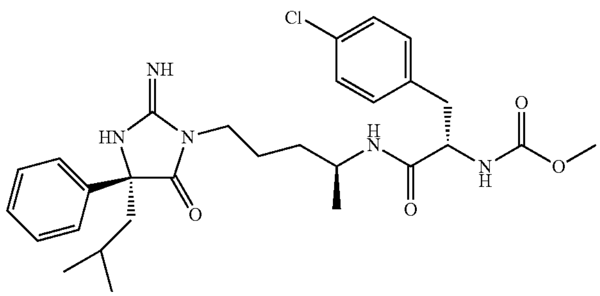 [SMILES: COC(=O)N[C@@H](Cc1ccc(Cl)cc1)C(=O)N[C@@H](C)CCCN1C(=N)N[C@](CC(C)C)(c2ccccc2)C1=O] | 4-chloro-N-{(1S)-4-[(4R)-2-imino-4-(2-methylpropyl)-5-oxo-4-phenylimidazolidin-1-yl]-1-methylbutyl}-N-alpha-(methoxycarbonyl)-L-phenylalamnamide | 556.3 |
| 38 | 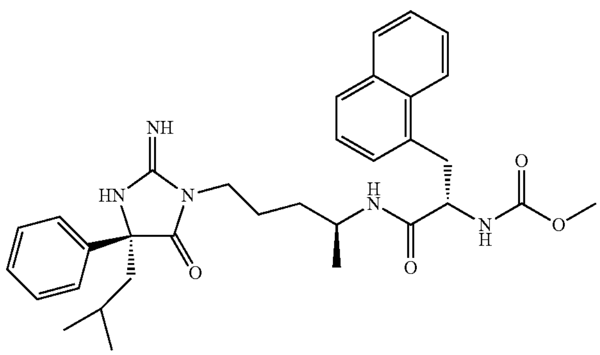 [SMILES: COC(=O)N[C@@H](Cc1cccc2ccccc12)C(=O)N[C@@H](C)CCCN1C(=N)N[C@](CC(C)C)(c2ccccc2)C1=O] | methyl [(1S)-2-({(1S)-4-[(4R)-2-imino-4-(2-methylpropyl)-5-oxo-4-phenylimidazolidin-1-yl]-1-methylbutyl}amino)-1-(naphthalen-1-ylmethyl)-2-oxoethyl]carbamate | 572.3 |
| 39 | 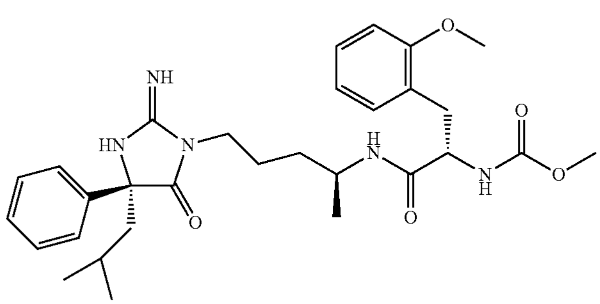 [SMILES: COC(=O)N[C@@H](Cc1ccccc1OC)C(=O)N[C@@H](C)CCCN1C(=N)N[C@](CC(C)C)(c2ccccc2)C1=O] | N-{(1S)-4-[(4R)-2-imino-4-(2-methylpropyl)-5-oxo-4-phenylimidazolidin-1-yl]-1-methylbutyl}-2-methoxy-N-alpha-(methoxycarbonyl)-L-phenylalaninamide | 552.3 |

TABLE 1-continued

| Compound | Structure | Compound Name | Exact Mass [M + H]+ |
|---|---|---|---|
| 40 | 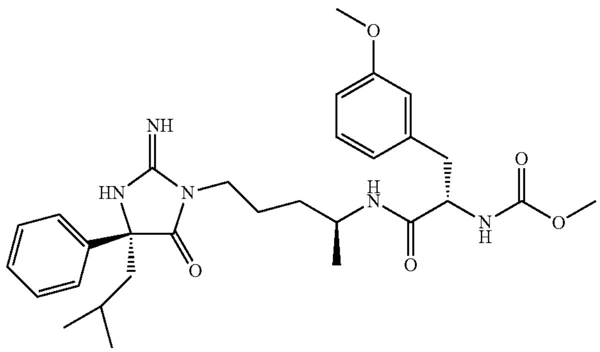 [SMILES: COC(=O)N[C@@H](Cc1cccc(OC)c1)C(=O)N[C@@H](C)CCCN1C(=N)N[C@](CC(C)C)(c2ccccc2)C1=O] | N-{(1S)-4-[(4R)-2-imino-4-(2-methylpropyl)-5-oxo-4-phenylimidazolidin-1-yl]-1-methylbutyl}-3-methoxy-N-alpha-(methoxycarbonyl)-L-phenylalaninamide | 552.3 |
| 41 | 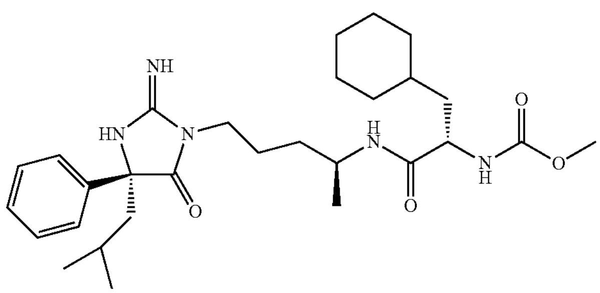 [SMILES: COC(=O)N[C@@H](CC1CCCCC1)C(=O)N[C@@H](C)CCCN1C(=N)N[C@](CC(C)C)(c2ccccc2)C1=O] | methyl [(1S)-1-(cyclohexylmethyl)-2-({(1S)-4-[(4R)-2-imino-4-(2-methylpropyl)-5-oxo-4-phenylimidazolidin-1-yl]-1-methylbutyl}amino)-2-oxoethyl]carbamate | 528.4 |
| 42 | 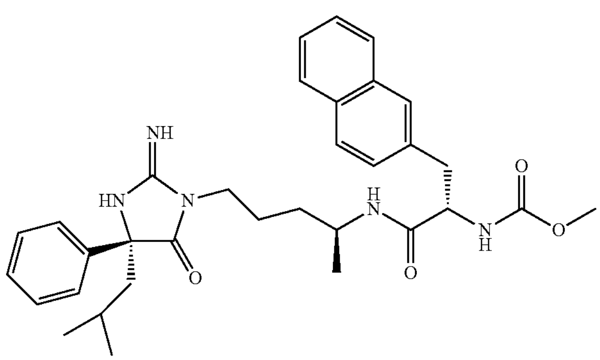 [SMILES: COC(=O)N[C@@H](Cc1ccc2ccccc2c1)C(=O)N[C@@H](C)CCCN1C(=N)N[C@](CC(C)C)(c2ccccc2)C1=O] | methyl ((S)-1-(((S)-5-((R)-2-imino-4-isobutyl-5-oxo-4-phenylimidazolidin-1-yl)pentan-2-yl)amino)-3-(naphthalen-2-yl)-1-oxopropan-2-yl)carbamate | 572.3 |
| 43 | 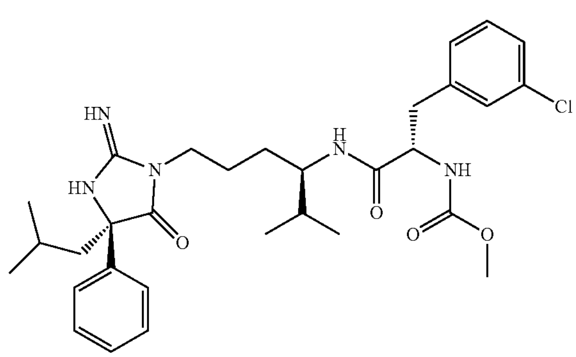 [SMILES: COC(=O)N[C@@H](Cc1cccc(Cl)c1)C(=O)N[C@H](CCCN1C(=N)N[C@](CC(C)C)(c2ccccc2)C1=O)C(C)C] | 3-chloro-N-[(1R)-4-[(4R)-2-imino-4-(2-methylpropyl)-5-oxo-4-phenylimidazolidin-1-yl]-1-(1-methylethyl)butyl]-N-alpha-(methoxycarbonyl)-L-phenylalaninamide | 584.3 |

TABLE 1-continued

| Compound | Structure | Compound Name | Exact Mass [M + H]+ |
|---|---|---|---|
| 44 | 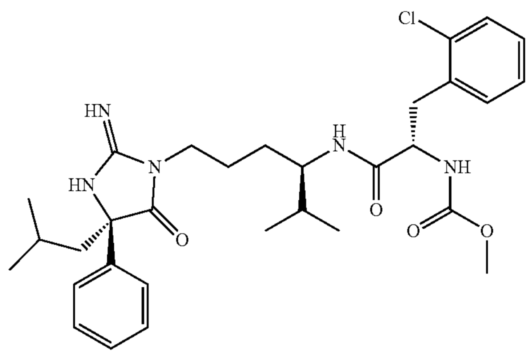 [SMILES: COC(=O)N[C@@H](Cc1ccccc1Cl)C(=O)N[C@H](CCCN1C(=N)N[C@](CC(C)C)(c2ccccc2)C1=O)C(C)C] | 2-chloro-N-[(1R)-4-[(4R)-2-imino-4-(2-methylpropyl)-5-oxo-4-phenylimidazolidin-1-yl]-1-(1-methylethyl)butyl]-N-alpha-(methoxycarbonyl)-L-phenylalaninamide | 584.3 |
| 45 | 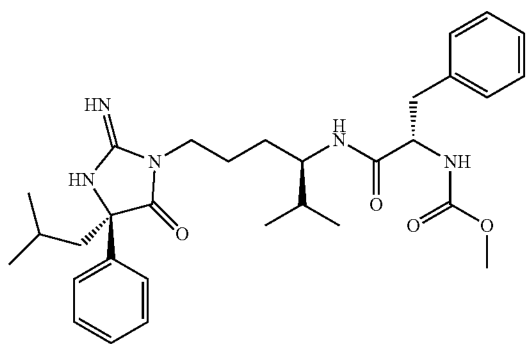 [SMILES: COC(=O)N[C@@H](Cc1ccccc1)C(=O)N[C@H](CCCN1C(=N)N[C@](CC(C)C)(c2ccccc2)C1=O)C(C)C] | N-[(1R)-4-[(4R)-2-imino-4-(2 methylpropyl)-5-oxo-4-phenylimidazolidin-1-yl]-1-(1 methylethyl)butyl]-N-alpha-(methoxycarbonyl)-L-phenylalaninamide | 550.3 |
| 46 | 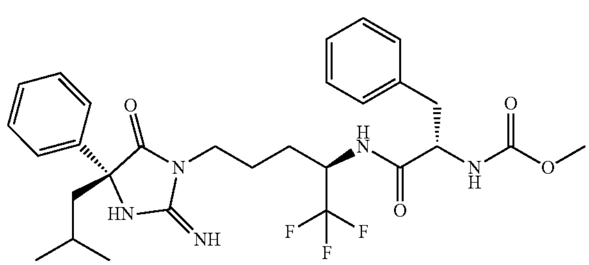 [SMILES: COC(=O)N[C@@H](Cc1ccccc1)C(=O)N[C@H](CCCN1C(=N)N[C@](CC(C)C)(c2ccccc2)C1=O)C(F)(F)F] | N-[(1R)-4-[(4R)-2-imino-4-(2-methylpropyl)-5-oxo-4-phenylimidazolidin-1-yl]-1-(trifluoromethyl)butyl]-N-alpha-(methoxycarbonyl)-L-phenylalaninamide | 576.3 |
| 47 | 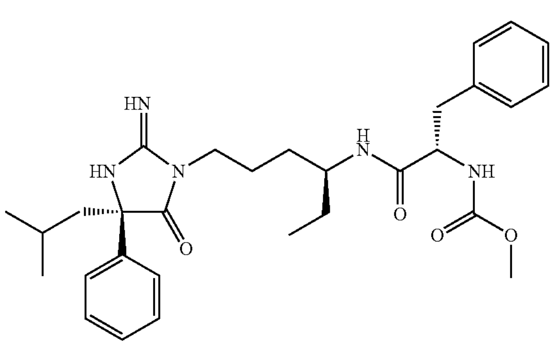 [SMILES: CC[C@@H](CCCN1C(=N)N[C@](CC(C)C)(c2ccccc2)C1=O)NC(=O)[C@H](Cc1ccccc1)NC(=O)OC] | N-{(1S)-1-ethyl-4-[(4R)-2-imino-4-(2-methylpropyl)-5 oxo-4-phenylimidazolidin-1 yl]butyl}-N-alpha-(methoxycarbonyl)-L-phenylalaninamide | 536.3 |

TABLE 1-continued

| Compound | Structure | Compound Name | Exact Mass [M + H]+ |
|---|---|---|---|
| 48 | 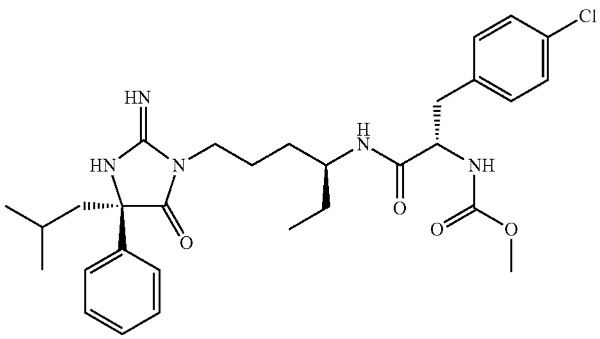 [SMILES: CC[C@@H](CCCN1C(=N)N[C@](CC(C)C)(c2ccccc2)C1=O)NC(=O)[C@H](Cc1ccc(Cl)cc1)NC(=O)OC] | 4-chloro-N-{(1S)-1-ethyl-4-[(4R)-2-imino-4-(2-methylpropyl)-5-oxo-4-phenylimidazolidin-1-yl]butyl}-N-alpha-(methoxycarbonyl)-L-phenylalaninamide | 570.3 |
| 49 | 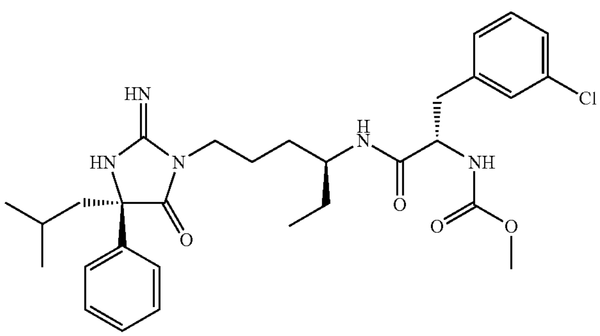 [SMILES: CC[C@@H](CCCN1C(=N)N[C@](CC(C)C)(c2ccccc2)C1=O)NC(=O)[C@H](Cc1cccc(Cl)c1)NC(=O)OC] | 3-chloro-N-{(1S)-1-ethyl-4-[(4R)-2-imino-4-(2-methylpropyl)-5-oxo-4-phenylimidazolidin-1-yl]butyl}-N-alpha-(methoxycarbonyl)-L-phenylalaninamide | 570.3 |
| 50 | 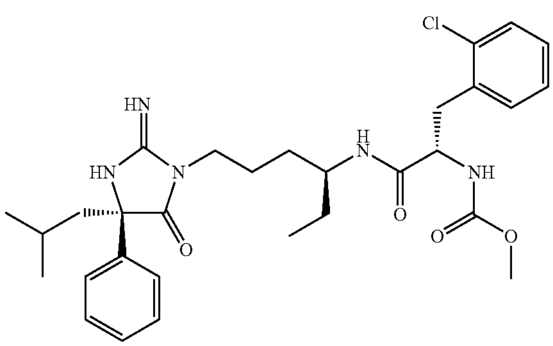 [SMILES: CC[C@@H](CCCN1C(=N)N[C@](CC(C)C)(c2ccccc2)C1=O)NC(=O)[C@H](Cc1ccccc1Cl)NC(=O)OC] | 2-chloro-N-{(1S)-1-ethyl-4-[(4R)-2-imino-4-(2-methylpropyl)-5-oxo-4-phenylimidazolidin-1-yl]butyl}-N-alpha-(methoxycarbonyl)-L-phenylalaninamide | 570.3 |
| 51 | 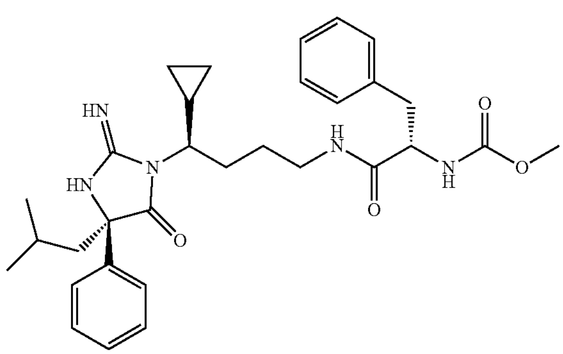 [SMILES: COC(=O)N[C@@H](Cc1ccccc1)C(=O)NCCC[C@H](C1CC1)N1C(=N)N[C@](CC(C)C)(c2ccccc2)C1=O] | N-{(4R)-4-cyclopropyl-4-[(4R)-2-imino-4-(2-methylpropyl)-5-oxo-4-phenylimidazolidin-1-yl]butyl}-N-alpha-(methoxycarbonyl)-L-phenylalaninamide | 548.3 |

TABLE 1-continued

| Compound | Structure | Compound Name | Exact Mass [M + H]+ |
|---|---|---|---|
| 52 | 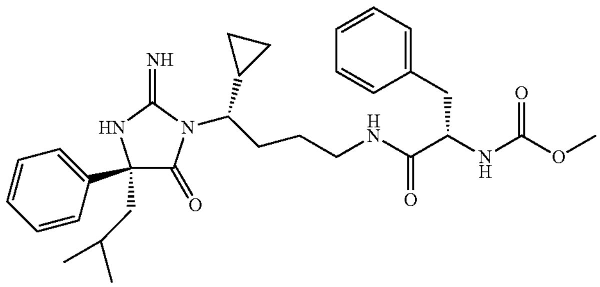 [SMILES: COC(=O)N[C@@H](Cc1ccccc1)C(=O)NCCC[C@@H](C1CC1)N1C(=N)N[C@](CC(C)C)(c2ccccc2)C1=O] | N-{(4S)-4-cyclopropyl-4-[(4R)-2-imino-4-(2-methylpropyl)-5-oxo-4-phenylimidazolidin-1-yl]butyl}-N-alpha-(methoxycarbonyl)-L-phenylalaninamide | 548.3 |
| 53 | 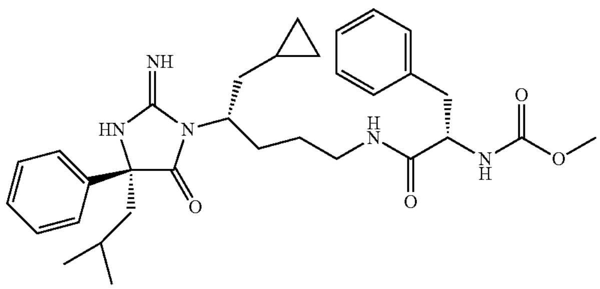 [SMILES: COC(=O)N[C@@H](Cc1ccccc1)C(=O)NCCC[C@@H](CC1CC1)N1C(=N)N[C@](CC(C)C)(c2ccccc2)C1=O] | N-{(4S)-5-cyclopropyl-4-[(4R)-2-imino-4-(2-methylpropyl)-5-oxo-4-phenylimidazolidin-1-yl]pentyl}-N-alpha-(methoxycarbonyl)-L-phenylalaninamide | 562.3 |
| 54 | 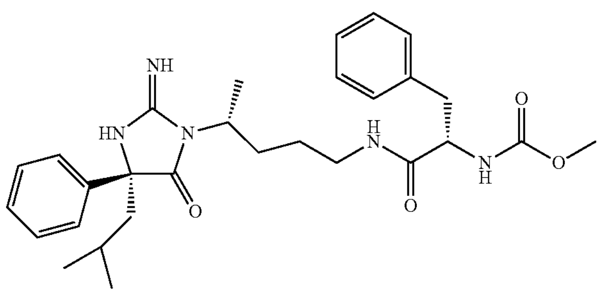 [SMILES: COC(=O)N[C@@H](Cc1ccccc1)C(=O)NCCC[C@@H](C)N1C(=N)N[C@](CC(C)C)(c2ccccc2)C1=O] | N-{(4R)-4-[(4R)-2-imino-4-(2-methylpropyl)-5-oxo-4-phenylimidazolidin-1-yl]pentyl}-N-alpha-(methoxycarbonyl)-L-phenylalaninamide | 522.3 |
| 55 | 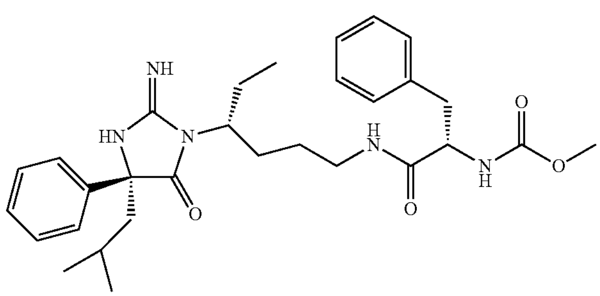 [SMILES: CC[C@H](CCCNC(=O)[C@H](Cc1ccccc1)NC(=O)OC)N1C(=N)N[C@](CC(C)C)(c2ccccc2)C1=O] | N-{(4R)-4-[(4R)-2-imino-4-(2-methylpropyl)-5-oxo-4-phenylimidazolidin-1-yl]hexyl}-N-alpha-(methoxycarbonyl)-L-phenylalaninamide | 536.3 |
| 56 | 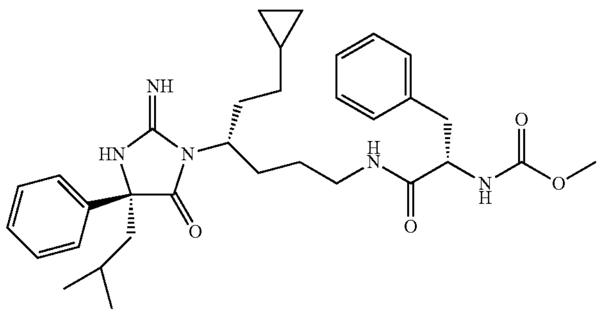 [SMILES: COC(=O)N[C@@H](Cc1ccccc1)C(=O)NCCC[C@@H](CCC1CC1)N1C(=N)N[C@](CC(C)C)(c2ccccc2)C1=O] | N-{(4R)-6-cyclopropyl-4-[(4R)-2-imino-4-(2-methylpropyl)-5-oxo-4-phenylimidazolidin-1-yl]hexyl}-N-alpha-(methoxycarbonyl)-L-phenylalaninamide | 576.4 |

Assay for Inhibition of Microbial Expressed HIV Protease

Inhibition of *Escherichia coli* expressed wild-type HIV-1 protease protein was carried out with a peptide substrate [Val-Ser-Gln-Asn-(βnaphtyl)Ala-Pro-Ile-Val]. The inhibitor compound was preincubated with HIV-1 protease enzyme in assay buffer (50 mM sodium acetate, pH 5.5, 100 mM NaCl, and 0.1% BSA) for 30 minutes at room temperature. Peptide substrate was added to 400 LM in a total volume of 20 μL containing 20 pM HIV-1 protease (final) after which the reaction was incubated for 1 hour at 30° C. The reaction was quenched by the addition of formic acid and HIV protease inhibitor indinavir to 0.012% and 150 nM final concentrations, respectively. Product formation was determined after separation of product and substrate on a ZORBAX Eclipse XDB-C18 column (Aligent Technologies, Santa Clara, Calif., USA) connected to an API 4000™ mass spectrometer (AB Sciex, Pte. Ltd., Concord Ontario, Canada) with multiple reaction monitoring (transitions were 644.5/428.9 and 615.4/422.2 (M1/M3) for product and indinavir respectively). The extent of inhibition of the reaction was determined from the peak area of the products. Analysis of the products, independently synthesized, provided quantitation standards and confirmation of the product composition. Representative compounds of the present invention exhibit inhibition of HIV-1 protease in this assay.

MT4-GFP cells contain a stably integrated HIV long terminal repeat promoter directing the transcription of green fluorescent protein (GFP). When HIV infects the cell, GFP is produced and the cell becomes green. MT4-GFP cells (250,000 cells/mL) were bulk-infected with HIV-1 (H9IIB strain) at low multiplicity of infection (MOI) in Gibco™ RPMI 1640 media (ThermoFisher Scientific, Waltham, Mass., USA), supplemented with 10% FBS for 24 h. Cells were then washed once in Gibco™ RPMI 1640 plus 10% FBS and resuspended in RPMI plus 50% normal human serum (NHS). Test compounds were serial-diluted in DMSO using an Echo® Acoustic Dispenser (Labcyte Inc, Sunnyvale, Calif., USA). A control well included a combination of three HIV drugs (an inhibitor of HIV protease, integrase strand transfer and a non-nucleoside reverse transcriptase inhibitor; triple drug). The infected MT4-GFP cells were added to a 384-well poly-D-lysine coated black plate with clear bottom in which the diluted test compounds were placed. The cells were seeded in the plate at 8,000 cells per well and the final DMSO concentration was 0.4%. Infected cells were quantified at both 24 and 48 h post incubation using an Acumen eX3 plate reader (TTP Labtech, Cambridge, UK). Viral reproductive ratio ($R_O$) was determined using the number of infected cells at 48 h divided by the number of infected cells at 24 h. Percent viral growth inhibition was calculated by $[1-(R-R_{tripledrug})/(R_{DMSO}-R_{tripledrug})]*100$. Compound potency inflection point (IP) was determined with use of a 4-parameter dose response curve analysis Table 2 shows data obtained from the above described assays for the Examples herein. The IC50's are defined as the 50 percent inhibition of the cleavage of the peptide s. substrate by HIV Protease. Data shown in the table reflects the mean of at least two independent experiments.

TABLE 2

| Example Number | HIV Pr Enzyme HIV1 PR IC$_{50}$ nM |
|---|---|
| 1 | 18 |
| 2 | 11 |
| 3 | 8 |
| 4 | 10 |
| 5 | 6 |
| 6 | 4 |
| 7 | 2 |
| 8 | 12 |
| 9 | 31 |
| 10 | 34 |
| 11 | 7 |
| 12 | 21 |
| 13 | 7 |
| 14 | 67 |
| 15 | 98 |
| 16 | 19 |
| 17 | 20 |
| 18 | 25 |
| 19 | 24 |
| 20 | 91 |
| 21 | 46 |
| 22 | 60 |
| 23 | 16 |
| 24 | 22 |
| 25 | 17 |
| 26 | 27 |
| 27 | 27 |
| 28 | 9 |
| 29 | 33 |
| 30 | 97 |
| 31 | 80 |
| 32 | 43 |
| 33 | 23 |
| 34 | 18 |
| 35 | 20 |
| 36 | 9 |
| 37 | 61 |
| 38 | 23 |
| 39 | 3 |
| 40 | 54 |
| 41 | 31 |
| 42 | 46 |
| 43 | 5 |
| 44 | 20 |
| 45 | 27 |
| 46 | 32 |
| 47 | 22 |
| 48 | 14 |
| 49 | 15 |
| 50 | 6 |
| 51 | 7 |
| 52 | 605 |
| 53 | 249 |
| 54 | 190 |
| 55 | 532 |
| 56 | 100 |

While the foregoing specification teaches the principles of the present invention, with examples provided for the purpose of illustration, the practice of the invention encompasses all of the usual variations, adaptations and/or modifications that come within the scope of the following claims. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All publications, patents and patent applications cited herein are incorporated by reference in their entirety into the disclosure.

What is claimed is:

1. A compound of structural Formula I:

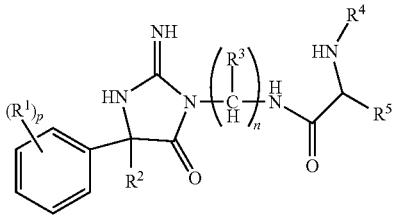

or a pharmaceutically acceptable salt thereof, wherein:
$R^1$ is selected from hydrogen, halogen, $C_{1-3}$alkyl, $C_{1-3}$haloalkyl, —$OC_{1-3}$haloalkyl, CN, —$C(O)NHC_{1-6}$alkyl and —$SO_2C_{1-6}$alkyl;
$R^2$ is selected from $C_{6-10}$aryl, $C_{1-6}$alkyl, $(CH_2)_kC_{1-3}$haloalkyl, $(CH_2)_kC_{3-6}$cycloalkyl, $(CH_2)_kC_{6-10}$aryl, $(CH_2)_k$ $C_{5-10}$heterocycloalkyl and $(CH_2)_kC_{5-10}$heteroaryl, wherein $R^2$ is substituted with 0, 1, 2 or 3 of $R^6$ selected from halogen, hydroxy, and $C_{1-4}$alkoxy;
$R^3$ is selected from hydrogen, $C_{1-4}$alkyl, $C_{3-8}$cycloalkyl $C_{1-6}$alkyl, $C_{3-8}$cycloalkyl, and $C_{1-4}$haloalkyl, wherein $R^3$ is substituted with 0, 1, 2 or 3 of $R^7$ selected from halogen and hydroxy;
$R^4$ is selected from $C_{1-6}$alkyl carbonyl, $C_{1-6}$alkylcarboxy, cyclopropylcarboxy and $C_{3-8}$alkylcycloalkylcarboxy, wherein $R^4$ is substituted with 0, 1, 2, or 3 of $R^8$ selected from $C_{1-6}$alkyl and halogen;
$R^5$ is selected from $C_{3-8}$cycloalkyl $C_{1-6}$alkyl, $C_{3-8}$heterocycloalkyl $C_{1-6}$alkyl, $C_{6-10}$aryl $C_{1-6}$alkyl, and $C_{5-10}$heteroaryl $C_{1-6}$alkyl, $R^5$ is substituted with 0, 1, or 2 of $R^9$ selected from $C_{1-5}$alkyl, cyano, $C_{1-6}$alkoxy, and halogen;
n is 1, 2, 3, 4, 5, or 6;
p is 0, 1, 2, or 3; and
k is 0, 1, 2, 3, or 4.

2. The compound according to claim 1 wherein $R^2$ is phenyl, isopentyl, or isobutyl, wherein $R^2$ is substituted by 0, 1, 2, or 3 of fluoro.

3. The compound according to claim 1 wherein $R^3$ is selected from hydrogen, methyl, cyclopropylmethyl, cyclopropyl, methylethyl, trifluoromethyl, ethyl, and cyclopropyl ethyl, wherein $R^3$ is substituted by 0, 1, or 2 of fluoro.

4. The compound according to claim 1 wherein $R^4$ is selected from, methylcarbonyl, methylcarboxy, ethylcarboxy, cyclopropylcarboxy and isopropylcarboxy, wherein $R^4$ is substituted by 0, 1, or 2 of methyl or fluoro.

5. The compound according to claim 1 wherein $R^5$ is selected from benzyl, phenylethyl, pyridinylmethyl, naphalenylmethyl, and cyclohexylmethyl, wherein $R^5$ is substituted by 0, 1, or 2 of cyano, methoxy, fluoro, or chloro.

6. The compound according to claim 5 wherein n is 3, 4 or 5.

7. The compound according to claim 6 wherein p is 0, 1 or 2.

8. A compound which is:
N-{4-[2-imino-4-(2-methylpropyl)-5-oxo-4-phenylimidazolidin-1-yl]-1-methylbutyl}-N-alpha-(methoxycarbonyl)-O-methyl-L-tyrosinamide;
N-alpha-acetyl-N-[4-(2-imino-5-oxo-4,4-diphenylimidazolidin-1-yl)butyl]-L-phenylalaninamide;
N-[4-(2-imino-5-oxo-4,4-diphenylimidazolidin-1-yl)butyl]-N-alpha-(methoxycarbonyl)-L-phenylalaninamide;
2-amino-N-[4-(2-imino-5-oxo-4,4-diphenylimidazolidin-1-yl)butyl]-4-phenylbutanamide;
N-alpha-(ethoxycarbonyl)-N-[4-(2-imino-5-oxo-4,4-diphenylimidazolidin-1-yl)butyl]-L-phenylalaninamide;
N-[4-(2-imino-5-oxo-4,4-diphenylimidazolidin-1-yl)-1-methylbutyl]-N-alpha-(methoxycarbonyl)-L-phenylalaninamide;
methyl [2-{[4-(2-imino-5-oxo-4,4-diphenylimidazolidin-1-yl)butyl]amino}-2-oxo-1-(pyridin-3-ylmethyl)ethyl]carbamate;
N-[4-(2-imino-5-oxo-4,4-diphenylimidazolidin-1-yl)butyl]-3-pyridin-3-yl-L-alaninamide;
N-[4-(2-imino-5-oxo-4,4-diphenylimidazolidin-1-yl)butyl]-3-pyridin-4-yl-L-alaninamide;
N-{4-[4,4-bis(4-fluorophenyl)-2-imino-5-oxoimidazolidin-1-yl]-1-methylbutyl}-N-alpha-(methoxycarbonyl)-L-phenylalaninamide;
methyl [2-{[4-(2-imino-5-oxo-4,4-diphenylimidazolidin-1-yl)butyl]amino}-2-oxo-1-(pyridin-2-ylmethyl)ethyl]carbamate;
methyl [2-{[4-(2-imino-5-oxo-4,4-diphenylimidazolidin-1-yl)butyl]amino}-2-oxo-1-(pyridin-4-ylmethyl)ethyl]carbamate;
N-[5-(2-imino-5-oxo-4,4-diphenylimidazolidin-1-yl)pentyl]-L-phenylalaninamide;
N-[5-(2-imino-5-oxo-4,4-diphenylimidazolidin-1-yl)pentyl]-N-alpha-(methoxycarbonyl)-L-phenylalaninamide;
N-{4-[2-imino-4-(2-methylpropyl)-5-oxo-4-phenylimidazolidin-1-yl]butyl}-L-phenylalaninamide;
N-{4-[2-imino-4-(2-methylpropyl)-5-oxo-4-phenylimidazolidin-1-yl]butyl}-N-alpha-(methoxycarbonyl)-L-phenylalaninamide;
N-{4-[2-imino-4-(3-methylbutyl)-5-oxo-4-phenylimidazolidin-1-yl]butyl}-L-phenylalaninamide;
N-{4-[2-imino-4-(3-methylbutyl)-5-oxo-4-phenylimidazolidin-1-yl]butyl)}-N-alpha-(methoxycarbonyl)-L-phenylalaninamide;
methyl [2-{[5-(2-imino-5-oxo-4,4-diphenylimidazolidin-1-yl)pentyl]amino}-2-oxo-1-(pyridin-4-ylmethyl)ethyl]carbamate;
methyl [2-({4-[2-imino-4-(2-methylpropyl)-5-oxo-4-phenylimidazolidin-1-yl]butyl}amino)-2-oxo-1-(pyridin-4-ylmethyl)ethyl]carbamate;
methyl [2-({4-[2-imino-4-(3-methylbutyl)-5-oxo-4-phenylimidazolidin-1-yl]butyl}amino)-2-oxo-1-(pyridin-4-ylmethyl)ethyl]carbamate;
N-[4-(2-imino-5-oxo-4,4-diphenylimidazolidin-1-yl)butyl]-N-alpha-{[(1-methylcyclopropyl)oxy]carbonyl}-L-phenylalaninamide;
3-cyano-N-[4-(2-imino-5-oxo-4,4-diphenylimidazolidin-1-yl)butyl]-L-phenylalaninamide;
4-fluoro-N-[4-(2-imino-5-oxo-4,4-diphenylimidazolidin-1-yl)butyl]-N-alpha-(methoxycarbonyl)-L-phenylalaninamide;
N-[4-(2-imino-5-oxo-4,4-diphenylimidazolidin-1-yl)butyl]-N-alpha-[(1-methylethoxy)carbonyl]-L-phenylalaninamide;
4-fluoro-N-{4-[2-imino-4-(2-methylpropyl)-5-oxo-4-phenylimidazolidin-1-yl]-1-methylbutyl}-N-alpha-(methoxycarbonyl)-L-phenylalaninamide;
N-{4-[2-imino-4-(2-methylpropyl)-5-oxo-4-phenylimidazolidin-1-yl]-1-methylbutyl)}-N-alpha-(methoxycarbonyl)-L-phenylalaninamide;

N-{1-(cyclopropylmethyl)-4-[2-imino-4-(2-methylpropyl)-5-oxo-4-phenylimidazolidin-1-yl]butyl}-N-alpha-(methoxycarbonyl)-L-phenylalaninamide;

3-chloro-N-{1-(cyclopropylmethyl)-4-[2-imino-4-(2-methylpropyl)-5-oxo-4-phenylimidazolidin-1-yl]butyl}-N-alpha-(methoxycarbonyl)-L-phenylalaninamide;

2-chloro-N-{1-(cyclopropylmethyl)-4-[2-imino-4-(2-methylpropyl)-5-oxo-4-phenylimidazolidin-1-yl]butyl}-N-alpha-(methoxycarbonyl)-L-phenylalaninamide;

3-chloro-N-{1-cyclopropyl-4-[2-imino-4-(2-methylpropyl)-5-oxo-4-phenylimidazolidin-1-yl]butyl}-N-alpha-(methoxycarbonyl)-L-phenylalaninamide;

2-chloro-N-{1-cyclopropyl-4-[2-imino-4-(2-methylpropyl)-5-oxo-4-phenylimidazolidin-1-yl]butyl}-N-alpha-(methoxycarbonyl)-L-phenylalaninamide;

2-chloro-N-{4-[2-imino-4-(2-methylpropyl)-5-oxo-4-phenylimidazolidin-1-yl]-1-methylbutyl}-N-alpha-(methoxycarbonyl)-L-phenylalaninamide;

3-chloro-N-{4-[2-imino-4-(2-methylpropyl)-5-oxo-4-phenylimidazolidin-1-yl]-1-methylbutyl}-N-alpha-(methoxycarbonyl)-L-phenylalaninamide;

N-{1-cyclopropyl-4-[2-imino-4-(2-methylpropyl)-5-oxo-4-phenylimidazolidin-1-yl]butyl}-N-alpha-(methoxycarbonyl)-L-phenylalaninamide;

4-chloro-N-{4-[2-imino-4-(2-methylpropyl)-5-oxo-4-phenylimidazolidin-1-yl]-1-methylbutyl}-N-alpha-(methoxycarbonyl)-L-phenylalaninamide;

methyl [2-({4-[2-imino-4-(2-methylpropyl)-5-oxo-4-phenylimidazolidin-1-yl]-1-methylbutyl}amino)-1-(naphthalen-1-ylmethyl)-2-oxoethyl]carbamate;

N-{4-[2-imino-4-(2-methylpropyl)-5-oxo-4-phenylimidazolidin-1-yl]-1-methylbutyl)}-2-methoxy-N-alpha-(methoxycarbonyl)-L-phenylalaninamide;

N-{4-[2-imino-4-(2-methylpropyl)-5-oxo-4-phenylimidazolidin-1-yl]-1-methylbutyl}-3-methoxy-N-alpha-(methoxycarbonyl)-L-phenylalaninamide;

methyl [1-(cyclohexylmethyl)-2-({4-[2-imino-4-(2-methylpropyl)-5-oxo-4-phenylimidazolidin-1-yl]-1-methylbutyl}amino)-2-oxoethyl]carbamate;

methyl (1-((5-(2-imino-4-isobutyl-5-oxo-4-phenylimidazolidin-1-yl)pentan-2-yl)amino)-3-(naphthalen-2-yl)-1-oxopropan-2-yl)carbamate;

3-chloro-N-[4-[2-imino-4-(2-methylpropyl)-5-oxo-4-phenylimidazolidin-1-yl]-1-(1-methylethyl)butyl]-N-alpha-(methoxycarbonyl)-L-phenylalaninamide;

2-chloro-N-[4-[2-imino-4-(2-methylpropyl)-5-oxo-4-phenylimidazolidin-1-yl]-1-(1-methylethyl)butyl]-N-alpha-(methoxycarbonyl)-L-phenylalaninamide;

N-[4-[2-imino-4-(2-methylpropyl)-5-oxo-4-phenylimidazolidin-1-yl]-1-(1-methylethyl)butyl]-N-alpha-(methoxycarbonyl)-L-phenylalaninamide;

N-[4-[2-imino-4-(2-methylpropyl)-5-oxo-4-phenylimidazolidin-1-yl]-1-(trifluoromethyl)butyl]-N-alpha-(methoxycarbonyl)-L-phenylalaninamide;

N-{1-ethyl-4-[2-imino-4-(2-methylpropyl)-5-oxo-4-phenylimidazolidin-1-yl]butyl}-N-alpha-(methoxycarbonyl)-L-phenylalaninamide;

4-chloro-N-{1-ethyl-4-[2-imino-4-(2-methylpropyl)-5-oxo-4-phenylimidazolidin-1-yl]butyl}-N-alpha-(methoxycarbonyl)-L-phenylalaninamide;

3-chloro-N-{1-ethyl-4-[2-imino-4-(2-methylpropyl)-5-oxo-4-phenylimidazolidin-1-yl]butyl}-N-alpha-(methoxycarbonyl)-L-phenylalaninamide;

2-chloro-N-{1-ethyl-4-[2-imino-4-(2-methylpropyl)-5-oxo-4-phenylimidazolidin-1-yl]butyl}-N-alpha-(methoxycarbonyl)-L-phenylalaninamide;

N-{4-cyclopropyl-4-[2-imino-4-(2-methylpropyl)-5-oxo-4-phenylimidazolidin-1-yl]butyl)}-N-alpha-(methoxycarbonyl)-L-phenylalaninamide;

N-{5-cyclopropyl-4-[2-imino-4-(2-methylpropyl)-5-oxo-4-phenylimidazolidin-1-yl]pentyl)}-N-alpha-(methoxycarbonyl)-L-phenylalaninamide;

N-{4-[2-imino-4-(2-methylpropyl)-5-oxo-4-phenylimidazolidin-1-yl]pentyl}-N-alpha-(methoxycarbonyl)-L-phenylalaninamide;

N-{4-[2-imino-4-(2-methylpropyl)-5-oxo-4-phenylimidazolidin-1-yl]hexyl}-N-alpha-(methoxycarbonyl)-L-phenylalaninamide; or N-{6-cyclopropyl-4-[2-imino-4-(2-methylpropyl)-5-oxo-4-phenylimidazoidin-1-yl]hexyl)}-N-alpha-(methoxycarbonyl)-L-phenylalaninamide;

or a pharmaceutically acceptable salt thereof.

9. A compound which is:

| No. |
| --- |
| 1 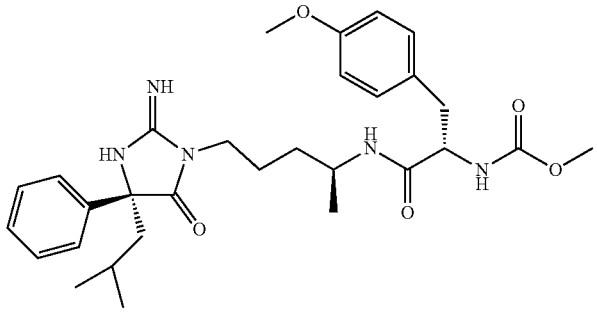 [SMILES: COC(=O)N[C@@H](Cc1ccc(OC)cc1)C(=O)N[C@@H](C)CCCN1C(=N)N[C@](CC(C)C)(c2ccccc2)C1=O] |

-continued
| No. |
|---|
| 3 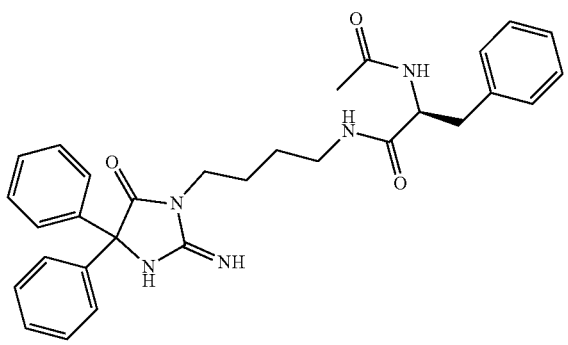 [SMILES: CC(=O)N[C@@H](Cc1ccccc1)C(=O)NCCCCN1C(=N)NC(c2ccccc2)(c2ccccc2)C1=O] |
| 4 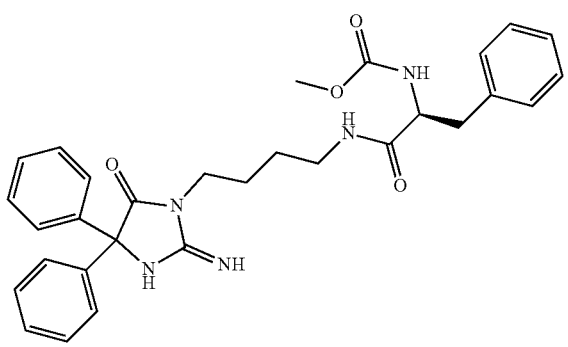 [SMILES: COC(=O)N[C@@H](Cc1ccccc1)C(=O)NCCCCN1C(=N)NC(c2ccccc2)(c2ccccc2)C1=O] |
| 5 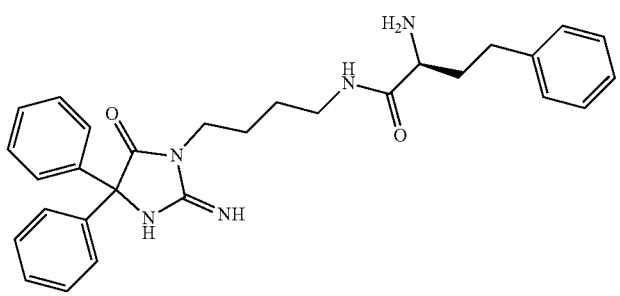 [SMILES: N=C1NC(c2ccccc2)(c2ccccc2)C(=O)N1CCCCNC(=O)[C@@H](N)CCc1ccccc1] |
| 6 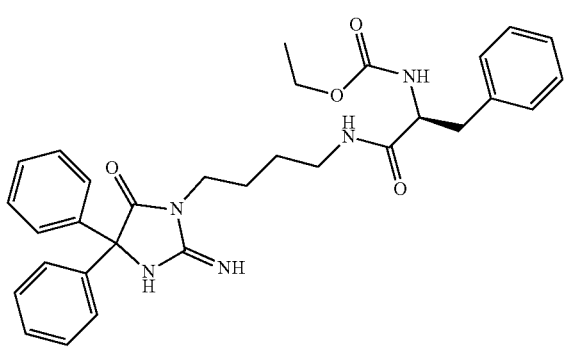 [SMILES: CCOC(=O)N[C@@H](Cc1ccccc1)C(=O)NCCCCN1C(=N)NC(c2ccccc2)(c2ccccc2)C1=O] |
| 7 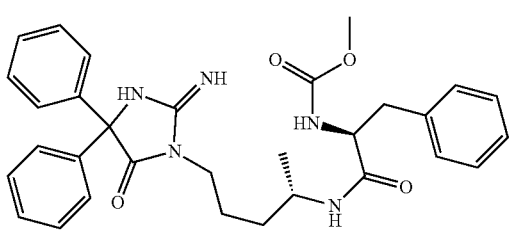 [SMILES: COC(=O)N[C@@H](Cc1ccccc1)C(=O)N[C@@H](C)CCCN1C(=N)NC(c2ccccc2)(c2ccccc2)C1=O] |

| No. |
|---|
| 8 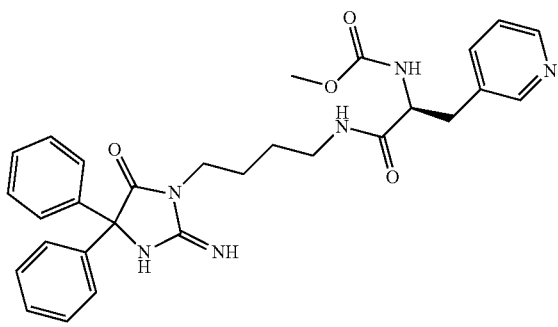 [SMILES: COC(=O)N[C@@H](Cc1cccnc1)C(=O)NCCCCN1C(=N)NC(c2ccccc2)(c2ccccc2)C1=O] |
| 9 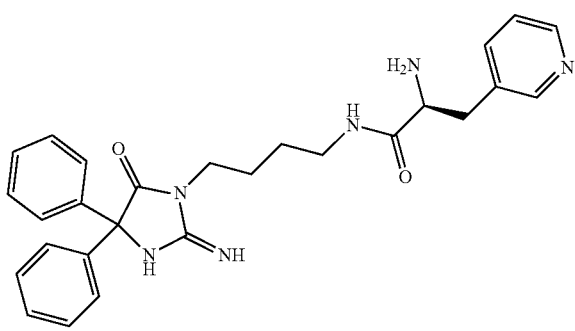 [SMILES: N=C1NC(c2ccccc2)(c2ccccc2)C(=O)N1CCCCNC(=O)[C@@H](N)Cc1cccnc1] |
| 10 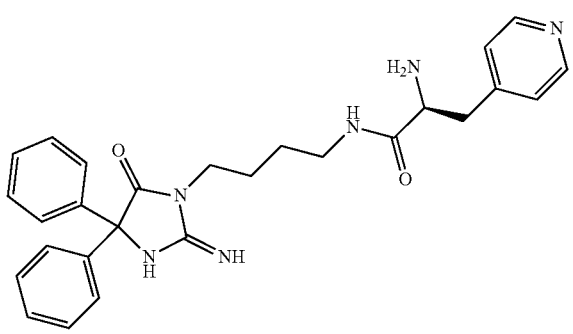 [SMILES: N=C1NC(c2ccccc2)(c2ccccc2)C(=O)N1CCCCNC(=O)[C@@H](N)Cc1ccncc1] |
| 11 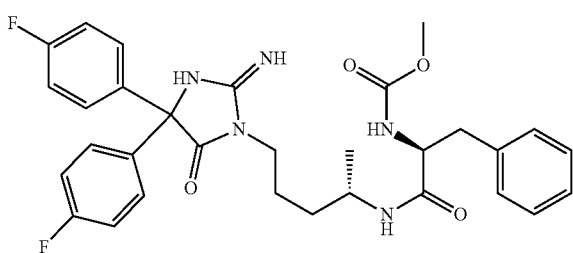 [SMILES: COC(=O)N[C@@H](Cc1ccccc1)C(=O)N[C@@H](C)CCCN1C(=N)NC(c2ccc(F)cc2)(c2ccc(F)cc2)C1=O] |
| 12 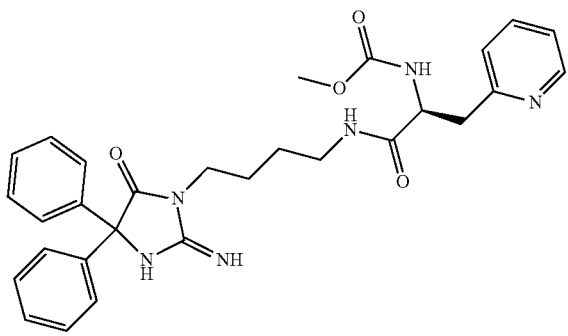 [SMILES: COC(=O)N[C@@H](Cc1ccccn1)C(=O)NCCCCN1C(=N)NC(c2ccccc2)(c2ccccc2)C1=O] |

-continued
| No. |
|---|
| 13 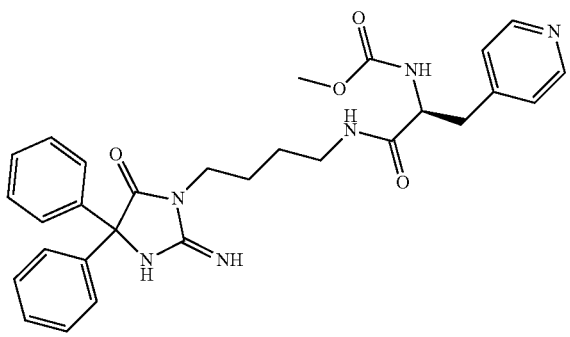 [SMILES: COC(=O)N[C@@H](Cc1ccncc1)C(=O)NCCCCN1C(=N)NC(c2ccccc2)(c2ccccc2)C1=O] |
| 14 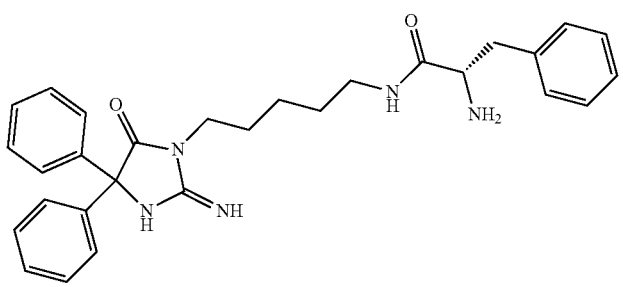 [SMILES: N=C1NC(c2ccccc2)(c2ccccc2)C(=O)N1CCCCCNC(=O)[C@@H](N)Cc1ccccc1] |
| 15 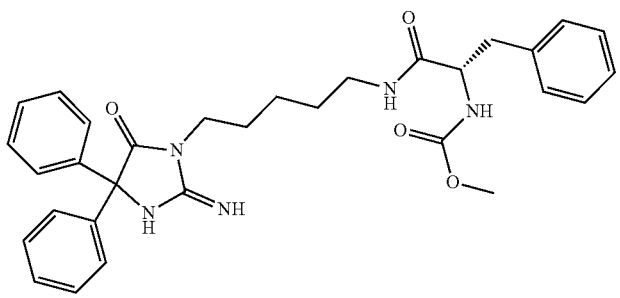 [SMILES: COC(=O)N[C@@H](Cc1ccccc1)C(=O)NCCCCCN1C(=N)NC(c2ccccc2)(c2ccccc2)C1=O] |
| 16 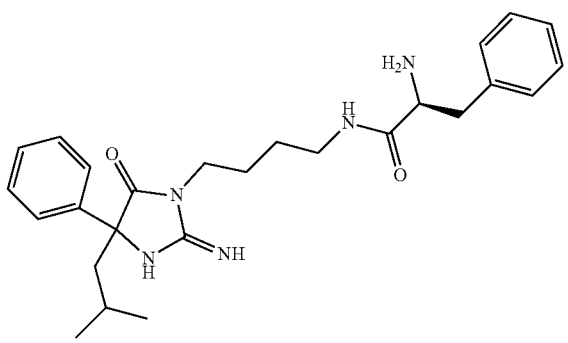 [SMILES: CC(C)CC1(c2ccccc2)NC(=N)N(CCCCNC(=O)[C@@H](N)Cc2ccccc2)C1=O] |
| 17 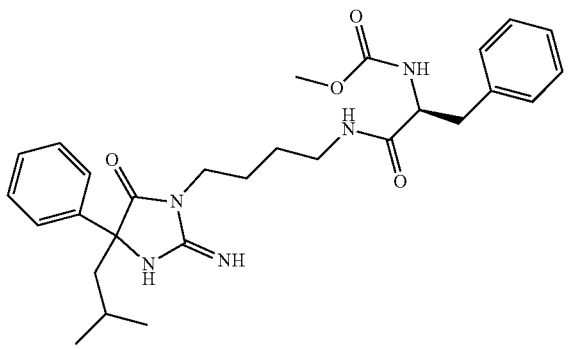 [SMILES: COC(=O)N[C@@H](Cc1ccccc1)C(=O)NCCCCN1C(=N)NC(CC(C)C)(c2ccccc2)C1=O] |

| No. |
|---|
| 18 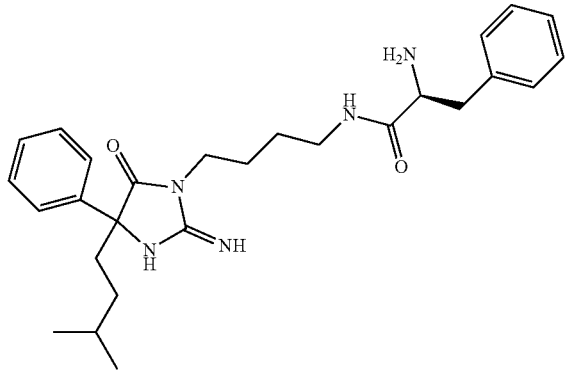 [SMILES: CC(C)CCC1(c2ccccc2)NC(=N)N(CCCCNC(=O)[C@@H](N)Cc2ccccc2)C1=O] |
| 19 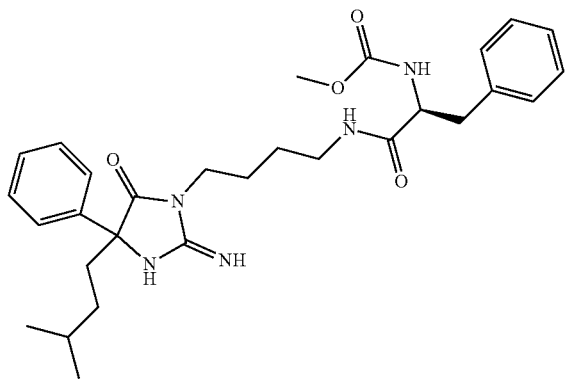 [SMILES: COC(=O)N[C@@H](Cc1ccccc1)C(=O)NCCCCN1C(=N)NC(CCC(C)C)(c2ccccc2)C1=O] |
| 20 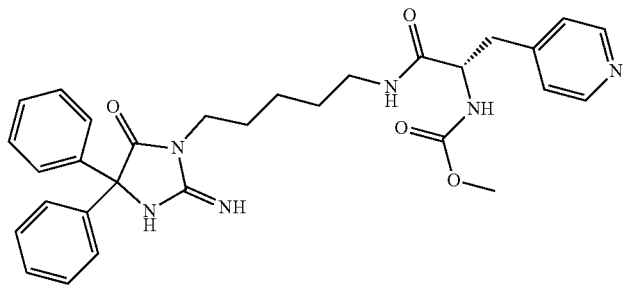 [SMILES: COC(=O)N[C@@H](Cc1ccncc1)C(=O)NCCCCCN1C(=N)NC(c2ccccc2)(c2ccccc2)C1=O] |
| 21 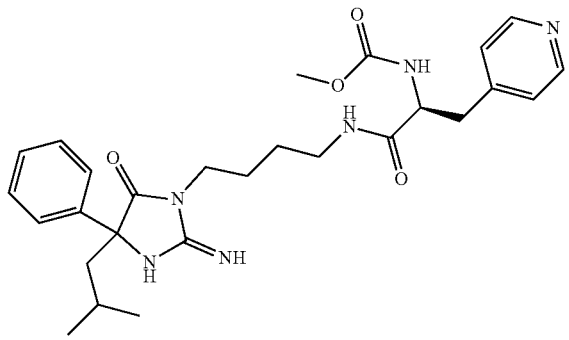 [SMILES: COC(=O)N[C@@H](Cc1ccncc1)C(=O)NCCCCN1C(=N)NC(CC(C)C)(c2ccccc2)C1=O] |

-continued
| No. |
| --- |
22
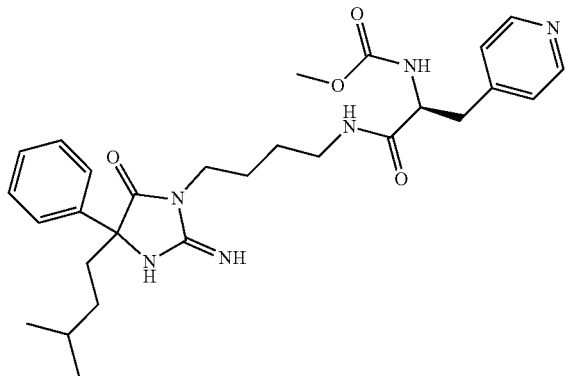 [SMILES: COC(=O)N[C@@H](Cc1ccncc1)C(=O)NCCCCN1C(=N)NC(CCC(C)C)(c2ccccc2)C1=O]
23
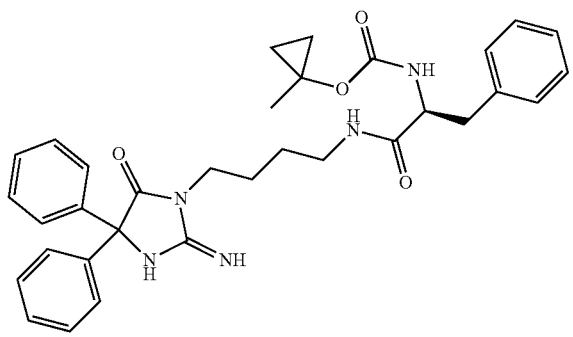 [SMILES: CC1(OC(=O)N[C@@H](Cc2ccccc2)C(=O)NCCCCN2C(=N)NC(c3ccccc3)(c3ccccc3)C2=O)CC1]
24
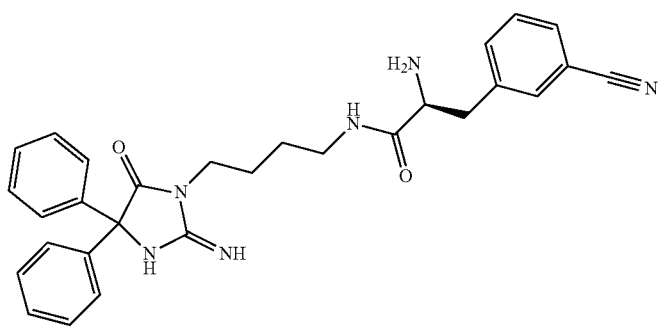 [SMILES: N#Cc1cccc(C[C@H](N)C(=O)NCCCCN2C(=N)NC(c3ccccc3)(c3ccccc3)C2=O)c1]
25
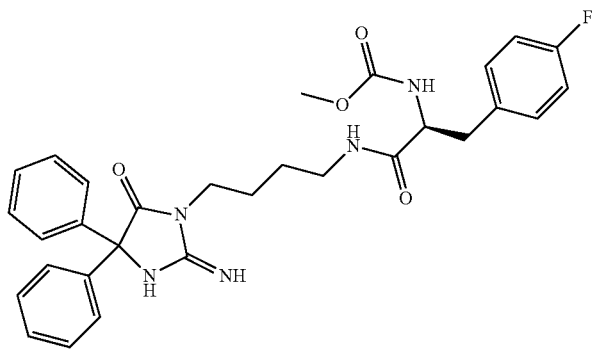 [SMILES: COC(=O)N[C@@H](Cc1ccc(F)cc1)C(=O)NCCCCN1C(=N)NC(c2ccccc2)(c2ccccc2)C1=O]

-continued
| No. |
|---|
| 26 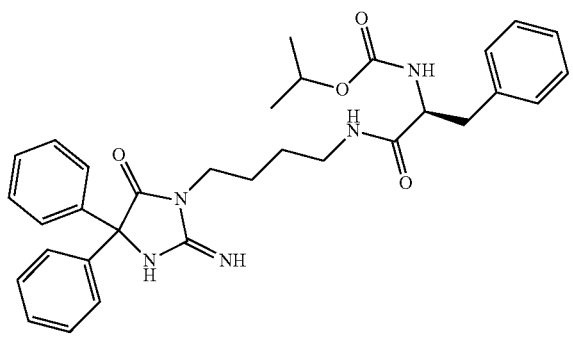 [SMILES: CC(C)OC(=O)N[C@@H](Cc1ccccc1)C(=O)NCCCCN1C(=N)NC(c2ccccc2)(c2ccccc2)C1=O] |
| 27 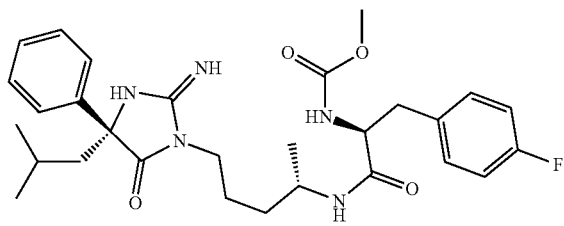 [SMILES: COC(=O)N[C@@H](Cc1ccc(F)cc1)C(=O)N[C@@H](C)CCCN1C(=N)N[C@](CC(C)C)(c2ccccc2)C1=O] |
| 28 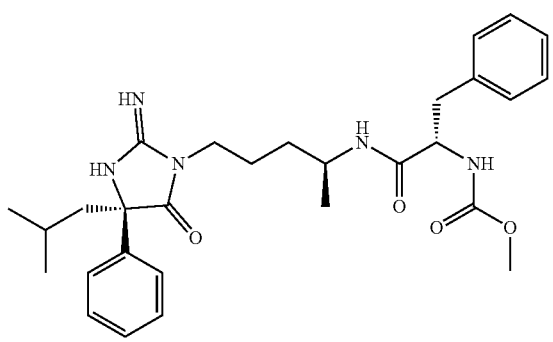 [SMILES: COC(=O)N[C@@H](Cc1ccccc1)C(=O)N[C@@H](C)CCCN1C(=N)N[C@](CC(C)C)(c2ccccc2)C1=O] |
| 29 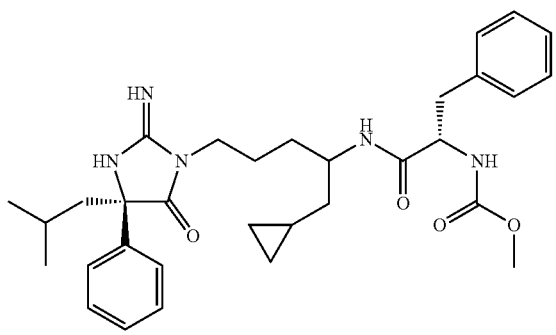 [SMILES: COC(=O)N[C@@H](Cc1ccccc1)C(=O)NC(CCCN1C(=N)N[C@](CC(C)C)(c2ccccc2)C1=O)CC1CC1] |
| 30 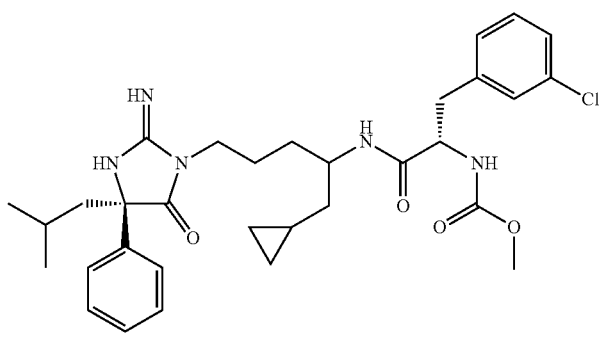 [SMILES: COC(=O)N[C@@H](Cc1cccc(Cl)c1)C(=O)NC(CCCN1C(=N)N[C@](CC(C)C)(c2ccccc2)C1=O)CC1CC1] |

| No. |
|---|
| 31 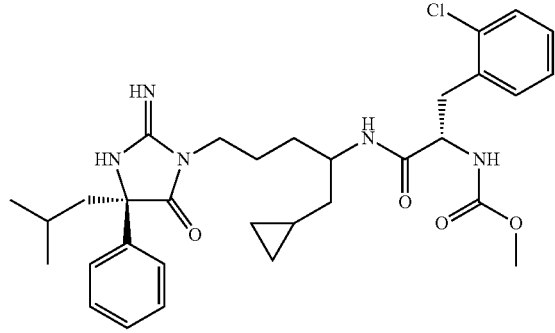 [SMILES: COC(=O)N[C@@H](Cc1ccccc1Cl)C(=O)NC(CCCN1C(=N)N[C@](CC(C)C)(c2ccccc2)C1=O)CC1CC1] |
| 32 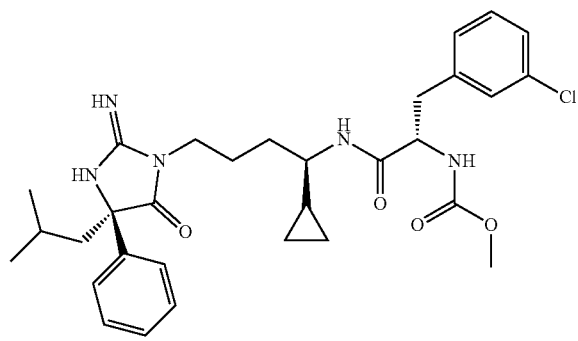 [SMILES: COC(=O)N[C@@H](Cc1cccc(Cl)c1)C(=O)N[C@H](CCCN1C(=N)N[C@](CC(C)C)(c2ccccc2)C1=O)C1CC1] |
| 33 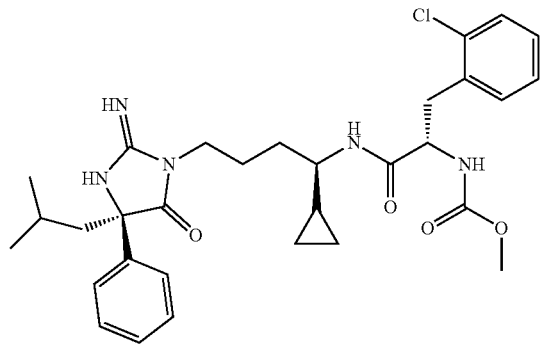 [SMILES: COC(=O)N[C@@H](Cc1ccccc1Cl)C(=O)N[C@H](CCCN1C(=N)N[C@](CC(C)C)(c2ccccc2)C1=O)C1CC1] |
| 34 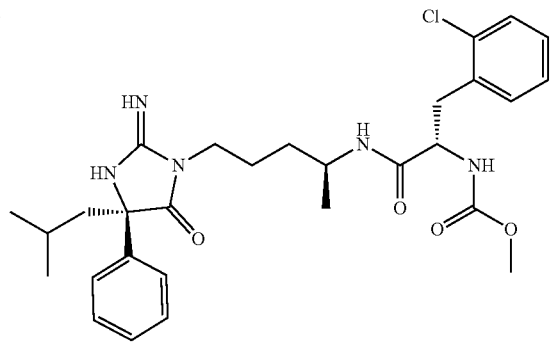 [SMILES: COC(=O)N[C@@H](Cc1ccccc1Cl)C(=O)N[C@@H](C)CCCN1C(=N)N[C@](CC(C)C)(c2ccccc2)C1=O] |

| No. |
|---|
| 35 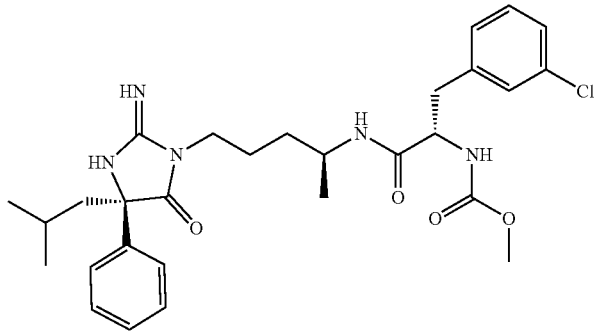 [SMILES: COC(=O)N[C@@H](Cc1cccc(Cl)c1)C(=O)N[C@@H](C)CCCN1C(=N)N[C@](CC(C)C)(c2ccccc2)C1=O] |
| 36 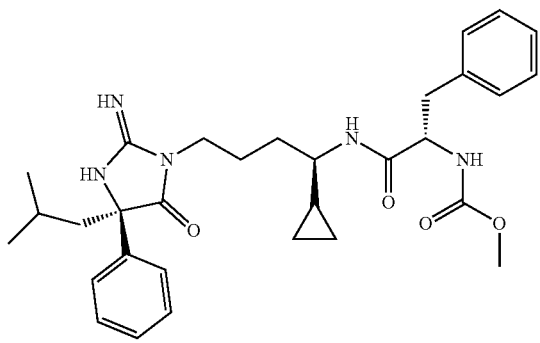 [SMILES: COC(=O)N[C@@H](Cc1ccccc1)C(=O)N[C@H](CCCN1C(=N)N[C@](CC(C)C)(c2ccccc2)C1=O)C1CC1] |
| 37 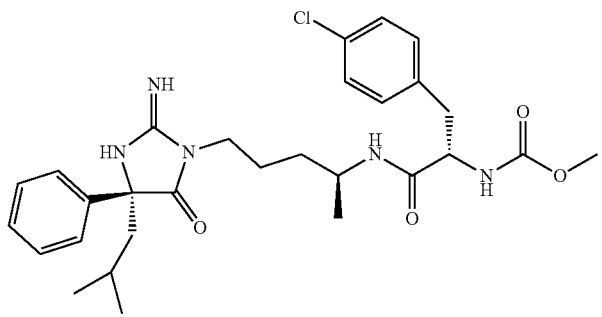 [SMILES: COC(=O)N[C@@H](Cc1ccc(Cl)cc1)C(=O)N[C@@H](C)CCCN1C(=N)N[C@](CC(C)C)(c2ccccc2)C1=O] |
| 38 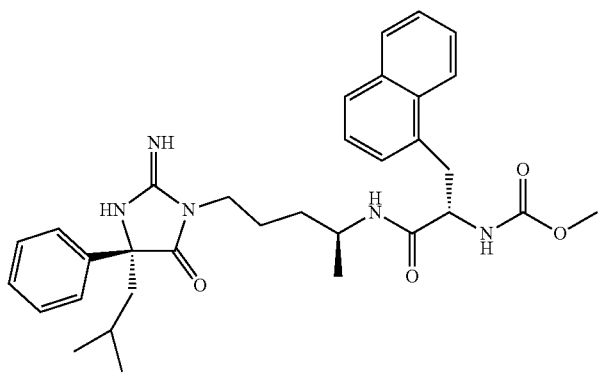 [SMILES: COC(=O)N[C@@H](Cc1cccc2ccccc12)C(=O)N[C@@H](C)CCCN1C(=N)N[C@](CC(C)C)(c2ccccc2)C1=O] |

| No. | |
|---|---|
| 39 | 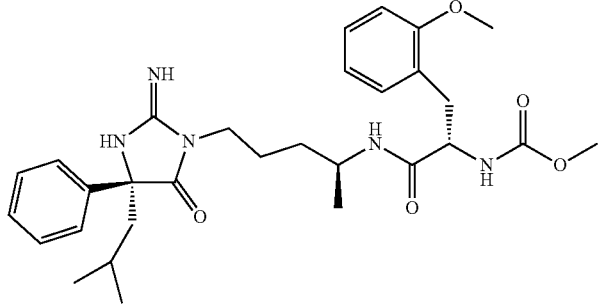 [SMILES: COC(=O)N[C@@H](Cc1ccccc1OC)C(=O)N[C@@H](C)CCCN1C(=N)N[C@](CC(C)C)(c2ccccc2)C1=O] |
| 40 | 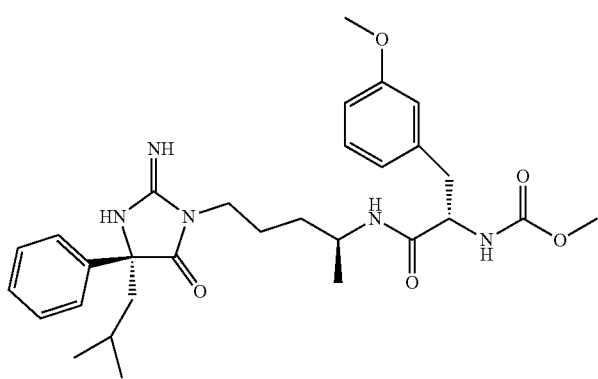 [SMILES: COC(=O)N[C@@H](Cc1cccc(OC)c1)C(=O)N[C@@H](C)CCCN1C(=N)N[C@](CC(C)C)(c2ccccc2)C1=O] |
| 41 | 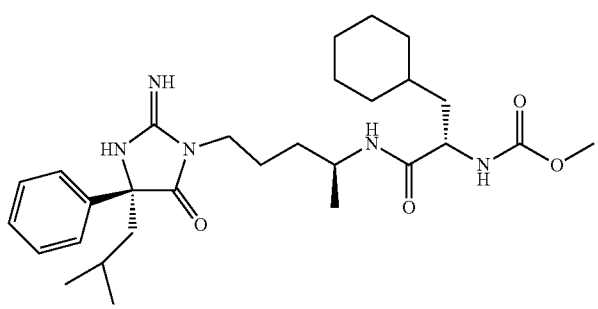 [SMILES: COC(=O)N[C@@H](CC1CCCCC1)C(=O)N[C@@H](C)CCCN1C(=N)N[C@](CC(C)C)(c2ccccc2)C1=O] |
| 42 | 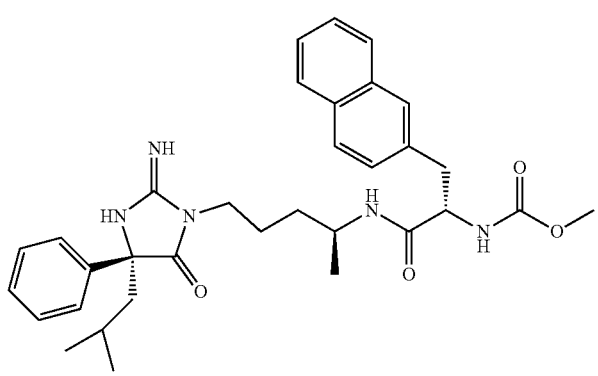 [SMILES: COC(=O)N[C@@H](Cc1ccc2ccccc2c1)C(=O)N[C@@H](C)CCCN1C(=N)N[C@](CC(C)C)(c2ccccc2)C1=O] |

| No. |
|---|
| 43 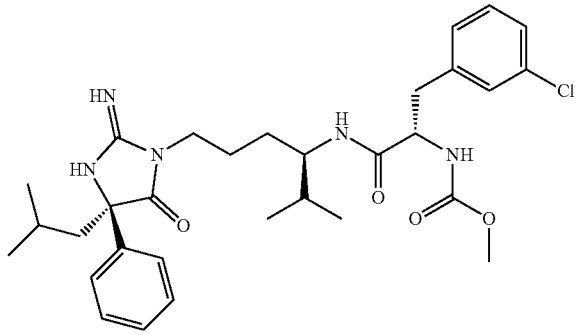 [SMILES: COC(=O)N[C@@H](Cc1cccc(Cl)c1)C(=O)N[C@H](CCCN1C(=N)N[C@](CC(C)C)(c2ccccc2)C1=O)C(C)C] |
| 44 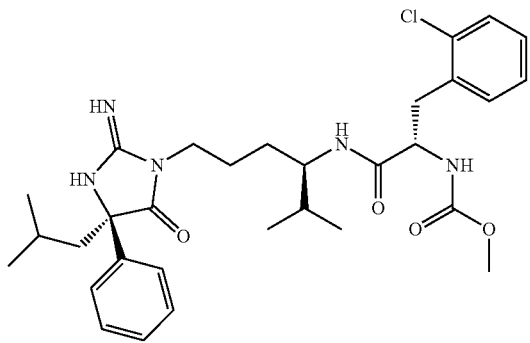 [SMILES: COC(=O)N[C@@H](Cc1ccccc1Cl)C(=O)N[C@H](CCCN1C(=N)N[C@](CC(C)C)(c2ccccc2)C1=O)C(C)C] |
| 45 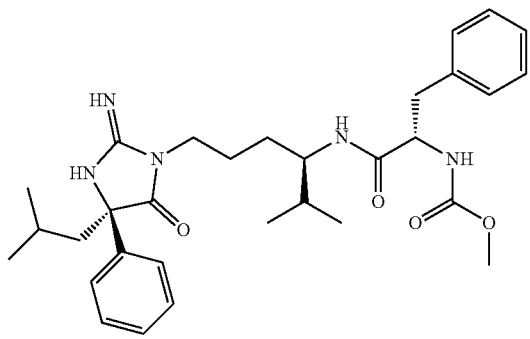 [SMILES: COC(=O)N[C@@H](Cc1ccccc1)C(=O)N[C@H](CCCN1C(=N)N[C@](CC(C)C)(c2ccccc2)C1=O)C(C)C] |
| 46 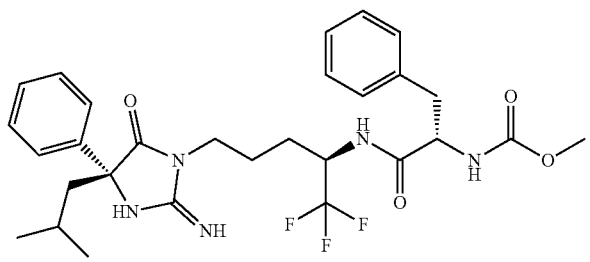 [SMILES: COC(=O)N[C@@H](Cc1ccccc1)C(=O)N[C@H](CCCN1C(=N)N[C@](CC(C)C)(c2ccccc2)C1=O)C(F)(F)F] |

| No. |
|---|
| 47 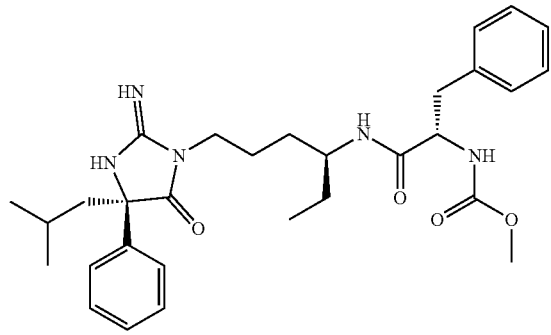 [SMILES: CC[C@@H](CCCN1C(=N)N[C@](CC(C)C)(c2ccccc2)C1=O)NC(=O)[C@H](Cc1ccccc1)NC(=O)OC] |
| 48 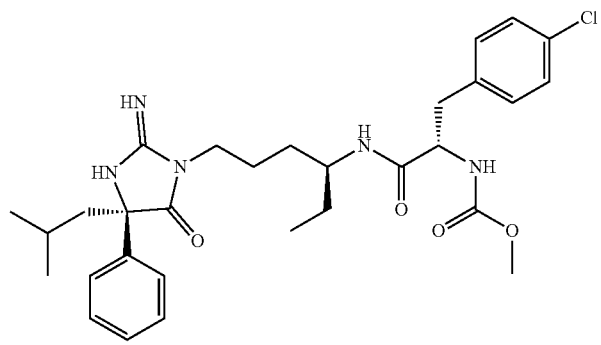 [SMILES: CC[C@@H](CCCN1C(=N)N[C@](CC(C)C)(c2ccccc2)C1=O)NC(=O)[C@H](Cc1ccc(Cl)cc1)NC(=O)OC] |
| 49 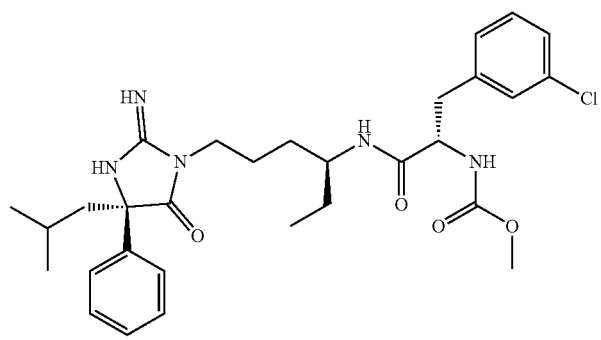 [SMILES: CC[C@@H](CCCN1C(=N)N[C@](CC(C)C)(c2ccccc2)C1=O)NC(=O)[C@H](Cc1cccc(Cl)c1)NC(=O)OC] |
| 50 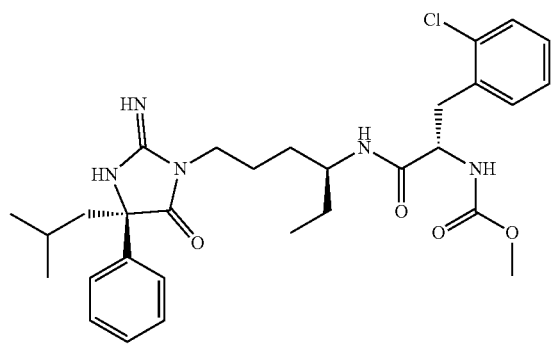 [SMILES: CC[C@@H](CCCN1C(=N)N[C@](CC(C)C)(c2ccccc2)C1=O)NC(=O)[C@H](Cc1ccccc1Cl)NC(=O)OC] |

| No. |
|---|
| 51 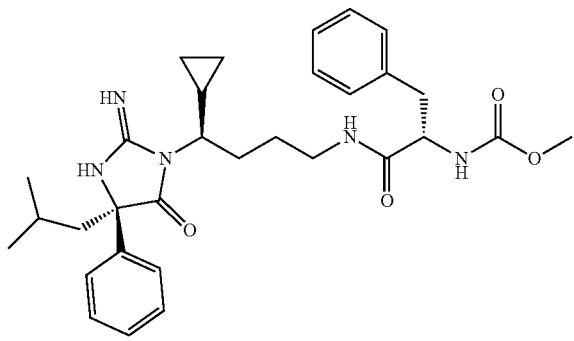 [SMILES: COC(=O)N[C@@H](Cc1ccccc1)C(=O)NCCC[C@H](C1CC1)N1C(=N)N[C@](CC(C)C)(c2ccccc2)C1=O] |
| 52 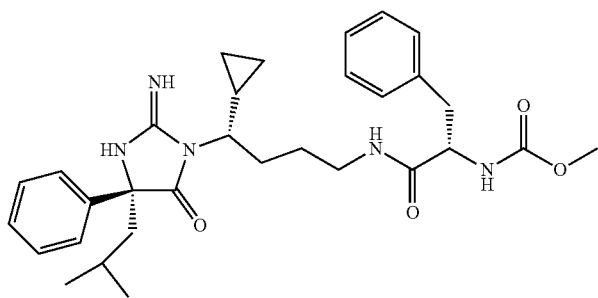 [SMILES: COC(=O)N[C@@H](Cc1ccccc1)C(=O)NCCC[C@@H](C1CC1)N1C(=N)N[C@](CC(C)C)(c2ccccc2)C1=O] |
| 53 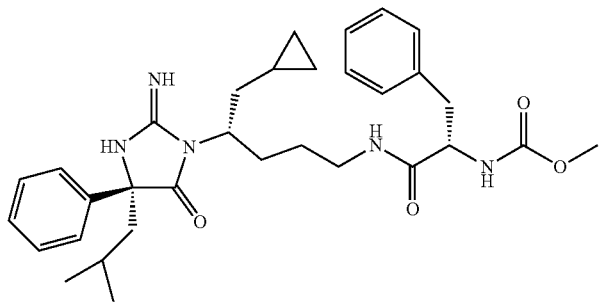 [SMILES: COC(=O)N[C@@H](Cc1ccccc1)C(=O)NCCC[C@@H](CC1CC1)N1C(=N)N[C@](CC(C)C)(c2ccccc2)C1=O] |
| 54 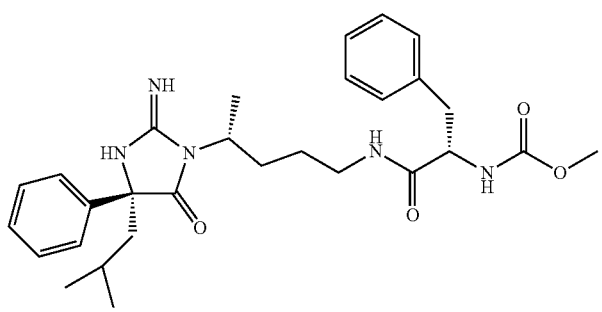 [SMILES: COC(=O)N[C@@H](Cc1ccccc1)C(=O)NCCC[C@@H](C)N1C(=N)N[C@](CC(C)C)(c2ccccc2)C1=O] |
| 55 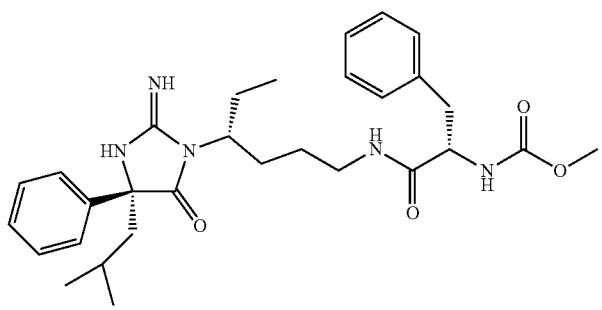 [SMILES: CC[C@H](CCCNC(=O)[C@H](Cc1ccccc1)NC(=O)OC)N1C(=N)N[C@](CC(C)C)(c2ccccc2)C1=O] |
or

| No. | |
|---|---|
| 56 | 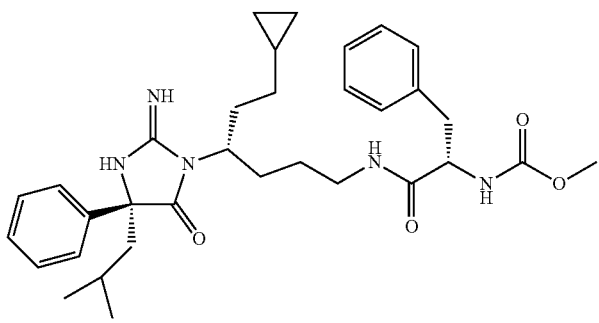 [SMILES: COC(=O)N[C@@H](Cc1ccccc1)C(=O)NCCC[C@@H](CCC1CC1)N1C(=N)N[C@](CC(C)C)(c2ccccc2)C1=O] | or a pharmaceutically acceptable salt thereof.

10. A pharmaceutical composition comprising an effective amount of the compound according to claim 1, or a pharmaceutically acceptable salt thereof, and a pharmaceutically acceptable carrier.

11. A method for the treatment or prophylaxis of infection by HIV or for the treatment, prophylaxis, or delay in the onset of AIDS in a subject in need thereof, which comprises administering to the subject an effective amount of the compound of claim 1, or a pharmaceutically acceptable salt thereof.

12. A pharmaceutical composition comprising an effective amount of the compound of claim 1, or a pharmaceutically acceptable salt thereof, and a pharmaceutically acceptable carrier and further comprising an effective amount of an anti-HIV agent selected from the group consisting of HIV antiviral agents, immunomodulators, and anti-infective agents.

13. The pharmaceutical composition of claim 12, wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

* * * * *